(12) United States Patent
Davies et al.

(10) Patent No.: US 7,205,408 B2
(45) Date of Patent: Apr. 17, 2007

(54) QUINOLINES AND NITROGENATED DERIVATIVE THEREOF SUBSTITUTED IN 4-POSITION BY A PIPERIDINE-CONTAINING MOIETY AND THEIR USE AS ANTIBACTERIAL AGENTS

(75) Inventors: David Thomas Davies, Harlow (GB); Graham Elgin Jones, Harlow (GB); Roger Edward Markwell, Harlow (GB); William Miller, Collegville, PA (US); Neil David Pearson, Harlow (GB)

(73) Assignee: SmithKline Beecham, p.l.c., Brentford (GB)

( * ) Notice: Subject to any disclaimer, the term of this patent is extended or adjusted under 35 U.S.C. 154(b) by 188 days.

(21) Appl. No.: 10/466,394

(22) PCT Filed: Jan. 22, 2002

(86) PCT No.: PCT/EP02/00587

§ 371 (c)(1),
(2), (4) Date: Jan. 26, 2004

(87) PCT Pub. No.: WO02/056882

PCT Pub. Date: Jul. 25, 2002

(65) Prior Publication Data

US 2004/0138219 A1 Jul. 15, 2004

(30) Foreign Application Priority Data

Jan. 2, 1920 (GB) ................................. 0101577.5

(51) Int. Cl.
*C07D 215/16* (2006.01)
*C07D 215/12* (2006.01)
*A61K 31/47* (2006.01)

(52) U.S. Cl. ....................... 546/153; 546/176; 546/122; 514/314; 514/224.2; 514/227.8; 514/230.8; 544/52; 544/105; 544/354; 544/224

(58) Field of Classification Search ................. 514/314; 546/153, 176
See application file for complete search history.

(56) References Cited

U.S. PATENT DOCUMENTS

| | | | |
|---|---|---|---|
| 5,264,431 A | 11/1993 | Wacker et al. ............... | 514/211 |
| 5,310,743 A | 5/1994 | Schilling et al. ............. | 514/311 |
| 5,541,195 A | 7/1996 | Schilling et al. ............. | 514/311 |
| 5,646,144 A | 7/1997 | Schilling et al. ............. | 514/241 |
| 6,403,610 B1 | 6/2002 | Malleron et al. ............ | 514/314 |
| 6,602,882 B1 | 8/2003 | Davies et al. ................ | 514/300 |
| 6,602,884 B2 | 8/2003 | Bacque et al. ............... | 514/314 |
| 6,603,005 B2 | 8/2003 | Baque et al. ................. | 546/176 |
| 6,803,369 B1 | 10/2004 | Erskine et al. .......... | 514/253.06 |
| 6,815,547 B2 | 11/2004 | Bacque et al. ............... | 546/174 |
| 6,903,217 B2 | 6/2005 | Bacque et al. ............... | 546/180 |
| 6,911,442 B1 | 6/2005 | Davies et al. ............. | 514/230.5 |
| 6,962,917 B2 | 11/2005 | Davies et al. ............. | 514/264.1 |
| 6,989,447 B2 | 1/2006 | Markwell et al. ........... | 546/152 |
| 7,001,913 B1 | 2/2006 | Davies et al. ................ | 514/300 |
| 2003/0203917 A1 | 10/2003 | Erskine et al. ......... | 514/253.06 |
| 2003/0212084 A1 | 11/2003 | Hatton et al. .......... | 514/266.22 |
| 2004/0053928 A1 | 3/2004 | Davies et al. ................ | 514/248 |
| 2004/0077655 A1 | 4/2004 | Dartois et al. ......... | 514/253.05 |
| 2004/0077656 A1 | 4/2004 | Markwell et al. ...... | 514/253.05 |
| 2004/0171620 A1 | 9/2004 | Brooks et al. .............. | 514/248 |
| 2004/0198755 A1 | 10/2004 | Dartois et al. ......... | 514/266.22 |
| 2004/0198756 A1 | 10/2004 | Davies et al. .......... | 514/266.22 |
| 2006/0014749 A1 | 1/2006 | Davies et al. ................ | 514/249 |

FOREIGN PATENT DOCUMENTS

| | | |
|---|---|---|
| BE | 772190 A1 | 1/1972 |
| CA | 2004986 A1 | 6/1990 |
| EP | 0238868 A2 | 9/1987 |
| EP | 0304493 A1 | 3/1989 |
| EP | 0374095 A2 | 6/1990 |
| EP | 0532456 A1 | 3/1993 |
| EP | 0541486 A1 | 5/1993 |
| EP | 0532456 B1 | 3/1995 |
| EP | 0823429 A1 | 2/1998 |
| EP | 1218370 B1 | 12/2004 |
| GB | 1345872 | 2/1974 |
| GB | 1537867 | 1/1979 |
| JP | 1995179407 A | 7/1995 |
| WO | WO 95/09853 | 4/1995 |
| WO | WO 96/15128 | 5/1996 |
| WO | WO 96/38144 | 12/1996 |
| WO | WO 97/03069 | 1/1997 |
| WO | WO 97/17957 | 5/1997 |

(Continued)

OTHER PUBLICATIONS

Co-pending U.S. Appl. No. 09/600,984, filed Feb. 15, 2001, Coates et al., Quinoline Derivatives as Antibacterials, WO99/37635.

(Continued)

*Primary Examiner*—D. Margaret Seaman
(74) *Attorney, Agent, or Firm*—Loretta J. Sauermelch; Mary E. McCarthy; Charles M. Kinzig

(57) ABSTRACT

Piperidine derivatives and pharmaceutically acceptable derivatives thereof useful in methods of treatment of bacterial infections in mammals, particularly in man.

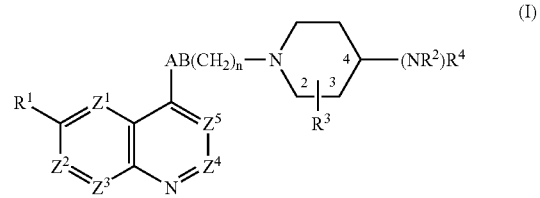

(I)

13 Claims, No Drawings

FOREIGN PATENT DOCUMENTS

| | | |
|---|---|---|
| WO | WO 97/28167 | 8/1997 |
| WO | WO 97/45119 | 12/1997 |
| WO | WO 98/02438 | 1/1998 |
| WO | WO 99/37635 | 7/1999 |
| WO | WO 00/21948 | 4/2000 |
| WO | WO 00/21952 | 4/2000 |
| WO | WO 00/43383 | 7/2000 |
| WO | WO 00/78748 | 12/2000 |
| WO | WO 01/07432 * | 2/2001 |
| WO | WO 01/07433 A2 | 2/2001 |
| WO | WO 01/25227 A2 | 4/2001 |
| WO | WO 01/087839 A1 | 11/2001 |
| WO | WO 02/08224 A1 | 1/2002 |
| WO | WO 02/24684 A1 | 3/2002 |
| WO | WO 02/40474 A2 | 5/2002 |
| WO | WO 02/50040 A1 | 6/2002 |
| WO | WO 02/50061 A1 | 6/2002 |
| WO | WO 02/072572 A1 | 9/2002 |
| WO | WO 02/96907 A1 | 12/2002 |
| WO | WO 03/010138 A2 | 2/2003 |
| WO | WO 03/087098 | 10/2003 |

OTHER PUBLICATIONS

Co-pending U.S. Appl. No. 09/889,820, filed Sep. 20, 2001, Davies et al., Quinoline Derivatives as Antibacterials, WO00/43383.

Co-pending U.S. Appl. No. 11/292,011, filed Jul. 19, 2002, Davies et al., Compounds and Methods for the Treatment of Disease.

Co-pending U.S. Appl. No. 10/868,351, filed Jun. 15, 2004, Erskine et al., Compounds and Methods for the Treatment of Disease.

Co-pending U.S. Appl. No. 10/199,933, filed Jul. 19, 2002, Erskine et al., Compounds and Methods for the Treatment of Disease.

Co-pending U.S. Appl. No. 10/937,468, filed Sep. 9, 2004, Erskine et al., Compounds and Methods for the Treatment of Disease.

* cited by examiner

QUINOLINES AND NITROGENATED DERIVATIVE THEREOF SUBSTITUTED IN 4-POSITION BY A PIPERIDINE-CONTAINING MOIETY AND THEIR USE AS ANTIBACTERIAL AGENTS

CROSS REFERENCES TO RELATED APPLICATIONS

This application is a National Stage Application filed under 35 U.S.C.§371 of PCT/EP02/00587, filed on Jan. 22, 2002, which claims priority of GB Application No. 0101577.5, filed Jan. 22, 2001.

This invention relates to novel compounds, compositions containing them and their use as antibacterials.

WO99/37635, WO00/21948, WO00/21952, WO00/43383, WO00/78748, WO01/07432 and WO01/07433 disclose piperidine and piperazine derivatives having antibacterial activity.

We have now found a novel group of aminopiperidines which have antibacterial activity.

This invention provides a compound of formula (I) or a pharmaceutically acceptable derivative thereof:

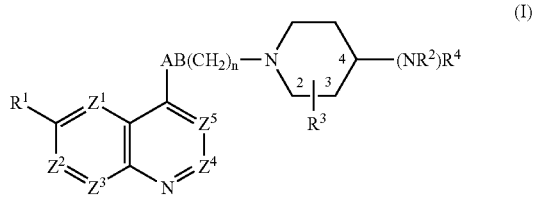

(I)

wherein:
one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;

$R^1$ and $R^{1a}$ are independently hydrogen; hydroxy; $(C_{1-6})$alkoxy optionally substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted$(C_{1-6})$alkyl; halogen; $(C_{1-6})$alkyl; $(C_{1-6})$alkylthio; trifluoromethyl; trifluoromethoxy; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups;

or when $Z^5$ is $CR^{1a}$, $R^{1a}$ may instead be cyano, hydroxymethyl or carboxy; provided that when none of $Z^1$, $Z^2$, $Z^3$, $Z^4$ and $Z^5$ is N, then $R^1$ is not hydrogen;

$R^2$ is hydrogen, or $(C_{1-4})$alkyl or $(C_{2-4})$alkenyl optionally substituted with 1 to 3 groups selected from:
amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$alkenyloxycarbonyl, $(C_{2-4})$alkenylcarbonyl; oxo; $(C_{1-4})$alkylsulphonyl; $(C_{2-4})$alkenylsulphonyl; or $(C_{1-4})$aminosulphonyl wherein the amino group is optionally substituted by $(C_{1-4})$alkyl or $(C_{2-4})$alkenyl;

$R^3$ is hydrogen; or $R^3$ is in the 2-, 3- or 4-position and is:
carboxy, $(C_{1-6})$alkoxycarbonyl; $(C_{2-6})$alkenyloxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the substituents listed above for $R^3$ and/or 0 to 2 groups $R^{12}$ independently selected from:
halogen; $(C_{1-6})$alkylthio; trifluoromethyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl; or when $R^3$ is in the 3-position, hydroxy optionally substituted as described above;

in addition when $R^3$ is disubstituted with a hydroxy or amino containing substituent and carboxy containing substituent these may together form a cyclic ester or amide linkage, respectively;

$R^4$ is a group —U—$R^5$ where

U is selected from CO, $SO_2$ and $CH_2$ and $R^5$ is an optionally substituted bicyclic carbocyclic or heterocyclic ring system (A):

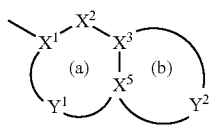

(A)

containing up to four heteroatoms in each ring in which
ring (a) is aromatic and ring (b) is non-aromatic;
$X^1$ is C or N;
$X^2$ is N, $NR^{13}$, O, $S(O)_x$, CO or $CR^{14}$;
$X^3$ and $X^5$ are independently N or C;
$Y^1$ is a 0 to 4 atom linker group each atom of which is independently selected from N, $NR^{13}$, O, $S(O)_x$, CO and $CR^{14}$;
$Y^2$ is a 2 to 6 atom linker group, each atom of $Y^2$ being independently selected from N, $NR^{13}$, O, $S(O)_x$, CO, $CR^{14}$ and $CR^{14}R^{15}$;
each of $R^{14}$ and $R^{15}$ is independently selected from: H; $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally mono- or di-substituted by $(C_{1-4})$alkyl or $(C_{2-4})$alkenyl; aryl; aryl$(C_{1-4})$alkyl; aryl$(C_{1-4})$alkoxy;
each $R^{13}$ is independently H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl$(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;
each x is independently 0, 1 or 2
n is 0 and AB is $NR^{11}$ CO, CO—$CR^8R^9$, $CR^6R^7$—CO, $NHR^{11}SO_2$, $CR^6R^7$—$SO_2$ or $CR^6R^7$—$CR^8R^9$;
or n is 1 and AB is $NR^{11}$ CO, CO—$CR^8R^9$, $CR^6R^7$—CO, $NR^{11}SO_2$, $CONR^{11}$, $CR^6R^7$—$CR^8R^9$, O—$CR^8R^9$ or $NR^{11}$—$CR^8R^9$;
wherein $CR^6R^7$ is $CH_2$, CHOH, $CH(NH_2)$, C(Me)(OH) or CH(Me) and $CR^8R^9$ is $CH_2$;
$R^{10}$ is selected from $(C_{1-4})$alkyl; $(C_{2-4})$alkenyl and aryl any of which may be optionally substituted by a group $R^{12}$ as defined above, carboxy; aminocarbonyl wherein the amino group is optionally substituted by hydroxy. $(C_{1-6})$alkyl, $(C_{2-6})$alkenyl. $(C_{1-6})$alkylsulphonyl, trifluoromethylsulphonyl, (2-6)alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; and
$R^{11}$ is hydrogen; trifluoromethyl, $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl. $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl, or where one of $R^3$ and $R^6$ or $R^7$ contains a carboxy group and the other contains a hydroxy or amino group they may together form a cyclic ester or amide linkage.

This invention also provides a method of treatment of bacterial infections in mammals, particularly in man, which method comprises the administration to a mammal in need of such treatment an effective amount of a compound of formula (I), or a pharmaceutically acceptable derivative thereof.

The invention also provides the use of a compound of formula (I), or a pharmaceutically acceptable derivative thereof, in the manufacture of a medicament for use in the treatment of bacterial infections in mammals.

The invention also provides a pharmaceutical composition comprising a compound of formula (I), or a pharmaceutically acceptable derivative thereof, and a pharmaceutically acceptable carrier.

Preferably $Z^5$ is CH or N, $Z^3$ is CH or CF and $Z^1$, $Z^2$ and $Z^4$ are each CH, or $Z^1$ is N, $Z^3$ is CH or CF and $Z^2$, $Z^4$ and $Z^5$ are each CH.

When $R^1$ or $R^{1a}$ is substituted alkoxy it is preferably $(C_{2-6})$alkoxy substituted by optionally N-substituted amino, guanidino or amidino, or $(C_{1-6})$alkoxy substituted by piperidyl. Suitable examples of $R^1$ and $R^{1a}$ alkoxy include methoxy, trifluoromethoxy, n-propyloxy, iso-butyloxy, aminoethyloxy, aminopropyloxy, aminobutyloxy, aminopentyloxy, guanidinopropyloxy, piperidin-4-ylmethyloxy, phthalimido pentyloxy or 2-aminocarbonylprop-2-oxy.

Preferably $R^1$ and $R^{1a}$ are independently methoxy, amino$(C_{3-5})$alkyloxy, guanidino$(C_{3-5})$alkyloxy, piperidyl$(C_{3-5})$alkyloxy, nitro or fluoro; more preferably methoxy, amino$(C_{3-5})$alkyloxy or guanidino$(C_{3-5})$alkyloxy. Most preferably $R^1$ is methoxy and $R^{1a}$ is H or when $Z^3$ is $CR^{1a}$ it may be C—F.

When $Z^5$ is $CR^{1a}$, $R^{1a}$ is preferably hydrogen, cyano, hydroxymethyl or carboxy, most preferably hydrogen.

Preferably n is 0.

$R^2$ is preferably hydrogen; $(C_{1-4})$alkyl substituted with carboxy, optionally substituted hydroxy, optionally substituted aminocarbonyl, optionally substituted amino or $(C_{1-4})$alkoxycarbonyl; or $(C_{2-4})$alkenyl substituted with $(C_{1-4})$alkoxycarbonyl or carboxy. More preferred groups for $R^2$ are hydrogen, carboxymethyl, hydroxyethyl, aminocarbonylmethyl, ethoxycarbonylmethyl, ethoxycarbonylallyl and carboxyallyl, most preferably hydrogen.

Preferred examples of $R^3$ include hydrogen; optionally substituted hydroxy; $(C_{1-4})$alkoxycarbonyl; $(C_{1-4})$ alkyl; ethenyl; optionally substituted 1-hydroxy-$(C_{1-4})$ alkyl; optionally substituted aminocarbonyl; carboxy$(C_{1-4})$alkyl; optionally substituted aminocarbonyl$(C_{1-4})$alkyl; cyano $(C_{1-4})$alkyl; optionally substituted 2-oxo-oxazolidinyl and optionally substituted 2-oxo-oxazolidinyl$(C_{1-4}$alkyl). More preferred $R^3$ groups are hydrogen; $CONH_2$; 1-hydroxyalkyl e.g. $CH_2OH$, $CH(OH)CH_2CN$; $CH_2CO_2H$; $CH_2CONH_2$; $CONHCH_2CONH_2$; 1,2-dihydroxyalkyl e.g. CH(OH) $CH_2OH$; $CH_2CN$; 2-oxo-oxazolidin-5-yl and 2-oxo-oxazolidin-5-yl$(C_{1-4}$alkyl). Most preferably $R^3$ is hydrogen.

$R^3$ is preferably in the 3- or 4-position.

When $R^3$ is in the 3-position, preferably it is trans to $(NR^2)R^4$.

When $R^3$ and $R^6$, $R^7$, $R^8$ or $R^9$ together form a cyclic ester or amide linkage, it is preferred that the resulting ring is 5-7 membered.

Preferably n=0.

When A is CH(OH) the R-stereochemistry is preferred.

Preferably A is NH, NCH$_3$, CH$_2$, CHOH, CH(NH$_2$), C(Me)(OH) or CH(Me).

Preferably B is CH$_2$ or CO.

Preferably A-B is CHOH—CH$_2$, NR$^{11}$—CH$_2$ or NR$^{11}$—CO.

Particularly preferred are those compounds where n=0, A is NH and B is CO, or A is CHOH and B is CH$_2$, when more preferably A is the R-isomer of CHOH.

Preferably R$^{11}$ is hydrogen or (C$_{1-4}$)alkyl e.g. methyl, more preferably hydrogen.

U is most preferably CH$_2$.

Preferably in the heterocyclic ring (A) Y$^2$ has 3–5 atoms, more preferably 4 atoms, including NR$^{13}$, O or S bonded to X$^5$ and NHCO bonded via N to X$^3$, or O or NH bonded to X$^3$. The ring (a) preferably contains aromatic nitrogen, and more preferably ring (a) is pyridine. Examples of rings (A) include optionally substituted: 1,1,3-trioxo-1,2,3,4-tetrahydrol 1$^6$-benzo[1,4]thiazin-3-one-6-yl, benzo[1,3]dioxol-5-yl, 4H-benzo[1,4]oxazin-3-one-6-yl, 2,3-dihydro-benzo[1,4]dioxin-6-yl, 2-oxo-2,3-dihydro-benzooxazol-6-yl, 3-substituted-3H-benzooxazol-2-one-6-yl, 3-substituted-3H-benzooxazole-2-thione-6-yl, 3-substituted-3H-benzothiazol-2-one-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, benzo[1,3]dioxol-5-yl, 1H-pyrido[2,3-b][1,4]thiazin-2-one-7-yl (2-oxo-2,3-dihydro-1H-pyrido[2,3-b]thiazin-7-yl), 2,3-dihydro-1H-pyrido[2,3-b][1,4]thiazin-7-yl, 2-oxo-2,3-dihydro-1H-pyrido[3,4-b]thiazin-7-yl, 2,3-dihydro-[1,4]dioxino[2,3-b]pyridin-6-yl, 2,3-dihydro-[1,4]dioxino[2,3-c]pyridin-7-yl, 2,3-1,4]dioxino[2,3-b]pyridin-7-yl, 3,4-dihydro-2H-benzo[1,4]oxazin-6-yl, 3,4-dihydro-2H-benzo[1,4]thiazin-6-yl, 3-oxo-3,4-dihydro-2H-pyrido[3,2-b][1,4]oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl.

R$^{13}$ is preferably H if in ring (a) or in addition (C$_{1-4}$)alkyl such as methyl or isopropyl when in ring (b). More preferably, in ring (b) R$^{13}$ is H when NR$^{13}$ is bonded to X$^3$ and (C$_{1}$-14)alkyl when NR$^{13}$ is bonded to X$^5$.

R$^{14}$ and R$^{15}$ are preferably independently selected from hydrogen, halo, hydroxy, (C$_{1-4}$)alkoxy, trifluoromethoxy, nitro, cyano, aryl(C$_{1-4}$)alkoxy and (C$_{1-4}$)alkylsulphonyl. More preferably R$^{15}$ is hydrogen.

More preferably each R$^{14}$ is selected from hydrogen, chloro, fluoro, hydroxy, methoxy, trifluoromethoxy, benzyloxy, nitro, cyano and methylsulphonyl. Most preferably R$^{14}$ is selected from hydrogen, fluorine or nitro. Preferably 0–3 groups R$^{14}$ are substituents other than hydrogen. Preferably when R$^{14}$ is not hydrogen, X$^4$ is CR$^{14}$ and/or CR$^{14}$ is a component of Y$^2$.

Most preferred groups R$^5$ include:
2,3-dihydro-benzo[1,4]dioxin-6-yl
benzo[1,3]dioxol-5-yl
2,2-difluoro-benzo[1,3]dioxol-5-yl
4H-benzo[1,4]oxazin-3-one-6-yl
4H-benzo[1,4]thiazin-3-one-6-yl
7-fluoro-4H-benzo[1,4]oxazin-3-one-6-yl
6-chloro-benzo[1,3]dioxol-5-yl 5-fluoro-3-methyl-3H-benzooxazol-2-one-6-yl
2,3-dihydro-[1,4]dioxino[2,3-c]pyridin-7-yl
3-oxo-3,4-dihydro-2H-pyrido[3,2-b][1,4]thiazin-6-yl
3,4-dihydro-2H-pyrido[3,2-b][1,4]thiazin-6-yl
7-bromo-3-oxo-3,4-dihydro-2H-pyrido[3,2-b][1,4]thiazin-6-yl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo. Haloalkyl moieties include 1-3 halogen atoms.

Unless otherwise defined, the term "heterocyclic" as used herein includes optionally substituted aromatic and non-aromatic, single and fused, rings suitably containing up to four hetero-atoms in each ring selected from oxygen, nitrogen and sulphur, which rings may be unsubstituted or C-substituted by, for example, up to three groups selected from (C$_{1-4}$)alkylthio; halo; carboxy(C$_{1-4}$)alkyl; halo(C$_{1-4}$)alkoxy; halo(C$_{1-4}$)alkyl; (C$_{1-4}$)alkyl; (C$_{2-4}$)alkenyl; (C$_{1-4}$)alkoxycarbonyl; formyl; (C$_{1-4}$)alkylcarbonyl; (C$_{2-4}$)alkenyloxycarbonyl; (C$_{2-4}$)alkenylcarbonyl; (C$_{1-4}$)alkylcarbonyloxy; (C$_{1-4}$)alkoxycarbonyl(C$_{1-4}$)alkyl; hydroxy; hydroxy(C$_{1-4}$)alkyl; mercapto(C$_{1-4}$)alkyl; (C$_{1-4}$)alkoxy; nitro; cyano, carboxy; amino or aminocarbonyl optionally substituted as for corresponding substituents in R$^3$; (C$_{1-4}$)alkylsulphonyl; (C$_{2-4}$)alkenylsulphonyl; or aminosulphonyl wherein the amino group is optionally substituted by (C$_{1-4}$)alkyl or (C$_{2-4}$)alkenyl; optionally substituted aryl, aryl(C$_{1-4}$)alkyl or aryl(C$_{1-4}$)alkoxy and oxo groups.

Each heterocyclic ring suitably has from 4 to 7, preferably 5 or 6, ring atoms. A fused heterocyclic ring system may include carbocyclic rings and need include only one heterocyclic ring.

Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; (C$_{1-4}$)alkyl optionally substituted by hydroxy, (C$_{1-6}$)alkoxy, (C$_{1-6}$)alkylthio, halo or trifluoromethyl; (C$_{2-4}$)alkenyl; aryl; aryl (C$_{1-4}$)alkyl; (C$_{1-4}$)alkoxycarbonyl; (C$_{1-4}$)alkylcarbonyl; formyl; (C$_{1-6}$)alkylsulphonyl; or aminocarbonyl wherein the amino group is optionally substituted by (C$_{1-4}$)alkoxycarbonyl, (C$_{1-4}$)alkylcarbonyl, (C$_{2-4}$)alkenyloxycarbonyl, (C$_{2-4}$)alkenylcarbonyl, (C$_{1-4}$)alkyl or (C$_{2-4}$)alkenyl and optionally further substituted by (C$_{1-4}$)alkyl or (C$_{2-4}$)alkenyl.

When used herein the term "aryl", includes optionally substituted phenyl and naphthyl.

Aryl groups may be optionally substituted with up to five, preferably up to three, groups selected from (C$_{1-4}$)alkylthio; halo; carboxy(C$_{1-4}$)alkyl; halo(C$_{1-4}$)alkoxy; halo(C$_{1-4}$)alkyl; (C$_{1-4}$)alkyl; (C$_{2-4}$)alkenyl; (C$_{1-4}$)alkoxycarbonyl; formyl; (C$_{1-4}$)alkylcarbonyl; (C$_{2-4}$)alkenyloxycarbonyl; (C$_{2-4}$)alkenylcarbonyl; (C$_{1-4}$)alkylcarbonyloxy; (C$_{1-4}$)alkoxycarbonyl(C$_{1-4}$)alkyl; hydroxy; hydroxy(C$_{1-4}$)alkyl; mercapto (C$_{1-4}$)alkyl; (C$_{1-4}$)alkoxy; nitro; cyano; carboxy; amino or aminocarbonyl optionally substituted as for corresponding substituents in R$^3$; (C$_{1-4}$)alkylsulphonyl; (C$_{2-4}$)alkenylsulphonyl; or aminosulphonyl wherein the amino group is optionally substituted by (C$_{1-4}$)alkyl or (C$_{2-4}$)alkenyl; phenyl, phenyl(C$_{1-4}$)alkyl or phenyl(C$_{1-4}$)alkoxy The term "acyl" includes formyl and $(C_{1-6})$alkylcarbonyl group.

Preferred compounds of formula (I) include:
(R)-2-{4-[(2,3-Dihydro-benzo[1,4]dioxin-6-ylmethyl)-amino]-piperidin-1-yl}-1-(6-methoxy-quinolin-4-yl)-ethanol,
(R)-2-{4-[(2,3-Dihydro-benzo[1,4]dioxin-6-ylmethyl)-amino]-piperidin-1-yl}-1-(6-methoxy-[1,5]naphthyridin-4-yl)-ethanol,
(R)-2-{4-[(Benzo[1,3]dioxol-5-ylmethyl)-amino]-piperidin-1-yl}-1-(6-methoxy-quinolin-4-yl)-ethanol,
6-({1-[(R)-2-Hydroxy-2-(6-methoxy-quinolin-4-yl)-ethyl]-piperidin-4-ylamino}-methyl)-4H-benzo[1,4]oxazin-3-one,
6-({1-[(R)-2-Hydroxy-2-(6-methoxy-quinolin-4-yl)-ethyl]-piperidin-4-ylamino}-methyl)-4H-benzo[1,4]thiazin-3-one,
7-Fluoro-6-({1-[(R)-2-Hydroxy-2-(6-methoxy-quinolin-4-yl)-ethyl]-piperidin-4-ylamino}-methyl)-4H-benzo[1,4]oxazin-3-one,
6-({1-[(R)-2-Hydroxy-2-(6-methoxy-[1,5]naphthyridin-4-yl)-ethyl]-piperidin-4-ylamino}-methyl)-4H-benzo[1,4]oxazin-3-one,
(R)-2-{4-(2,3-Dihydro-[1,4]dioxino[2,3-c]pyridin-7-ylmethyl)amino]piperidin-1-yl}-1-(6-methoxy-[1,5]naphthyridin-4-yl)ethanol,
6-{{1-[(R)-2-Hydroxy-2-(6-methoxy-[1,5]naphthyridin-4-yl)ethyl]piperidin-4-ylamino}methyl}-4H-pyrido[3,2-b][1,4]thiazin-3-one,
7-Bromo-6-{{1-[(R)-2-hydroxy-2-(6-methoxy-[1,5]naphthyridin-4-yl)ethyl]piperidin-4-ylamino}methyl}-4H-pyrido[3,2-b][1,4]thiazin-3-one,
7-{{1-[(R)-2-Hydroxy-2-(6-methoxy-[1,5]naphthyridin-4-yl)ethyl]piperidin-4-ylamino}methyl}-1H-pyrido[3,4-b][1,4]thiazin-2-one
(R)-2-{4-[(3,4-Dihydro-2H-pyrido[3,2-b][1,4]thiazin-6-ylmethyl)-amino]-piperidin-1-yl}-1-(6-methoxy-quinolin-4-yl)-ethanol,
(R)-2-{4-[(3,4-Dihydro-2H-pyrido[3,2-b][1,4]thiazin-6-ylmethyl)-amino]-piperidin-1-yl}-1-(6-methoxy-[1,5]naphthyridin-4-yl)-ethanol,
3-Oxo-3,4-dihydro-2H-pyrido[3,2-b][1,4]thiazine-6-carboxylic acid {1-[(R)-2-hydroxy-2-6-methoxy[1,5]naphthyridin-4-yl)ethyl]piperidin-4-yl}amide, and pharmaceutically acceptable derivatives thereof.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Particular compounds according to the invention include those mentioned in the examples and their pharmaceutically acceptable derivatives.

Pharmaceutically acceptable derivatives of the above-mentioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming esters which break down readily in the human body to leave the parent acid or its salt. Suitable groups of this type include those of part formulae (i), (ii), (iii), (iv) and (v):

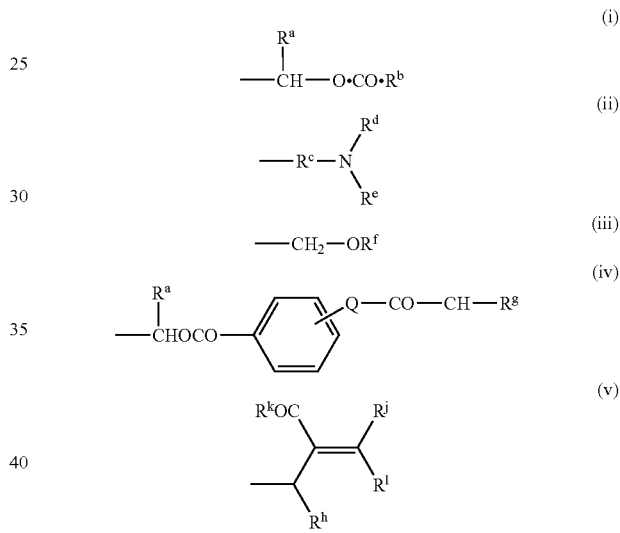

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; $(C_{1-6})$alkoxycarbonyloxy($C_{1-6}$)alkyl groups, such as ethoxycarbonyloxymethyl, α-ethoxycarbonyloxyethyl and propoxycarbonyloxyethyl; di($C_{1-6}$)alkylamino($C_{1-6}$)alkyl especially di($C_{1-4}$)alkylamino($C_{1-4}$)alkyl groups such as dimethylaminomethyl, dimethylaminoethyl, diethylaminomethyl or diethylaminoethyl; 2-(($C_{1-6}$)alkoxycarbonyl)-2-($C_{2-6}$)alkenyl groups such as 2-(isobutoxycarbonyl)pent-2-enyl and 2-(ethoxycarbonyl)but-2-enyl; lactone groups such as phthalidyl and dimethoxyphthalidyl.

A further suitable pharmaceutically acceptable in vivo hydrolysable ester-forming group is that of the formula:

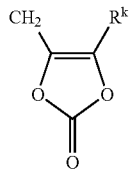

wherein $R^k$ is hydrogen, $C_{1-6}$ alkyl or phenyl.

R is preferably hydrogen.

Compounds of formula (I) may also be prepared as the corresponding N-oxides.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. For example the invention includes compound in which an A-B group CH(OH)—$CH_2$ is in either isomeric configuration, the R-isomer is preferred. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I), and pharmaceutically acceptable derivatives thereof, which process comprises reacting a compound of formula (IV) with a compound of formula (V):

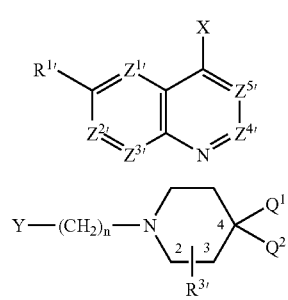

wherein n is as defined in formula (I); $Z^{1'}$, $Z^{2'}$; $Z^{3'}$ $Z^{4'}$, $Z^{5'}$, $R^{1'}$ and $R^{3'}$ are $Z^1$, $Z^2$, $Z^3$, $Z^4$, $Z^5$, $R^1$, and $R^3$ as defined in formula (I) or groups convertible thereto;

$Q^1$ is $NR^{2'}R^{4'}$ or a group convertible thereto wherein $R^{2'}$ and $R^{4'}$ are $R^2$ and $R^4$ as defined in formula (I) or groups convertible thereto and $Q^2$ is H or $R^{3'}$ or $Q^1$ and $Q^2$ together form an optionally protected oxo group;

(i) X is A'-COW, Y is 1 and n is 0;
(ii) X is $CR^6$=$CR^8R^9$, Y is H and n is 0;
(iii) X is oxirane, Y is H and n is 0;
(iv) X is N=C=O and Y is H and n is 0;
(v) one of X and Y is $CO_2R^y$ and the other is $CH_2CO_2P^x$;
(vi) X is $CHR^6R^7$ and Y is C(=O)$R^9$;
(vii) X is $CR^7$=$PR^z_3$ and Y is C(=O)$R^9$ and n=1;
(viii) X is C(=O)$R^7$ and Y is $CR^9$=$PR^z_3$ and n=1;
(ix) Y is COW and X is $NHR^{11'}$, NCO or $NR^{11'}$COW and n=0 or 1 or when n=1 X is COW and Y is $NR^{11'}$, NCO or $NR^{11'}$COW;
(x) X is $NHR^{11'}$ and Y is C(=O)$R^8$ and n=1;
(xi) X is $NHR^{11'}$ and Y is $CR^8R^9W$ and n=1;
(xii) X is $NR^{11'}COCH_2W$ or $NR^{11'}SO_2CH_2W$ and Y is H and n=0;
(xiii) X is $CR^6R^7SO_2W$ and Y is H and n=0;
(xiv) X is W or OH and Y is $CH_2OH$ and n is 1;
(xv) X is $NHR^{11'}$ and Y is $SO_2W$ or X is $NR^{11'}SO_2W$ and Y is H, and n is 0;
(xvi) X is W and Y is $CONHR^{11'}$;

in which W is a leaving group, e.g. halo or imidazolyl; $R^x$ and $R^y$ are ($C_{1-6}$)alkyl; $R^z$ is aryl or ($C_{1-6}$)alkyl; A' and $NR^{11'}$ are A and $NR^{11}$ as defined in formula (I), or groups convertible thereto; and oxirane is:

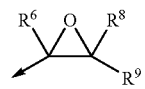

wherein $R^6$, $R^8$ and $R^9$ are as defined in formula (I);
and thereafter optionally or as necessary converting $Q^1$ and $Q^2$, to $NR^{2'}R^{4'}$—; converting A', $Z^{1'}$, $Z^{2'}$, $Z^{3'}$, $Z^{4'}$, $Z^{5'}$, $R^{1'}$, $R^{2'}$, $R^{3'}$, $R^{4'}$ and $NR^{11'}$; to A, $Z^1$, $Z^2$, $Z^3$, $Z^4$, $Z^5$, $R^1$, $R^2$, $R^3$, $R^4$ and $NR^{11}$; converting A-B to other A-B, interconverting $R^1$, $R^2$, $R^3$ and/or $R^4$, and/or forming a pharmaceutically acceptable derivative thereof.

Process variant (i) initially produces compounds of formula (I) wherein A-B is A'-CO.

Process variant (ii) initially produces compounds of formula (I) wherein A-B is $CHR^6$—$CR^8R^9$.

Process variant (iii) initially produces compounds of formula (I) wherein A-B is $CR^6(OH)$—$CR^8R^9$.

Process variant (iv) initially produces compounds of formula (I) where A-B is NH—CO.

Process variant (v) initially produces compounds of formula (I) wherein A-B is CO—$CH_2$ or $CH_2$—CO.

Process variant (vi) initially produces compounds of formula (I) wherein A-B is $CR^6R^7$—$CR^9OH$.

Process variant (vii) and (viii) initially produce compounds of formula (I) wherein A-B is $CR^7$=$CR^9$.

Process variant (ix) initially produces compounds of formula (I) where A-B is CO—$NR^{11}$ or $NR^{11}$—CO.

Process variant (x) initially produces compounds of formula (I) wherein A-B is $NR^{11}$—$CHR^8$.

Process variant (xi) initially produces compounds of formula (I) wherein A-B is $NR^{11'}$—$CR^8R^9$.

Process variant (xii) initially produces compounds of formula (I) where A-B is $NR^{11'}$—CO or $NR^{11'}$—$SO_2$ and n=1.

Process variant (xiii) initially produces compounds of formula (I) where A-B is $CR^6R^7$—$SO_2$.

Process variant (xiv) initially produces compounds of formula (I) wherein A-B is O—$CH_2$.

Process variant (xv) initially produces compounds where AB is $NR^{11}SO_2$.

Process variant (xvi) initially produces compounds of formula (I) where A-B is $NR^{11'}$—CO.

In process variants (i) and (ix) the reaction is a standard amide or urea formation reaction involving e.g.:
1. Activation of a carboxylic acid (e.g. to an acid chloride, mixed anhydride, active ester, O-acyl-isourea or other species), and treatment with an amine (Ogliaruso, M. A.; Wolfe, J. F. in *The Chemistry of Functional Groups* (Ed. Patai, S.) *Suppl. B: The Chemistry of Acid Derivatives, Pt. 1* (John Wiley and Sons, 1979), pp 442–8; Beckwith, A. L. J. in *The Chemistry of Functional Groups* (Ed. Patai, S.) *Suppl. B: The Chemistry of Amides* (Ed. Zabricky, J.) (John Wiley and Sons, 1970), p 73 ff. The acid and amine are preferably reacted in the presence of an activating agent such as 1-(dimethylaminopropyl)-3-ethylcarbodiimide hydrochloride (EDC) or 1-hydroxybenzotriazole (HOBT) or O-(7-azabenzotriazol-1-yl)-N,N,N',N'-tetramethyluronium hexafluorophosphate (HATU); or
2. The specific methods of:
a. in situ conversion of an acid into the amine component by a modified Curtius reaction procedure (Shioiri, T., Murata, M., Hamada, Y., *Chem. Pharm. Bull.* 1987, 35, 2698)
b. in situ conversion of the acid component into the acid chloride under neutral conditions (Villeneuve, G. B.; Chan, T. H., *Tetrahedron. Lett.* 1997, 38, 6489).

A' may be, for example, protected hydroxymethylene.

The process variant (ii) is a standard addition reaction using methods well known to those skilled in the art. The process is preferably carried out in a polar organic solvent e.g. acetonitrile in the presence of an organic base e.g. triethylamine.

In process variant (iii) the coupling may be effected in a suitable solvent such as acetonitrile or dimethylformamide at room temperature in the presence of one equivalent of lithium perchlorate as catalyst (general method of J. E. Chateauneuf et al, *J. Org. Chem.*, 56, 5939–5942, 1991) or more preferably with ytterbium triflate in dichloromethane. In some cases an elevated temperature such as 40–70° C. may be beneficial. Alternatively, the piperidine may be treated with a base, such as one equivalent of butyl lithium, and the resulting salt reacted with the oxirane in an inert solvent such as tetrahydrofuran, preferably at an elevated temperature such as 80° C. Use of a chiral epoxide will afford single diastereomers. Alternatively, mixtures of diastereomers may be separated by preparative HPLC or by conventional resolution through crystallisation of salts formed from chiral acids.

The process variant (iv) is a standard urea formation reaction from the reaction of an isocyanate with an amine and is conducted by methods well known to those skilled in the art (for example see March, J; *Advanced Organic Chemistry*, Edition 3 (John Wiley and Sons, 1985), p802–3). The process is preferably carried out in a polar solvent such as N,N-dimethylformamide.

In process variant (v) the process is two step: firstly a condensation using a base, preferably sodium hydride or alkoxide, sodamide, alkyl lithium or lithium dialkylamide, preferably in an aprotic solvent e.g. ether, THF or benzene; secondly, hydrolysis using an inorganic acid, preferably HCl in aqueous organic solvent at 0–100° C. Analogous routes are described in DE330945, EP31753, EP53964 and H. Sargent, J. Am. Chem. Soc. 68, 2688–2692 (1946). Similar Claisen methodology is described in Soszko et. al., Pr. Kom. Mat. Przyr. Poznan. Tow. Przj. Nauk., (1962), 10, 15.

In process variant (vi) the reaction is carried out in the presence of a base, preferably organometallic or metal hydride e.g. NaH, lithium diisopropylamide or NaOEt, preferably in an aprotic solvent, preferably THF, ether or benzene at −78 to 25° C. (analogous process in Gutswiller et al. (1978) J. Am. Chem. Soc. 100, 576).

In process variants (vii) and (viii) if a base is used it is preferably NaH, KH, an alkyl lithium e.g. BuLi, a metal alkoxide e.g. NaOEt, sodamide or lithium dialkylamide e.g. di-isopropylamide. An analogous method is described in U.S. Pat. No. 3,989,691 and M. Gates et. al. (1970) J. Amer. Chem. Soc., 92, 205, as well as Taylor et al. (1972) JACS 94, 6218.

In process variant (x) where Y is CHO the reaction is a standard reductive alkylation using, e.g., sodium borohydride or sodium triacetoxyborohydride (Gribble, G. W. in *Encyclopedia of Reagents for Organic Synthesis* (Ed. Paquette, L. A.) (John Wiley and Sons, 1995), p 4649).

The process variant (xi) is a standard alkylation reaction well known to those skilled in the art, for example where an alcohol or amine is treated with an alkyl halide in the presence of a base (for example see March, J; *Advanced Organic Chemistry*, Edition 3 (John Wiley and Sons, 1985), p364–366 and p342–343). The process is preferably carried out in a polar solvent such as N,N-dimethylformamide In process variant (xii) the reaction is an alkylation, examples of which are described in J. Med. chem. (1979) 22(10) 1171–6. The compound of formula (IV) maybe prepared from the corresponding compound where X is $NHR^{11'}$ by acylation with an appropriate derivative of the acid $WCH_2COOH$ such as the acid chloride or sulphonation with an appropriate derivative of the sulphonic acid $WCH_2SO_3H$ such as the sulphonyl chloride.

In process variant (xiii) the reaction is a standard sulphonamide formation reaction well known to those skilled in the art. This may be e.g. the reaction of a sulphonyl halide with an amine.

In process variant (xiv) where X is W such as halogen, methanesulphonyloxy or trifluoromethanesulphonyloxy, the hydroxy group in Y is preferably converted to an OM group where M is an alkali metal by treatment of an alcohol with a base. The base is preferably inorganic such as NaH, lithium diisopropylamide or sodium. Where X is OH, the hydroxy group in Y is activated under Mitsunobu conditions (Fletcher et. al. J Chem Soc. (1995), 623). Alternatively the X=O and Y=CH$_2$OH groups can be reacted directly by activation with dichlorocarbodiimide (DCC) (Chem. Berichte 1962, 95, 2997 or Angewante Chemie 1963 75, 377).

In process variant (xv) the reaction is conducted in the presence of an organic base such as triethylamine or pyridine such as described by Fuhrman et. al., J. Amer. Chem. Soc.; 67, 1245, 1945. The X=NR$^{11'}$SO$_2$W or Y=SO$_2$W intermediates can be formed from the requisite amine e.g. by reaction with SO$_2$Cl$_2$ analogously to the procedure described by the same authors Fuhrman et. al., J. Amer. Chem. Soc.; 67, 1245, 1945.

In process variant (xvi) the leaving group W is preferably chloro, bromo or iodo or trifluoromethylsulphonyloxy and the reaction is the palladium catalysed process known as the "Buchwald" reaction (J. Yin and S. L. Buchwald, Org. Lett., 2000, 2, 1101).

Reduction of a carbonyl group A or B to CHOH can be readily accomplished using reducing agents well known to those skilled in the art, e.g. sodium borohydride in aqueous ethanol or lithium aluminium hydride in ethereal solution. This is analogous to methods described in EP53964, U.S. Pat. No. 384,556 and J. Gutzwiller et al, *J. Amer. Chem. Soc.*, 1978, 100, 576.

The carbonyl group A or B may be reduced to $CH_2$ by treatment with a reducing agent such as hydrazine in ethylene glycol, at e.g. 130–160° C., in the presence of potassium hydroxide.

Reaction of a carbonyl group A or B with an organometallic reagent yields a group where $R^6$ or $R^8$ is OH and $R^7$ or $R^9$ is alkyl.

A hydroxy group on A or B may be oxidised to a carbonyl group by oxidants well known to those skilled in the art, for example, manganese dioxide, pyridinium chlorochromate or pyridinium dichromate.

A hydroxyalkyl A-B group $CHR^7CR^9OH$ or $CR^7(OH)CHR^9$ may be dehydrated to give the group $CR^7=CR^9$ by treatment with an acid anhydride such as acetic anhydride.

Methods for conversion of $CR^7=CR^9$ by reduction to $CHR^7CHR^9$ are well known to those skilled in the art, for example using hydrogenation over palladium on carbon as catalyst. Methods for conversion of $CR^7=CR^9$ to give the A-B group $CR^7(OH)CHR^9$ or $CHR^7CR^9OH$ are well known to those skilled in the art for example by epoxidation and subsequent reduction by metal hydrides, hydration, hydroboration or oxymercuration.

An amide carbonyl group may be reduced to the corresponding amine using a reducing agent such as lithium aluminium hydride.

A hydroxy group in A or B may be converted to azido by activation and displacement e.g. under Mitsunobu conditions using hydrazoic acid or by treatment with diphenylphosphorylazide and base, and the azido group in turn may be reduced to amino by hydrogenation.

An example of a group $Q^1$ convertible to $NR^2 R^4$ is $NR^{2'}R^{4'}$ or halogen. Halogen may be displaced by an amine $HNR^{2'}R^{4'}$ by a conventional alkylation.

When $Q^1 Q^2$ together form a protected oxo group this may be an acetal such as ethylenedioxy which can subsequently be removed by acid treatment to give a compound of formula (VI):

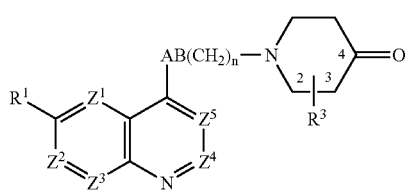

(VI)

wherein the variables are as described for formula (I)

The ketone of formula (VI) is reacted with an amine $HNR^{2'}R^{4'}$ by conventional reductive alkylation as described above for process variant (x).

Examples of groups $Z^{1'}$, $Z^{2'}$, $Z^{3'}$, $Z^{4'}$, $Z^{5'}$ convertible to $Z^1$, $Z^2$, $Z^3$, $Z^4$ and $Z^5$ include $CR^{1a'}$ where $R^{1a'}$ is a group convertible to $R^{1a}$. $Z^{1'}$, $Z^{2'}$, $Z^{3'}$, $Z^{4'}$ and $Z^{5'}$ are preferably $Z^1$, $Z^2$, $Z^3$, $Z^4$ and $Z^5$.

$R^{1a'}$, $R^{1'}$ and $R^{2'}$ are preferably $R^{1a}$, $R^1$ and $R^2$. $R^{1'}$ is preferably methoxy. $R^{2'}$ is preferably hydrogen. $R^{3'}$ is $R^3$ or more preferably hydrogen, vinyl, alkoxycarbonyl or carboxy. $R^{4'}$ is $R^4$ or more preferably H or an N-protecting group such as t-butoxycarbonyl, benzyloxycarbonyl or 9-fluorenylmethyloxycarbonyl.

Conversions of $R^{1'}$, $R^{2'}$, $R^{3'}$ and $R^{4'}$ and interconversions of $R^1$, $R^2$, $R^3$ and $R^4$ are conventional. In compounds which contain an optionally protected hydroxy group, suitable conventional hydroxy protecting groups which may be removed without disrupting the remainder of the molecule include acyl and alkylsilyl groups. N-protecting groups are removed by conventional methods.

For example $R^{1'}$ methoxy is convertible to $R^{1'}$ hydroxy by treatment with lithium and diphenylphosphine (general method described in Ireland et al, *J. Amer. Chem. Soc.*, 1973, 7829) or HBr. Alkylation of the hydroxy group with a suitable alkyl derivative bearing a leaving group such as halide and a protected amino, piperidyl, amidino or guanidino group or group convertible thereto, yields, after conversion/deprotection, $R^1$ alkoxy substituted by optionally N-substituted amino, piperidyl, guanidino or amidino.

$R^3$ alkenyl is convertible to hydroxyalkyl by hydroboration using a suitable reagent such as 9-borabicyclo[3.3.1] nonane, epoxidation and reduction or oxymercuration.

$R^3$ 1,2-dihydroxyalkyl can be prepared from $R^{3'}$ alkenyl using osmium tetroxide or other reagents well known to those skilled in the art (see Advanced Organic Chemistry, Ed. March, J, John Wiley and Sons, 1985, p 732–737 and refs. cited therein) or epoxidation followed by hydrolysis (see Advanced Organic Chemistry, Ed. March, J John Wiley and Sons, 1985, p 332,333 and refs. cited therein).

$R^3$ vinyl can be chain extended by standard homologation, e.g. by conversion to hydroxyethyl followed by oxidation to the aldehyde, which is then subjected to a Wittig reaction.

Opening an epoxide-containing $R^{3'}$ group with cyanide anion yields a $CH(OH)—CH_2CN$ group.

Opening an epoxide-containing $R^{3'}$ group with azide anion yields an azide derivative which can be reduced to the amine. Conversion of the amine to a carbamate is followed by ring closure with base to give the 2-oxo-oxazolidinyl containing $R^3$ group.

Substituted 2-oxo-oxazolidinyl containing $R^3$ groups may be prepared from the corresponding aldehyde by conventional reaction with a glycine anion equivalent, followed by cyclisation of the resulting amino alcohol (M. Grauert et al, *Ann. Chem.*, 1985, 1817; Rozenberg et al, *Angew. Chem. Int. Ed. Engl.*, 1994, 33(1), 91). The resulting 2-oxo-oxazolidinyl group contains a carboxy group which can be converted to other $R^{10}$ groups by standard procedures.

Carboxy groups within $R^3$ may be prepared by Jones' oxidation of the corresponding alcohols $CH_2OH$ using chromium acid and sulphuric acid in water/methanol (E. R. H. Jones et al, *J. Chem. Soc.*, 1946, 39). Other oxidising agents may be used for this transformation such as sodium periodate catalysed by ruthenium trichloride (G. F. Tutwiler et al, *J. Med. Chem.*, 1987, 30(6), 1094), chromium trioxide-pyridine (G. Just et al, *Synth. Commun.*, 1979, 9(7), 613), potassium permanganate (D. E. Reedich et al, *J. Org. Chem.*, 1985, 50(19), 3535), and pyridinium chlorochromate (D. Askin et al, *Tetrahedion Lett.*, 1988, 29(3), 277).

The carboxy group may alternatively be formed in a two stage process, with an initial oxidation of the alcohol to the corresponding aldehyde using for instance dimethyl sulphoxide activated with oxalyl chloride (N. Cohen et al, *J. Am. Chem. Soc.*, 1983, 105, 3661) or dicyclohexylcarbodiimide (R. M. Wengler, *Angew. Chim. Int. Ed. Eng.*, 1985, 24(2), 77), or oxidation with tetrapropylammonium perruthenate (Ley et al, *J. Chem. Soc. Chem Commun.*, 1987, 1625). The aldehyde may then be separately oxidised to the corresponding acid using oxidising agents such as silver (II) oxide (R. Grigg et al, J. Chem. Soc. Perkin1, 1983, 1929), potassium permanganate (A. Zurcher, *Helv. Chim. Acta.*, 1987, 70 (7), 1937), sodium periodate catalysed by ruthenium trichloride (T. Sakata et al, *Bull: Chem. Soc. Jpn.*, 1988, 61(6), 2025), pyridinium chlorochromate (R. S.

Reddy et al, *Synth. Commun.*, 1988, 18(51), 545) or chromium trioxide (R. M. Coates et al, *J. Am. Chem. Soc.*, 1982, 104, 2198).

An $R^3$ $CO_2H$ group may also be prepared from oxidative cleavage of the corresponding diol, $CH(OH)CH_2OH$, using sodium periodate catalysed by ruthenium trichloride with an acetontrile-carbontetrachloride-water solvent system (V. S. Martin et al, *Tetrahedron Letters*, 1988, 29(22), 2701).

Other routes to the synthesis of carboxy groups within $R^3$ are well known to those skilled in the art.

$R^3$ groups containing a cyano or carboxy group may also be prepared by conversion of an alcohol to a suitable leaving group such as the corresponding tosylate by reaction with para-toluenesulphonyl chloride (M. R. Bell, *J. Med. Chem.*, 1970, 13, 389), or the iodide using triphenylphosphine, iodine, and imidazole (G. Lange, *Synth. Commun.*, 1990, 20, 1473). The second stage is the displacement of the leaving group with cyanide anion (L. A. Paquette et al, *J. Org. Chem.*, 1979, 44(25), 4603; P. A. Grieco et al, *J. Org. Chem.*, 1988, 53(16), 3658. Finally acidic hydrolysis of the nitrile group gives the desired acids (H. Rosemeyer et al, Heterocycles, 1985, 23 (10), 2669). The hydrolysis may also be carried out with base e.g. potassium hydroxide (H. Rapoport, *J. Org. Chem.*, 1958, 23, 248) or enzymatically (T. Beard et al, *Tetrahedron Asymmetry*, 1993, 4 (6), 1085).

$R^3$ cis or trans hydroxy may be introduced by the methods of van Deale et al., *Drug Development Research* 8:225–232 (1986) or *Heterocycles* 39(1), 163–170 (1994). For trans hydroxy, a suitable method converts N-protected tetrahydropyridine to the epoxide by treatment with metachloroperbenzoic acid, followed by opening of the epoxide with a suitable amine $NR^{2'}R^{4'}$.

Other functional groups in $R^3$ may be obtained by conventional conversions of hydroxy, carboxy or cyano groups.

Tetrazoles are conveniently prepared by reaction of sodium azide with the cyano group (e.g. F. Thomas et al, *Bioorg. Med. Chem. Lett.*, 1996, 6(6), 631; K. Kubo et al, *J. Med. Chem.*, 1993, 36, 2182) or by reaction of azidotri-n-butyl stannane with the cyano group followed by acidic hydrolysis (P. L. Ornstein, *J. Org. Chem.*, 1994, 59, 7682 and *J. Med. Chem*, 1996, 39 (11), 2219).

The 3-hydroxy-3-cyclobutene-1,2-dion-4-yl group (e.g. R. M. Soll, *Bioorg. Med. Chem. Lett.*, 1993, 3(4), 757 and W. A. Kinney, *J. Med. Chem.*, 1992, 35(25), 4720) can be prepared by the following sequence:—(1) a compound where $R^3$ is $(CH_2)_nCHO$ (n=0, 1, 2) is treated with triethylamine, carbon tetrabromide-triphenylphosphine to give initially $(CH_2)_nCH=CHBr$; (2) dehydrobromination of this intermediate to give the corresponding bromoethyne derivative $(CH_2)_nC\equiv CBr$ (for this 2 stage sequence see D. Grandjean et al, *Tetrahedron Lett.*, 1994, 35(21), 3529); (3) palladium-catalysed coupling of the bromoethyne with 4-(1-methylethoxy)-3-(tri-n-butylstannyl)cyclobut-3-ene-1,2-dione (Liebeskind et al, *J. Org. Chem.*, 1990, 55, 5359); (4) reduction of the ethyne moiety to —$CH_2CH_2$— under standard conditions of hydrogen and palladium on charcoal catalysis (see Howard et al, *Tetrahedron*, 1980, 36, 171); and finally (4) acidic hydrolysis of the methyl ethoxyester to generate the corresponding 3-hydroxy-3-cyclobutene-1,2-dione group (R. M. Soll, *Bioorg. Med. Chem. Lett.*, 1993, 3(4), 757).

The tetrazol-5-ylaminocarbonyl group may be prepared from the corresponding carboxylic acid and 2-aminotetrazole by dehydration with standard peptide coupling agents such as 1,1'-carbonyldiimidazole (P. L. Ornstein et al, *J. Med Chem*, 1996, 39(11), 2232).

The alkyl- and alkenyl-sulphonylcarboxamides are similarly prepared from the corresponding carboxylic acid and the alkyl- or alkenyl-sulphonamide by dehydration with standard peptide coupling agents such as 1,1'-carbonyldiimidazole (P. L. Ornstein et al, *J. Med. Chem.*, 1996, 39(11), 2232).

The hydroxamic acid groups are prepared from the corresponding acids by standard amide coupling reactions e.g. N. R. Patel et al, *Tetrahedron*, 1987, 43(22), 5375.

2,4-Thiazolidinedione groups may prepared from the aldehydes by condensation with 2,4-thiazolidinedione and subsequent removal of the olefinic double bond by hydrogenation.

The preparation of 5-oxo-1,2,4-oxadiazoles from nitrites is decribed by Y. Kohara et al, *Bioorg. Med. Chem. Lett.*, 1995, 5(17), 1903.

1,2,4-Triazol-5-yl groups may be prepared from the corresponding nitrile by reaction with an alcohol under acid conditions followed by reaction with hydrazine and then an $R^{10}$-substituted activated carboxylic acid (see J. B. Polya in "Comprehensive Heterocyclic Chemistry" Edition 1, p762, Ed A. R. Katritzky and C. W. Rees, Pergamon Press, Oxford, 1984 and J. J. Ares et al, *J. Heterocyclic Chem.*, 1991, 28(5), 1197).

Other substituents on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group or oxidation as appropriate or reaction with an activated acid, isocyanate or alkoxyisocyanate. Primary and secondary hydroxy groups can be oxidised to an aldehyde or ketone respectively and alkylated with a suitable agent such as an organometallic reagent to give a secondary or tertiary alcohol as appropriate. A carboxylate group may be converted to an hydroxymethyl group by reduction of an ester of this acid with a suitable reducing agent such as lithium aluminium hydride.

An $NH_2$ substituent on piperidine is converted to $NR^2R^4$ by conventional means such as amide or sulphonamide formation with an acyl derivative $R^5COW$ or $R^5SO_2W$, for compounds where U is CO or $SO_2$ or, where U is $CH_2$, by alkylation with an alkyl halide $R^5CH_2$-halide in the presence of base, acylation/reduction with an acyl derivative $R^5COW$ or reductive alkylation with an aldehyde $R^5CHO$.

Where one of $R^3$ and $R^6$, $R^7$, $R^8$ or $R^9$ contains a carboxy group and the other contains a hydroxy or amino group they may together form a cyclic ester or amide linkage. This linkage may form spontaneously during coupling of the compound of formula (IV) and the piperidine moiety or in the presence of standard peptide coupling agents.

It will be appreciated that under certain circumstances interconvertions may interfere, for example, A or B hydroxy groups in A or B and the piperidine substituent $NH_2$ will require protection e.g. as a carboxy- or silyl-ester group for hydroxy and as an acyl derivative for piperidine $NH_2$, during conversion of $R^{1'}$, $R^{2'}$, $R^{3'}$ or $R^{4'}$, or during the coupling of the compounds of formulae (IV) and (V).

Compounds of formulae (IV) and (V) are known compounds, (see for example Smith et al, *J. Amer. Chem. Soc.*, 1946, 68, 1301) or prepared analogously.

Compounds of formula (IV) where X is $CR^6R^7SO_2W$ may be prepared by a route analogous to that of Ahmed El Hadri et al, *J. Heterocyclic Chem.*, 1993, 30(3), 631. Thus compounds of formula (IV) where X is $CH_2SO_2OH$ may be prepared by reacting the corresponding 4-methyl compound with N-bromosuccinimide, followed by treatment with sodium sulfite. The leaving group W may be converted to another leaving group W, e.g. a halogen group, by conventional methods.

The isocyanate of formula (IV) may be prepared conventionally from a 4-amino derivative such as 4-amino-quinoline, and phosgene, or phosgene equivalent (eg triphosgene) or it may be prepared more conveniently from a 4-carboxylic acid by a "one-pot" Curtius Reaction with diphenyl phosphoryl azide (DPPA) [see T. Shiori et al. *Chem. Pharm. Bull.* 35, 2698–2704 (1987)].

The 4-amino derivatives are commercially available or may be prepared by conventional procedures from a corresponding 4-chloro or 4-trifluoromethanesulphonate derivative by treatment with ammonia (O. G. Backeberg et. al., J. Chem Soc., 381, 1942) or propylamine hydrochloride (R. Radinov et. al., Synthesis, 886, 1986).

4-Alkenyl compounds of formula (IV) may be prepared by conventional procedures from a corresponding 4-halogeno-derivative by e.g. a Heck synthesis as described in e.g. *Organic Reactions*, 1982, 27, 345.

4-Halogeno derivatives of compounds of formula (IV) are commercially available, or may be prepared by methods known to those skilled in the art. A 4-chloroquinoline is prepared from the corresponding quinolin-4-one by reaction with phosphorus oxychloride ($POCl_3$) or phosphorus pentachloride, $PCl_5$. A 4-chloroquinazoline is prepared from the corresponding quinazolin-4-one by reaction with phosphorus oxychloride ($POCl_3$) or phosphorus pentachloride, $PCl_5$. A quinazolinone and quinazolines may be prepared by standard routes as described by T. A. Williamson in *Heterocyclic Compounds*, 6, 324 (1957) Ed. R. C. Elderfield.

4-Carboxy derivatives of compounds of formula (IV) are commercially available or may be prepared by conventional procedures for preparation of carboxy heteroaromatics well known to those skilled in the art. For example, quinazolines may be prepared by standard routes as described by T. A. Williamson in *Heterocyclic Compounds*, 6, 324 (1957) Ed. R. C. Elderfield. These 4-carboxy derivatives may be activated by conventional means, e.g. by conversion to an acyl halide or anhydride.

Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

A 4-oxirane derivative of compounds of formula (IV) is conveniently prepared from the 4-carboxylic acid by first conversion to the acid chloride with oxalyl chloride and then reaction with trimethylsilyldiazomethane to give the diazoketone derivative. Subsequent reaction with 5M hydrochloric acid gives the chloromethylketone. Reduction with sodium borohydride in aqueous methanol gives the chlorohydrin which undergoes ring closure to afford the epoxide on treatment with base, e.g. potassium hydroxide in ethanol-tetrahydrofuran.

Alternatively and preferably, 4-oxirane derivatives can be prepared from bromomethyl ketones which can be obtained from 4-hydroxy compounds by other routes well known to those skilled in he art. For example, hydroxy compounds can be converted to the corresponding 4-trifluoromethane-sulphonates by reaction with trifluoromethanesulphonic anhydride under standard conditions (see K. Ritter, Synthesis, 1993, 735). Conversion into the corresponding butyloxyvinyl ethers can be achieved by a Heck reaction with butyl vinyl ether under palladium catalysis according to the procedure of W. Cabri et al, J. Org. Chem, 1992, 57 (5), 1481. (Alternatively, the same intermediates can be attained by Stille coupling of the trifluoromethanesulphonates or the analaogous chloro derivatives with (1-ethoxyvinyl)tributyl tin, T. R. Kelly, J. Org. Chem., 1996, 61, 4623.) The alkyloxyvinyl ethers are then converted into the corresponding bromomethylketones by treatment with N-bromosuccinimide in aqueous tetrahydrofuran in a similar manner to the procedures of J. F. W. Keana, J. Org. Chem., 1983, 48, 3621 and T. R. Kelly, J. Org. Chem., 1996, 61, 4623.

The 4-hydroxyderivatives can be prepared from an aminoaromatic by reaction with methylpropiolate and subsequent cyclisation, analogous to the method described in N. E. Heindel et al, J. Het. Chem., 1969, 6, 77. For example, 5-amino-2-methoxy pyridine can be converted to 4-hydroxy-6-methoxy-[1,5]naphthyridine using this method.

If a chiral reducing agent such as (+) or (−)-B-chlorodi-isopinocamphenylborane ['DIP-chloride'] is substituted for sodium borohydride, the prochiral chloromethylketone is converted into the chiral chlorohydrin with ee values generally 85–95% [see C. Bolm et al, *Chem. Ber.* 125, 1169–1190, (1992)]. Recrystallisation of the chiral epoxide gives material in the mother liquor with enhanced optical purity (typically ee 95%).

The (R)-epoxide, when reacted with a piperidine derivative gives ethanolamine compounds as single diastereomers with (R)-stereochemistry at the benzylic position.

Alternatively, the epoxide may be prepared from the 4-carboxaldehyde by a Wittig approach using trimethylsulfonium iodide [see G. A. Epling and K-Y Lin, *J. Het. Chem.*, 1987, 24, 853–857], or by epoxidation of a 4-vinyl derivative.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5]naphthyridine-3-carboxylic acid, J. T. Adams et al., *J. Amer. Chem. Soc.*, 1946, 68, 1317). A 4-hydroxy-[1,5]naphthyridine can be converted to the 4-chloro derivative by heating in phosphorus oxychloride, or to the 4-methanesulphonyloxy or 4-trifluoromethanesulphonyloxy derivative by reaction with methanesulphonyl chloride or trifluoromethanesulphonic anhydride, respectively, in the presence of an organic base. A 4-amino 1,5-naphthyridine can be obtained from the 4-chloro derivative by reaction with n-propylamine in pyridine.

Similarly, 6-methoxy-1,5-naphthyridine derivatives can be prepared from 3-amino-6-methoxypyridine.

1,5-Naphthyridines may be prepared by other methods well known to those skilled in the art (for examples see P. A. Lowe in "Comprehensive Heterocyclic Chemistry" Volume 2, p581–627, Ed A. R. Katritzky and C. W. Rees, Pergamon Press, Oxford, 1984).

The 4-hydroxy and 4-amino-cinnolines may be prepared following methods well known to those skilled in the art [see A. R. Osborn and K. Schofield, *J. Chem. Soc.* 2100 (1955)]. For example, a 2-aminoacetopheneone is diazotised with sodium nitrite and acid to produce the 4-hydroxycinnoline with conversion to chloro and amino derivatives as described for 1,5-naphthyridines.

For compounds of formula (V), suitable amines may be prepared from the corresponding 4-substituted piperidine acid or alcohol. In a first instance, an N-protected piperidine containing an acid bearing substituent, can undergo a Curtius rearrangement and the intermediate isocyanate can be converted to a carbamate by reaction with an alcohol. Conversion to the amine may be achieved by standard methods well known to those skilled in the art used for amine protecting group removal. For example, an acid substituted N-protected piperidine can undergo a Curtius rearrangement e.g. on treatment with diphenylphosphoryl azide and heating, and the intermediate isocyanate reacts in the presence of 2-trimethylsilylethanol to give the trimethylsilylethylcarbamate (T. L. Capson & C. D. Poulter, *Tetrahedron Lett.*, 1984, 25, 3515). This undergoes cleavage on treatment with tetrabutylammonium fluoride to give the 4-amine substituted N-protected piperidine.

In a second instance, an N-protected piperidine containing an alcohol bearing substituent undergoes a Mitsunobu reaction (for example as reviewed in Mitsunobu, *Synthesis*, (1981), 1), for example with succinimide in the presence of diethyl azodicarboxylate and triphenylphosphine to give the phthalimidoethylpiperidine. Removal of the phthaloyl group, for example by treatment with methylhydrazine, gives the amine of formula (V).

$R^5CH_2$-halides, acyl derivative $R^5COW$ and $R^5SO_2W$ or aldehydes $R^5CHO$ are commercially available or are prepared conventionally. The aldehydes may be prepared by partial reduction of the $R^5$-ester with lithium aluminium hydride or di-isobutylaluminium hydride or more preferably by reduction to the alcohol, with lithium aluminium hydride or sodium borohydride or lithium triethylborohydride (see *Reductions by the Alumino- and Borohydrides in Organic Synthesis*, 2nd ed., Wiley, N.Y., 1997; *JOC*, 3197, 1984; *Org. Synth. Coll.*, 102, 1990; 136, 1998; *JOC*, 4260, 1990; TL, 995, 1988; *JOC*, 1721, 1999; *Liebigs Ann./Recl.*, 2385, 1997; *JOC*, 5486, 1987), followed by oxidation to the aldehyde with manganese (II) dioxide. The aldehydes may also be prepared from carboxylic acids in two stages by conversion to a mixed carbonate for example by reaction with isobutyl chloroformate followed by reduction with sodium borohydride (R. J. Alabaster et al., Synthesis, 598, 1989) to give the hydroxymethyl substituted heteroaromatic or aromatic and then oxidation with a standard oxidising agent such as pyridinium dichromate or manganese (II) dioxide. Acyl derivative $R^5COW$ may be prepared by activation of the $R^5$-ester. $R^5CH_2$-halides such as bromides may be prepared from the alcohol $R^5CH_2OH$ by reaction with phosphorus tribromide in DCM/triethylamine.

Alternatively the aldehyde $R^5CHO$ and sulphonic acid derivative $R^5SO_2W$ may be generated by treatment of the $R^5H$ heterocycle with suitable reagents. For example benzoxazinones, or more preferably their N-methylated derivatives can be formylated with hexamine in either trifluoroacetic acid or methanesulfonic acid, in a modified Duff procedure [O. I. Petrov et al. *Collect. Czech. Chem. Commun.* 62, 494–497 (1997)]. 4-Methyl-4H-benzo[1,4]oxazin-3-one may also be formylated using dichloromethyl methyl ether and aluminium chloride giving exclusively the 6-formyl derivative. Reaction of a $R^5H$ heterocycle with chlorosulphonic acid gives the sulphonic acid derivative (by methods analogous to Techer et. al., C. R. Hebd. *Seances Acad. Sci. Ser. C*; 270, 1601, 1970).

The aldehyde $R^5CHO$ may be generated by conversion of an $R^5$halogen or $R^5$trifluoromethane sulphonyloxy derivative into an olefin with subsequent oxidative cleavage by standard methods. For example, reaction of a bromo derivative under palladium catalysis with trans-2-phenylboronic acid under palladium catalysis affords a styrene derivative which upon ozonolysis affords the required $R^5CHO$ (Stephenson, G. R., Adv. Asymmetric Synth. (1996), 275–298. Publisher: Chapman & Hall, London).

$R^5$ heterocycles are commercially available or may be prepared by conventional methods. For example where a benzoxazinone is required, a nitrophenol may be alkylated with for example ethyl bromoacetate and the resulting nitro ester reduced with Fe in acetic acid (alternatively Zn/AcOH/ HCl or $H_2$ Pd/C or $H_2$ Raney Ni). The resulting amine will undergo spontaneous cyclisation to the required benzoxazinone. Alternatively a nitrophenol may be reduced to the aminophenol, which is reacted with chloroacetyl chloride [method of X. Huang and C. Chan, *Synthesis* 851 (1994)] or ethyl bromoacetate in DMSO [method of Z. Moussavi et al. *Eur. J. Med. Chim. Ther.* 24, 55–60 (1989)]. The same general routes can be applied to prepare benzothiazinones [See for example F. Eiden and F. Meinel, Arch. Pharm. 312, 302–312 (1979), H. Fenner and R Grauert *Liebigs. Ann. Chem.* 193–313 (1978)]]. A variety of routes are available to prepare aza analogues of benzothiazinones via the key corresponding aldehydes. For instance, 2-oxo-2,3-dihydro-1H-pyrido[3,4-b][1,4]thiazine-7-carbaldehyde may be accessed from 5-fluoro-2-picoline (E. J. Blanz, F. A. French, J. R. DoAmaral and D. A. French, J. Med. Chem. 1970, 13, 1124–1130) by constructing the thiazinone ring onto the pyridyl ring then functionalising the methyl substituent, as described in the Examples. The dioxin analogue of this aza substitution patern, 2,3-dihydro-[1,4]dioxino[2,3-c]pyridine-7-carbaldehyde is accessible from Kojic acid by aminolysis from pyrone to pyridone then annelating the dioxin ring, again as described in the subsequent experimental data. Other aza substitution patterns with pyridothiazin-3-one, pyridooxazin-3-one, and pyridodioxin ring systems are also accessible, again as descibed in the Examples. Ortho-aminothidphenols may be conveniently prepared and reacted as their zinc complexes [see for example V. Taneja et al *Chem. Ind.* 187 (1984)]. Benzoxazolones may be prepared from the corresponding aminophenol by reaction with carbonyl diimidazole, phosgene ot triphosgene. Reaction of benzoxazolones with diphosporus pentasulfide affords the corresponding 2-thione. Thiazines and oxazines can be prepared by reduction of the corresponding thiazinone or oxazinone with a reducing agent such as lithium aluminium hydride.

The amines $R^{2'}R^{4'}NH$ are available commercially or prepared conventionally. For example amines $R^5CH_2NH_2$ may be prepared from a bromomethyl derivative by reaction with sodium azide in dimethylformamide (DMF), followed by hydrogenation of the azidomethyl derivative over palladium-carbon. An alternative method is to use potassium phthalimide/DMF to give the phthalimidomethyl derivative, followed by reaction with hydrazine in DCM to liberate the primary amine.

Conversions of $R^{1a'}$, $R^{1'}$, $R^{2'}$, $R^{3'}$ and $R^{4'}$ may be carried out on the intermediates of formulae (IV), and (V) prior to their reaction to produce compounds of formula (I) in the same way as described above for conversions after their reaction.

Further details for the preparation of compounds of formula (I) are found in the examples.

The compounds of formula (I) may be prepared singly or as compound libraries comprising at least 2, for example 5 to 1,000 compounds, and more preferably 10 to 100 compounds of formula (I). Libraries of compounds of formula (I)

may be prepared by a combinatorial "split and mix" approach or by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable derivatives thereof.

Novel intermediates of formulae (IV) and (V) are also part of this invention.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable derivative thereof is administered in the above-mentioned dosage range.

The compound of formula (I) may be the sole therapeutic agent in the compositions of the invention or a combination with other antibacterials. If the other antibacterial is a β-lactam then a β-lactamase inhibitor may also be employed.

Compounds of formula (I) are active against a wide range of organisms including both Gram-negative and Gram-positive organisms.

All publications, including but not limited to patents and patent applications, cited in this specification are herein incorporated by reference as if each individual publication were specifically and individually indicated to be incorporated by reference herein as though fully set forth.

The following examples illustrate the preparation of certain compounds of formula (I) and the activity of certain compounds of formula (I) against various bacterial organisms.

Abbreviations in the examples:

RT=room temperature

ES=Electrospray mass spec.

LCMS=Liquid chromatography mass spec.

APCI+=Atmospheric pressure chemical ionisation mass spec

EXAMPLES

Example 1

(R)-2-{4-[(2,3-Dihydro-benzo[1,4]dioxin-6-ylm-ethyl)-amino]-piperidin-1-yl}-1-(6-methoxy-quino-lin-4-yl)-ethanol dioxalate

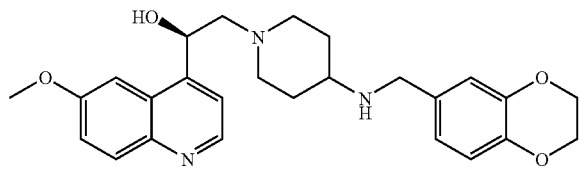

(a) 6-Methoxyquinoline-4-carboxylic acid

The title compound was prepared by modification of the procedure described by W. E. Doering and J. D. Chanley, *J. Amer. Chem. Soc.*, 1946, 68, 586. A mixture of quinone (derived from quinine by reaction with potassium tert-butoxide and benzophenone in toluene) (225 g, 0.70 mol), tert-butanol (1 liter) and water (10 ml) was treated with potassium t-butoxide (170 g, 1.5 mol). The mixture was stirred at 30° C., while air was bubbled through for 3 days. The mixture was diluted with diethyl ether and water and the layers separated. The aqueous phase was extracted with ethyl acetate. The combined diethyl ether and ethyl acetate extracts were dried over magnesium sulfate and evaporated to give recovered starting material (approximately 100 g). The aqueous phase was acidified to pH5 with 5M hydrochloric acid. The precipitate was collected by filtration, washed with water and methanol, then dried to give 6-methoxyquinoline-4-carboxylic acid as a yellow solid (64.6 g, 46%).

δH (d-6 DMSO) 1.94–1.52 (2H, m), 2.38–2.15 (3H, m), 2.70 (1H, m), 3.37–2.92 (5H, m), 5.34–5.06 (2H, m), 6.23–5.95 (1H, m)

(b) [R]-2-(6-Methoxyquinolin-4-yl)oxirane

A solution of 6-methoxyquinoline-4-carboxylic acid (10 g) in dichloromethane was heated under reflux with oxalyl chloride (5 ml) and dimethylformamide (2 drops) for 1 hour and evaporated to dryness. The residue, in dichloromethane (100 ml) was treated with a 2M solution of trimethylsilyl-diazomethane in hexane (50 ml) and stirred at room temperature for 18 hours. 5M Hydrochloric acid (150 ml) was added and the solution was stirred at room temperature for 3 hours. It was basified with sodium carbonate solution, extracted with ethyl acetate and chromatographed on silica gel eluting with ethyl acetate-hexane to give the chloromethyl ketone (4.2 g). A batch of the chloromethyl ketone (20 g) was reduced with (+)-B-chlorodiisopinocamphenylborane (40 g) in dichloromethane (400 ml) at room temperature for 18 hours followed by treatment with diethanolamine (30 g) for 3 hours. The product was chromatographed on silica gel eluting with ethyl acetate-hexane to give the chloroalcohol (16.8 g), which was dissolved in tetrahydrofuran (100 ml) and reacted with sodium hydroxide (2.6 g) in water (13 ml) for 1.5 hours. The reaction mixture was evaporated to dryness and chromatographed on silica gel eluting with ethyl acetate—hexane to give the title compound as a solid (10.4 g) (84% ee by chiral HPLC).

Recrystallisation from ether-pentane gave mother-liquor (7.0 g) (90% ee).

MS (+ve ion electrospray) m/z 202 (N+)

The absolute stereochemistry was defined to be (R) by an NMR study on the Mosher's esters derived from the product obtained by reaction with 1-t-butylpiperazine.

(c) 4-tert-Butoxycarbonylamino-1-[2-(R)-hydroxy-2-(6-methoxyquinolin-4-yl)]ethylpiperidine.

To a stirred solution of [R]-2-(6-methoxyquinolin-4-yl)oxirane (Example 1b) (8.07 g, 40.3 mmol) and lithium perchlorate (4.44 g, 40.3 mmol) in anhydrous N,N-dimethylformamide (100 mL) was added 4-tert-butoxycarbonylaminopiperidine hydrochloride (11.0 g, 45.7 mmol) and potassium carbonate (6.72, 48.4 mmol). The mixture was heated at 90° C. for 26 hours, then cooled, filtered and evaporated. The residue was dissolved in ethyl acetate, washed with water, dried and evaporated. The crude product was chromatographed on silica gel eluted with 2–5% methanol/dichloromethane to give a gum (11.11 g).

MS (+ve ion electrospray) m/z 402 (MH+).

(d) (R)-2-(4-Amino-piperidin-1-yl)-1-(6-methoxy-quinolin-4-yl)-ethanol

The tert-butoxycarbonylamino compound (1c) (11.11 g, 27.7 mmol) was dissolved in dichloromethane (30 mL), cooled in ice and treated with trifluoroacetic acid (30 mL). The solution was stirred at room temperature for 1.5 hours, then evaporated in vacuo. After addition of toluene (50 mL) and re-evaporation, the residue was treated with a 4M solution of hydrogen chloride in 1,4-dioxan (30 mL). The resulting solid was triturated, filtered off and washed with ether. This was then recrystallised by dissolving in hot methanol, concentrating the solution and diluting with dichloromethane, to give the trihydrochloride salt (9.4 g). This was dissolved in water, basified to pH9 and evaporated to dryness. The residue was extracted several times with 10% methanol/dichloromethane (total 600 mL). The extracts were filtered and evaporated to give the free base as a semi-solid foam (6.45 g).

MS (+ve ion electrospray) m/z 302 (MH+)

(e) Title Compound

A solution of (1d) (100 mg; 0.33 mmol) in dichloromethane (3 ml) and methanol (1 ml) was treated with activated 3A molecular sieves (1 g) and 2,3-dihydrobenzo[1,4]dioxine-6-carboxaldehyde (54 mg, 0.33 mmol). The resulting solution was stirred at room temperature for 5 hours and then sodium borohydride (25 mg, 0.66 mmol) was added. The resulting slurry was stirred at room temperature for a further 10 hours. The reaction mixture was quenched by the addition of water (2 ml) and the volatiles removed in vacuo. The residue was partitioned between ethyl acetate (2×100 ml) and brine (20 ml). The organic phases were combined and dried over magnesium sulphate. The volatiles were again removed under reduced pressure and the resulting oil was subjected to purification on silica gel using a methanol and dichloromethane gradient affording the free base of the title compound as a colourless oil (35 mg, 23%)

δH (CDCl₃): 1.40–2.65 (8H, m), 2.79–2.68 (2H, m), 3.20–3.35 (1H, m), 3.72 (2H, s), 3.93 (3H, s), 4.25 (4H, s), 5.30–5.45 (1H, dd), 6.76–6.85 (3H, m), 7.18 (1H, d), 7.34–7.39 (1H, dd), 7.64 (1H, d), 8.03 (1H, d), 8.76 (1H, d).

MS (+ve ion electrospray) m/z 450 (MH+).

A solution of the oil (35 mg) in dichloromethane (1 ml) was added to oxalic acid (14 mg) in diethyl ether (10 ml) to generate the dioxalate salt. The title compound was isolated by centrifugation, washing with diethyl ether and subsequent drying in vacuo.

Example 2

(R)-2-{4-[(2,3-Dihydro-benzo[1,4]dioxin-6-ylmethyl)-amino]-piperidin-1-yl}-1-(6-methoxy-[1,5]naphthyridin-4-yl)-ethanol dioxalate

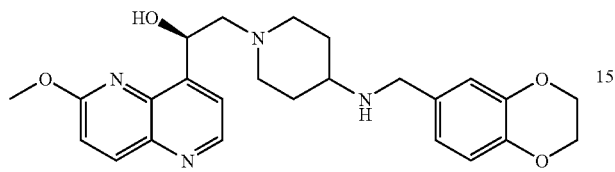

(a) 6-Methoxy-1H-[1,5]naphthyridin-4-one

5-Amino-2-methoxypyridine (55 g, 0.44 mol) in methanol (1000 ml) with methyl propiolate (40 ml, 0.44 mol) was stirred for 48 hours, then evaporated and the product purified by chromatography on silica gel (dichloromethane) followed by recrystallisation from dichloromethane-hexane (44.6 g, 48%). The unsaturated ester (10.5 g, 0.05 mol) in warm Dowtherm A (50 ml) was added over 3 minutes to refluxing Dowtherm A, and after a further 20 minutes at reflux the mixture was cooled and poured into ether. The precipitate was filtered to give a white solid (6.26 g, 70%).

(b) 1,1,1-Trifluoro-methanesulfonic acid 6-methoxy-[1,5]naphthyridin-4-yl ester The naphthyridine (2a) (10 g, 0.057 mol) in dichloromethane (200 ml) containing 2,6-lutidine (9.94 ml, 0.086 mol) and 4-dimethylaminopyridine (0.07 g, 0.0057 mol) was cooled in ice and treated with trifluoromethanesulfonic anhydride (10.5 ml, 0.063 mol). After stirring for 2.5 hours the mixture was washed with saturated ammonium chloride solution, dried, evaporated and purified on silica (dichloromethane).

(c) Bromomethyl-(6-methoxy-[1,5]-naphthyridin-4-yl)-ketone

The triflate (2b) (13.2 g, 0.044 mol) in N,N-dimethylformamide (200 ml) with triethylamine (12 ml, 0.086 mol), butyl vinyl ether (22 ml, 0.17 mol), palladium (II) acetate (0.97 g, 0.0044 mol) and 1,3-bis(diphenylphosphino)propane (1.77 g, 0.0044 mol) was heated at 60° C. for 3 hours then evaporated and chromatographed on silica gel (dichloromethane) to give a yellow solid (10.7 g, 95%). This was dissolved in tetrahydrofuran (250 ml) and water (40 ml) then treated with N-bromosuccinimide (7.4 g, 0.042 mol) for 1 hour. Evaporation and chromatography on silica gel (dichloromethane) gave the ketone (10.42 g, 98%).

(d) (R)-2-Bromo-1-(6-methoxy-[1,5]-naphthyridin-4-yl)ethanol

The bromomethyl ketone (2c) (6.6 g, 0.023 mol) in toluene was treated with (+)-B-chlorodiisopinocamphenylborane ((+)-DIP-chloride) (12 g, 0.037 mol) and stirred overnight, then diethanolamine (15 g, 0.14 mol) added and the mixture stirred for 3 hours, filtered and evaporated. Chromatography on silica gel (ethyl acetate-hexane) gave a white solid (4.73 g, 73%).

(e) (R)-2-(6-Methoxy-[1,5]-naphthyridin-4-yl)oxirane

The alcohol (2d) (4.8 g, 0.017 mol) in methanol (20 ml) was stirred with potassium carbonate (2.6 g, 0.019 mol) for 1 hour, then evaporated and chromatographed on silica gel (ethyl acetate-hexane-dichloromethane) to give a solid (3.14 g, 92%), (91% ee by chiral HPLC).

MS (+ve ion electrospray) m/z 203 (MH+).

(f) (R)-2-(4-Amino-piperidin-1-yl)-1-(6-methoxy-[1,5]naphthyridin-4-yl)-ethanol This was prepared in similar overall yield from oxirane (2e) by the method of Example (1c,d).

MS (+ve ion electrospray) m/z 303 (MH+).

(g) Title Compound

This was prepared from amine (2f) and 2,3-dihydro-benzo[1,4]dioxine-6-carboxaldehyde by the same reductive alkylation procedure as for Example 1, giving the free base of the title compound as an oil (223 mg, 49%).

δH (CDCl$_3$): 1.60 (2H, m), 2.05 (2H, m), 2.25 (1H, m), 2.45 (2H, m), 2.70 (1H, m), 2.85 (1H, m), 3.10 (1H, m), 3.30 (1H, m), 3.75 (2H, s), 4.00 (3H, s), 4.25 (4H, s), 5.75 (1H, dd), 6.80–6.90 (3H, m), 7.10 (1H, d), 7.80 (1H, d), 8.22 (1H, d), 8.78 (1H, d).

MS (+ve ion electrospray) m/z 451 (MH+)

The dioxalate salt was prepared by the same method as for Example 1.

Example 3

(R)-2-{4-[(Benzo[1,3]dioxol-5-ylmethyl)-amino]-piperidin-1-yl}-1-(6-methoxy-quinolin-4-yl)-ethanol dioxalate

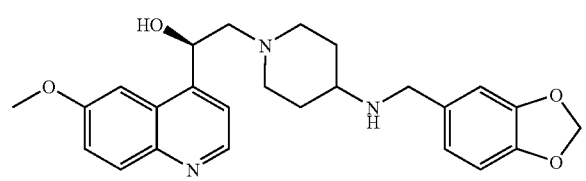

The title compound was prepared in the same manner as Example 1 using benzo[1,3]dioxole-5-carboxaldehyde as the aldehyde component. The crude reaction mixture was purified by chromatography on silica gel using a methanol and dichloromethane gradient to afford the free base of the title product as a colourless oil (48 mg, 33%).

δH (CDCl$_3$): 1.40–2.65 (8H, m), 2.80–2.85 (2H, m), 3.21 (1H, m), 3.74 (2H, s), 3.93 (3H, s), 5.40–5.44 (1H, dd), 5.94 (2H, s), 6.77 (2H, m), 6.84 (1H, s), 7.18 (1H, d), 7.34–7.39 (1H, dd), 7.64 (1H, d), 8.04 (1H, d), 8.76 (1H, d).

MS (+ve ion electrospray) m/z 436 (MH+).

The dioxalate salt was prepared by the same method as for Example 1.

Example 4

(R)-2-{4-[(2,2-Difluoro-benzo[1,3]dioxol-5-ylmethyl)-amino]-piperidin-1-yl}-1-(6-methoxy-quinolin-4-yl)-ethanol dioxolate

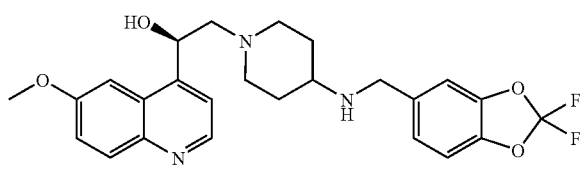

The title compound was prepared in the same manner as Example 1 using difluoro-benzo[1,3]dioxole-5-carboxaldehyde as the aldehyde component. The crude reaction mixture was purified by chromatography on silica gel using a methanol and dichloromethane gradient to afford the the free base of the title product as a colourless oil (30 mg, 19%).

δH (CDCl$_3$): 1.40–2.65 (8H, m), 2.80–2.85 (2H, m), 3.24–3.28 (1H, m), 3.82 (2H, s), 3.93 (3H, s), 5.46–5.41 (1H, dd), 6.97–7.05 (2H, m), 7.11 (1H, d), 7.18 (1H, d), 7.34–7.39 (1H, dd), 7.64 (1H, d), 8.04 (1H, d), 8.77 (1H, d). MS (+ve ion electrospray) m/z 472 (NH+).

The dioxalate salt was prepared by the same method as for Example 1.

Example 5

6-({1-[(R)-2-Hydroxy-2-(6-methoxy-quinolin-4-yl)-ethyl]-piperidin-4-ylamino}-methyl)-4H-benzo[1,4]oxazin-3-one dioxalate

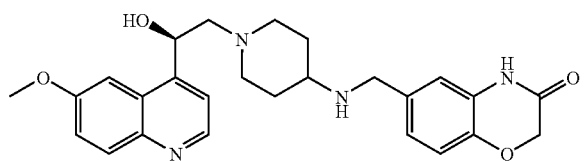

(a) (4-Formyl-2-nitro-phenoxy)-acetic acid ethyl ester

A solution of 4-hydroxy-3-nitro-benzaldehyde (6.9 g) and ethyl bromoacetate (5.0 ml) in dimethylformamide (250 ml) was treated with anhydrous potassium carbonate (10 g) and the mixture was heated at 60° C. for 18 hours and evaporated to dryness. The residue was partitioned between water and ether, and the ether layer was washed with 0.5M sodium hydroxide, dried over anhydrous sodium sulphate and evaporated to give an oil that was chromatographed on silica gel (ethyl acetate/dichloromethane) to afford an oil (1.9 g)

MS (+ve ion electrospray) m/z 253 (MH+).

(b) 3-Oxo-3,4-dihydro-2H-benzo[1,4]oxazine-6-carboxaldehyde

The ester (5a) (1.9 g) in acetic acid (40 ml) was treated with iron powder (4.2 g) and the mixture was stirred at 60° C. for 0.75 hours, filtered and evaporated to dryness. It was partitioned between aqueous sodium bicarbonate and ethyl acetate. The organic fraction was chromatographed on silica gel (ethyl acetate) to give a white solid (0.88 g).

MS (−ve ion electrospray) m/z 176 (M−H)$^-$

(c) Title Compound

A solution of theamine (1d) (300 mg) and carboxaldehyde (5b) (177 mg) in chloroform (3 ml) and methanol (0.5 ml) was treated with 3A molecular sieves and the mixture was heated under reflux for 3.5 hours. The cooled solution was treated with sodium borohydride (76 mg) in methanol (3 ml) and after 0.5 hours water was added and the mixture was extracted with chloroform, dried over sodium sulfate, and evaporated. It was chromatographed on silica gel (10% ammonia in methanol/ethyl acetate) to afford the free base of the title compound as a foam (0.24 g).

δH (CDCl$_3$): 1.55 (2H, m), 1.90–2.60 (8H, m), 2.85 (2H, m), 3.30 (1H, m), 3.50 (2H, s), 3.72 (2H, s), 3.90 (3H, s), 5.43 (1H, dd), 6.82 (1H, s), 6.92 (2H, s), 7.15 (1H, d), 7.35 (1H, dd), 7.65 (1H, d), 8.05 (1H, d), 8.80 (1H, d)

MS (+ve ion electrospray) m/z 463 (MH+).

The dioxalate salt was prepared by the same method as for Example 1.

Example 6

6-({1-[(R)-2-Hydroxy-2-(6-methoxy-quinolin-4-yl)-ethyl]-piperidin-4-ylamino}-methyl)-4H-benzo[1,4]thiazin-3-one dioxalate

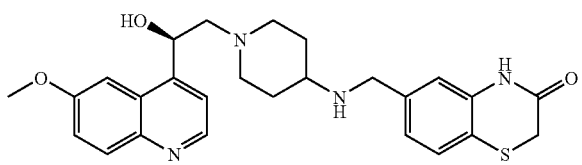

(a) 3-Oxo-3,4-dihydro-2H-benzo[1,4]thiazine-6-carboxylic acid

3-Oxo-3,4-dihydro-2H-benzo[1,4]thiazine-6-carboxylic acid methyl ester (6.74 g) was suspended in tetrahydrofuran (100 ml) and 2M sodium hydroxide (30 ml) was added followed by water (20 ml). The solution was stirred for 2.5 hours, evaporated to half volume and acidified with 2M hydrochloric acid. The product was collected, washed with water and dried in vacuo, to give a white solid (6.2 g).

MS (−ve ion electrospray) m/z 208 (M−H)$^-$

(b) 6-Hydroxymethyl-4H-benzo[1,4]thiazin-3-one

The acid (6a) in tetrahydrofuran (50 ml) and triethylamine (4.7 ml) was cooled to 0° C. and isobutylchloroformate (4.02 ml) was added dropwise and the solution was stirred at 0° C. for 2 hours, when it was filtered into a stirred solution of sodium borohydride (3.14 g) in ice/water (50 ml). The mixture was stirred at 0° C. for 1 hour and allowed to warm to room temperature. It was acidified with 2M hydrochloric acid, evaporated to half volume, and the resulting product was collected, washed with water and dried in vacuo, to give a white solid (4.5 g).

MS (−ve ion electrospray) m/z 194 (M−H)$^-$

(c) 3-Oxo-3,4-dihydro-2H-benzo[1,4]thiazine-6-carboxaldehyde

A stirred solution of the alcohol (6b) (3.5 g) in chloroform (150 ml) and tetrahydrofuran (300 ml) was treated with manganese dioxide (7.8 g) for 18 hours and was filtered and evaporated to give a white solid (2.5 g).

MS (−ve ion electrospray) m/z 194 (M−H)−

(d) Title Compound

A solution of the amine (1d; 94% ee) (0.40 g) and carboxaldehyde (6c) (0.251 g) in dichloromethane (10 ml) and methanol (10 ml) was treated with 3A molecular sieves and the mixture was stirred at room temperature for 18 hours. The solution was treated with sodium borohydride (148 mg) in portions and after 3 hours the solution was filtered and evaporated to dryness. The product in water and chloroform was acidified with 2M hydrochloric acid, then basified with sodium bicarbonate, extracted with chloroform, dried over sodium sulfate, and evaporated. It was chromatographed on silica gel (methanol/dichloromethane) to afford the free base of the title compound as a foam (0.34 g).

δH (CDCl₃): 1.45 (2H, m), 1.80–2.60 (8H, m), 2.75 (2H, m), 3.20 (1H, m), 3.35 (2H, s), 3.75 (2H, s), 3.85 (3H, s), 5.37 (1H, dd), 6.80 (1H, s), 6.90 (1H, dd), 7.10 (1H, d) 7.20 (2H, m), 7.30 (1H, dd), 7.55 (1H, d), 7.98 (1H, d), 8.40 (1H, brs), 8.70 (1H, d)

MS (+ve ion electrospray) m/z 479 (MH+).

The dioxalate salt was prepared by the same method as for Example 1.

Example 7

4-[(3-Oxo-3,4-dihydro-2H-benzo[1,4]thiazin-6-ylmethyl)-amino]-piperidine-1-carboxylic acid (6-methoxy-[1,5]naphthyridin-4-yl)-amide oxalate

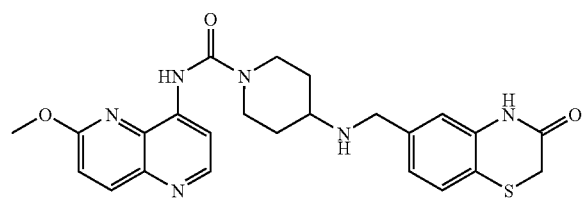

(a) 4-Amino-6-methoxy-[1,5]naphthyridine

A solution of the triflate (2b) (8.0 g) and propylamine hydrochloride (15.8 g) in pyridine (120 ml) was heated at reflux for 4 hours. The solvent was evaporated and the mixture dissolved in 0.05M hydrochloric acid (600 ml) and washed with dichloromethane. The mixture was basified with 40% aqueous sodium hydroxide and extracted with dichloromethane. The extracts were dried, evaporated and chromatographed on silica gel (2–5% methanol in dichloromethane) to give an orange solid (3.6 g, 63%).

δH (CDCl₃): 4.05 (3H, s), 5.25 (2H, brs), 6.71 (1H, d), 7.08 (1H, d), 8.09 (1H, d), 8.39 (1H, d).

MS (+ve ion electrospray) m/z: 176 (MH+).

(b) 4-tert-Butyloxycarbonylamino-1-(6-methoxy-[1,5]naphthyridin-4-yl)aminocarbonylpiperidine To a solution of 4-amino-6-methoxy-[1,5]naphthyridine (7a) (2.1 g, 13.5 mmol) and 4-(dimethylamino)pyridine (1.62 g) in anhydrous chloroform (45 ml) was added N,N-carbonyldiimidazole (3.28 g, 20.1 mmol). The mixture was stirred for 4 hours at room temperature, then evaporated and the residue was dissolved in anhydrous N,N-dimethylformamide (45 ml). 4-tert-Butoxycarbonylaminopiperidine hydrochloride (3.34 g, 13.5 mmol) and potassium carbonate (1.89 g) were added, and the mixture was heated at 70° C. overnight. The mixture was evaporated and the residue was mixed with water (120 ml). The solid was filtered off and dried (3.89 g).

MS (+ve ion electrospray) m/z 402 (MH+).

(c) 4-Amino-1-(6-methoxy-[1,5]naphthyridin-4-yl)aminocarbonylpiperidine

The tert-butoxycarbonylamino compound (7b) (3.88 g, 9.7 mmol) was treated with trifluoroacetic acid and hydrogen chloride (4M in dioxan) as described in Example (1d). The crude hydrochloride was dissolved in water and washed twice with dichloromethane, basified to pH 9 and evaporated to dryness. Extraction with 10% methanol/dichloromethane gave the free base (3.45 g).

MS (+ve ion electrospray) m/z 302 (MH+).

(d) Title Compound

A mixture of amine (7c) (0.15 g), carboxaldehyde (6c) (0.10 g) and 3A molecular sieves in dichloromethane (3 ml) and methanol (1 ml) was stirred at room temperature for 18 hours. Sodium borohydride (0.049 g) was added and the mixture was stirred for a further 24 hours. It was quenched with water and extracted with ethyl acetate. The organic layer was dried, evaporated and chromatographed on silica gel (methanol/dichloromethane) to afford the free base of the title compound as a solid (83 mg).

δH (CDCl₃): 1.55 (2H, m), 2.0 (2H, m), 2.80 (1H, m), 3.15 (2H, m), 3.40 (2H, s), 3.80 (2H, s), 4.02 (3H, s), 4.10 (2H, m), 6.82 (1H, s), 7.00 (1H, d), 7.15 (1H, d) 7.30 (1H, m), 8.10 (1H, br s), 8.20 (1H, d), 8.30 (1H, d), 8.65 (1H, d), 9.10 (1H, br s)

MS (+ve ion electrospray) m/z 479 (MH+)

The oxalate salt was prepared by a similar method as for Example 1.

Example 8

7-Fluoro-6-({1-[(R)-2-Hydroxy-2-(6-methoxy-quinolin-4-yl)-ethyl]-piperidin-4-ylamino}-methyl)-4H-benzo[1,4]oxazin-3-one dioxalate

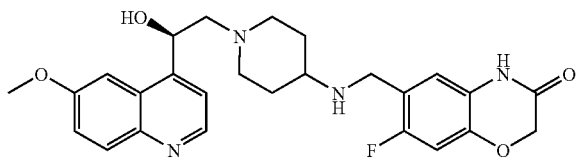

(a) 5-Amino-2-fluoro-4-hydroxy-benzonitrile

This was prepared by from 2-fluoro-4-hydroxy-benzonitrile by nitration (concentrated nitric acid in acetic acid at 40° C.) followed by hydrogenation in ethanol over 10% palladium/carbon.

(b) 7-Fluoro-3-oxo-3,4-dihydro-2H-benzo[1,4]oxazine-6-carbonitrile

This was prepared by the general method of Xian Huang and Cheng-Chu Chan, *Synthesis,* 851 (1984). A mixture of amine (8a) (1 g), benzyltriethylammonium chloride (1.5 g) and sodium bicarbonate (2.22 g) in chloroform (20 ml) at 0° C. was treated with chloroacetyl chloride (0.632 ml) in chloroform (5 ml) and then stirred at 5° C. for 1 hour and then heated at 55° C. for 5 hours. The mixture was evaporated to dryness, treated with water, and filtered to give a solid that was recrystallised from ethanol to give a white solid (0.35 g). A further (0.24 g) was obtained after chromatography of the mother liquors on silica gel (chloroform then methanol/dichloromethane).

MS (−ve ion electrospray) m/z 191 (M−H)⁻

(c) 7-Fluoro-3-oxo-3,4-dihydro-2H-benzo[1,4]oxazine-6-carboxylic Acid

The carbonitrile (8b) (0.2 g) was heated under reflux in tetrahydrofuran (20 ml) and water (20 ml) containing sodium hydroxide (0.167 g) for 72 hours. It was acidified with 2M hydrochloric acid and the product was collected and dried in vacuo to give a white solid (0.18 g).

MS (−ve ion electrospray) m/z 210 (M—H)⁻

(d) 7-Fluoro-6-hydroxymethyl-4H-benzo[1,4]oxazin-3-one

This was prepared from carboxylic acid (8c) (1.7 g) by the procedure described in Example (6b) to give a solid (0.7 g).

MS (−ve ion electrospray) m/z 196 (M−H)⁻

(e) 7-Fluoro-3-oxo-3,4-dihydro-2H-benzo[1,4]oxazine-6-carboxaldehyde

This was prepared from the alcohol (8d) (0.7 g) by the procedure described in Example (6c) to give a solid (0.51 g).

MS (−ve ion electrospray) m/z 194 (M−H)⁻

(f) Title Compound

This was prepared from the carboxaldehyde (8e) (117 mg) and amine (1d) (0.15 g) by the procedure described in Example (6d) to give the free base of the title compound as a foam (0.126 g).

δH (CDCl₃): 1.55 (2H, m), 1.90–2.60 (8H, m), 2.85 (2H, m), 3.30 (1H, m), 3.78 (2H, s), 3.90 (3H, s), 4.60 (2H, s), 5.40 (1H, dd), 6.70 (1H, d), 6.80 (1H, d), 7.20 (1H, d), 7.35 (1H, dd), 7.65 (1H, d), 8.05 (1H, d), 8.80 (1H, d)

MS (+ve ion electrospray) m/z 481 (MH+).

The dioxalate salt was prepared by the same method as for Example 1.

Example 9

6-({1-[(R)-2-Hydroxy-2-(6-methoxy-[1,5]naphthyridin-4-yl)-ethyl]-piperidin-4-ylamino}-methyl)-4H-benzo[1,4]oxazin-3-one dioxalate

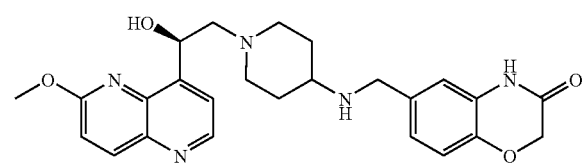

This was prepared from amine (2f) and aldehyde (5b) by the same reductive alkylation procedure as for Example 5, giving the free base of the title compound as an oil (165 mg, 55%).

δH (CDCl₃): 1.60 (2H, m), 2.05 (2H, m), 2.25 (1H, m), 2.45 (2H, m), 2.70 (1H, m), 2.85 (2H, m), 3.30 (1H, m), 3.75 (2H, s), 4.00 (3H, s), 4.58 (2H, s), 5.75 (1H, dd), 6.90 (3H, m), 7.13 (1H, d), 7.80 (1H, d), 8.25 (1H, d), 8.78 (1H, d).

MS (+ve ion electrospray) m/z 464 (MH+)

This material was converted to the dioxalate salt by the procedure of Example 1.

Example 10

(R)-2-{4-[(6-Chloro-benzo[1,3]dioxol-5-ylmethyl)-amino]-piperidin-1-yl}-1-(6-methoxy-quinolin-4-yl)-ethanol dioxalate

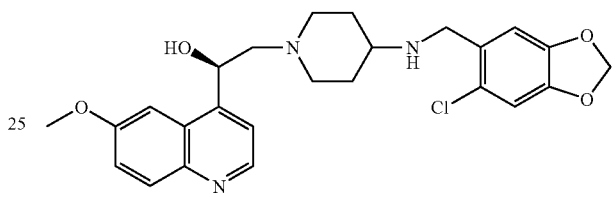

The title compound was prepared in the same manner as Example 1 using 6-chloro-benzo[1,3]dioxole-5-carboxaldehyde as the aldehyde component. The crude reaction mixture was purified by chromatography on silica gel using a methanol and dichloromethane gradient to afford the free base of the desired product as a colourless oil (48 mg, 31%).

δH (CDCl₃): 1.25–2.57 (8H, m), 2.79–2.85 (2H, m), 3.22–3.27 (1H, m), 3.81 (2H, s), 3.92 (3H, s), 5.40–5.45 (1H, dd), 5.96 (2H, s), 6.83 (1H, s), 6.89 (1H, s), 7.18 (1H, d), 7.34–7.39 (1H, dd), 7.64 (1H, d), 8.03 (1H, d), 8.75 (1H, d).

MS (+ve ion electrospray) m/z 470 (MH+).

This material was converted to the dioxalate salt (133 mg) by the procedure of Example 1.

Example 11

5-Fluoro-6-({1-[(R)-2-hydroxy-2-(6-methoxy-quinolin-4-yl)-ethyl]-piperidin-4-ylamino}-methyl)-3-methyl-3H-benzoxazol-2-one dioxalate

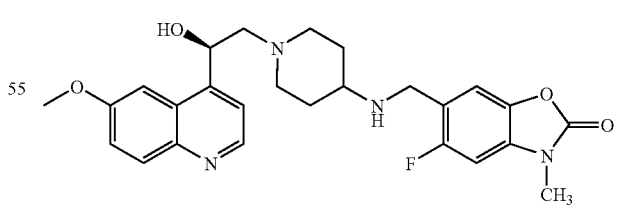

(a) 5-Fluoro-3H-benzoxazol-2-one

Carbonyl diimidazole (7.6 g) was added to a solution of 2-amino-4-fluorophenol (5 g, 39 mmol) in dichloromethane (0.100 ml). After 14 hours the solution was washed with 5M δH (CD₃OD): 3.51 (3H, s), 7.23–7.11 (4H, m).

aqueous HCl, water, and dried over magnesium sulfate. The solution was filtered through a plug of silica and evaporated affording a white solid (4.0 g, 66%).

MS (+ve ion electrospray) m/z 154 (MH+)

(b) 5-Fluoro-3-methyl-3H-benzoxazol-2-one

A solution of (11a) (1.0 g, 6.5 mmol) in tetrahydrofuran/water (10 ml/10 ml) was treated with potassium hydroxide (0.51 g, 9.1 mmol) and dimethylsulphate (0.7 ml, 7.2 mmol) then heated at 60° C. for 4 hours. The mixture was evaporated and partitioned between dichloromethane and water. The dichloromethane extract was dried and evaporated and the residue chromatographed on silica eluting with an ethyl acetate/dichloromethane gradient affording a white solid (0.91 g, 83%).

MS (+ve ion electrospray) m/z 168 (MH+)

(c) 5-Fluoro-3-methyl-2-oxo-2,3-dihydro-benzoxazole-6-carboxaldehyde

A solution of (11b) (0.9 g, 5.4 mmol) in methanesulphonic acid (6 ml) was treated cautiously with hexamethylene tetramine (1.5 g, 10.8 mmol) and heated at 110° C. for 1 hour. The mixture was added to ice/water, extracted with ethyl acetate and the extracts dried and evaporated giving a yellow solid (0.78 g, 73%).

MS (+ve ion electrospray) m/z 196 (MH+)

(d) Title Compound

This was prepared from amine (1d) (0.21 g) and aldehyde (11c) (0.15 g) by the same reductive alkylation procedure as for Example 5, giving the free base of the title compound as an oil (151 mg).

δH (CDCl$_3$): 1.55 (2H, m), 2.05 (2H, m), 2.25 (1H, m), 2.45 (2H, m), 2.70 (1H, m), 2.85 (2H, m), 3.30 (1H, m), 3.40 (3H, s), 3.90 (2H, s), 3.94 (3H, s), 5.45 (1H, dd), 6.68 (1H, d), 7.15 (1H, d), 7.20 (1H, d), 7.35 (1H, dd), 7.62 (1H, d), 8.02 (1H, d), 8.75 (1H, d).

MS (+ve ion electrospray) m/z 481 (MH+).

This material was converted to the dioxalate salt (147 mg) by the procedure of Example 1.

Example 12

2,3-Dihydro-benzo[1,4]dioxine-6-carboxylic Acid {1-[(R)-2-hydroxy-2-(6-methoxy-quinolin-4-yl)-ethyl]-piperidin-4-yl}-amide oxalate

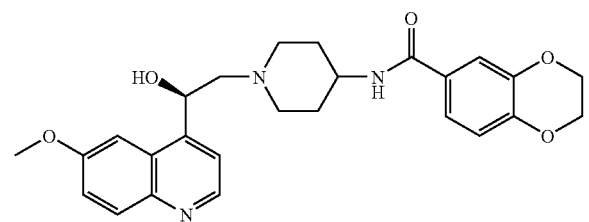

(a) 2,3-Dihydro-benzo[1,4]dioxine-6-carboxylic Acid 2,3-Dihydro-benzo[1,4]dioxine-6-carboxaldehyde (2.03 g, 12.4 mmol), was slurried in water (50 ml) at 80° C. Potassium permanganate (2.70 g, 17.1 mmol) as a solution in water (50 ml) was added over 1 hour. The mixture was then heated for a further 2 hours after which time the reaction mixture was basified with 10% aqueous potassium hydroxide. The resulting precipitate was removed by filtration and washed with water (2×50 ml). The combined filtrates were acidified with concentrated hydrochloric acid and the resulting solid isolated by filtration and dried under vacuum. This provided the desired compound as a white solid (1.50 g, 67%).

δH (CD$_3$OD): 4.32–4.24 (4H, m), 6.87 (1H, d), 7.52–7.47 (2H, m).

(b) Title Compound

Amine (1d) (127 mg, 0.44 mmol), carboxylic acid (12a) (76 mg, 0.44 mmol) and O-(7-azabenzotriazol-1-yl)-N,N,N'N'-tetramethyluronium hexafluorophosphate (160 mg, 0.44 mmol) were dissolved in N,N-dimethylformamide (5 ml). To this solution triethylamine (0.12 ml, 0.44 mmol) was added. The resulting mixture was stirred at room temperature for 10 hours after which time the volatiles were removed in vacuo. The residue was partitioned between ethyl acetate (2×100 ml) and brine (20 ml). The organic phase was dried over magnesium sulphate and the volatiles again removed in vacuo. The resulting solid was subjected to purification by chromatography on silica gel using a methanol dichloromethane solvent gradient. This afforded the desired amide as a colourless solid (76 mg, 39%).

δH (CDCl$_3$): 1.63–1.72 (2H, m), 2.05–2.19 (2H, m), 2.35–2.62 (3H, m), 2.87–2.92 (2H, dd), 3.29–3.34 (1H, m), 3.94 (3H, s), 4.03 (1H, m), 4.27–4.31 (4H, m), 5.48–5.51 (1H, dd), 5.97 (1H, d), 6.89 (1H, m), 7.18 (1H, d), 7.28 (1H, m), 7.31 (1H, d), 7.36–7.40 (1H, dd), 7.64 (1H, d), 8.04 (1H, d), 8.77 (1H, d).

MS (+ve ion electrospray) m/z 464 (MH+).

A solution of the solid (76 mg) in dichloromethane (1 ml) was added to oxalic acid (15 mg) in diethyl ether (10 ml) to generate the monooxalate salt. The title compound was isolated by centrifugation, washing with diethyl ether and subsequent drying in vacuo.

Example 13

6-({1-[(R)-2-Hydroxy-2-(6-methoxy-quinolin-4-yl)-ethyl]-piperidin-4-ylamino}-methyl)-3-methyl-3H-benzoxazole-2-thione difumarate

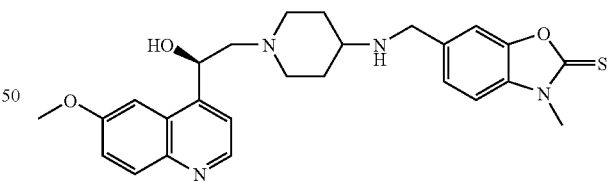

(a) 3-Methyl-3H-benzooxazole-2-thione

3-Methyl-3H-benzoxazol-2-one (2.0 g, 13.4 mmol) was treated with diphosphorus pentasulphide (4.0 g, 18 mmol). The mixture was heated to 140° C. for 2 hours with vigorous stirring. The solid was cooled and then extracted with toluene (2×50 ml). The toluene extract was evaporated in vacuo and the residue partitioned between ethyl acetate (2×10 ml) and water (20 ml). The organic phases were combined and dried over magnesium sulfate. The volatiles were removed in vacuo to provide the desired compound as a white solid (1.77 g, 80%).

(b) 3-Methyl-2-thioxo-2,3-dihydro-benzoxazole-6-carboxaldehyde.

Thione (13a) (527 mg, 3.20 mmol) and hexamethylenetetramine (817 mg, 6.4 mmol) were dissolved in trifluoroacetic acid (5 ml) and heated at reflux for 20 hours. The volatiles were removed in vacuo and the residue was treated with ice/water (20 ml). The resultant mixture was stirred for 40 minutes and then made basic with sodium carbonate. The solid was isolated by filtration and washed with water then dried under vacuum. The solid was purified by column chromatography on silica gel eluting with an ethyl acetate and hexane solvent gradient. This provided the desired product as a white solid (136 mg, 20%).

δH (CD₃OD): 3.64 (1H, s), 7.40 (1H, d), 7.88–7.81 (2H, m), 9.92 (1H, s).

(c) Title Compound

Amine (1d) (150 mg, 0.5 mmol), was dissolved in dichloromethane (3 ml) and methanol (1 ml). To this solution was added activated 3A molecular sieves (1 g) and carboxaldehyde (13b) (96 mg, 0.5 mmol). The resulting solution was heated at 50° C. for 6 hours and then the solution was cooled in an ice bath. Sodium borohydride (57 mg, 1.50 mmol) was added. The resulting slurry was stirred at room temperature for a further 10 hours. The reaction mixture was quenched by the addition of water (2 ml) and the volatiles removed in vacuo. The residue was partitioned between ethyl acetate (2×100 ml) and brine (20 ml). The organic phases were combined and dried over magnesium sulphate. The volatiles were again removed under reduced pressure and the resulting oil was subjected to purification on silica gel using a methanol/dichloromethane gradient. This afforded the free base of the title compound as a colourless oil (71 mg, 30%).

δH (CD₃OD): 1.47–1.60 (2H, m), 1.87–2.10 (2H, m), 2.14–2.26 (2H, m), 2.50–2.71 (3H, m), 3.00–3.20 (2H, m), 3.65 (3H, s), 3.85 (2H, s), 3.94 (3H, s), 5.55–5.60 (1H, dd), 7.22 (1H, d), 7.31–7.40 (4H, m), 7.66 (1H, d), 7.90 (1H, d), 8.64 (1H, d).

MS (+ve ion electrospray) m/z 479 (MH+).

To a solution of the oil (71 mg) in dichloromethane (10 ml) was added fumaric acid (34 mg) in methanol:dichloromethane (1:1, 10 ml) to generate the difumarate salt. The title compound was isolated by concentration and drying in vacuo.

Example 14

6-({1-[(R)-2-Hydroxy-2-(6-methoxy-quinolin-4-yl)-ethyl]-piperidin-4-ylamino}-methyl)-3-methyl-3H-benzoxazol-2-one dioxalate

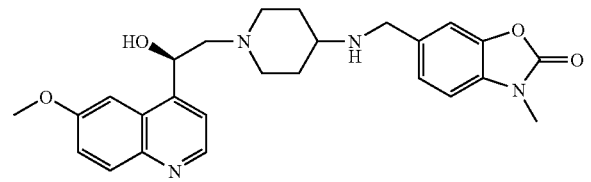

(a) 3-Methyl-2-oxo-2,3-dihydro-benzoxazole-6-carboxaldehyde

3-Methyl-3H-benzoxazol-2-one (2.0 g, 13.4 mmol) and hexamethylenetetramine (3.7 g, 26.8 mmol) were dissolved in trifluoroacetic acid (20 ml) and heated at reflux for 20 hours. The volatiles were removed in vacuo and the residue was treated with ice water (60 ml). The resultant mixture was stirred for 30 minutes and then basified with sodium carbonate. The solid was isolated by filtration, washed with water and then dried under vacuum. The solid was purified by column chromatography on silica gel eluting with an ethyl acetate and hexane solvent gradient. This provided the aldehyde as a white solid (1.07 g, 45%).

δH (CDCl₃): 3.48 (3H, s), 7.10 (1H, d), 7.33 (1H, d), 7.80–7.76 (1H, dd), 9.95 (1H, s).

(b) Title Compound

Amine (1d) (120 mg, 0.4 mmol) and carboxaldehyde (14a) (71 mg, 0.4 mmol) were dissolved in dichloromethane (4 ml) and methanol (1 ml). To this solution was added freshly activated 3A molecular sieves (1 g). The resulting solution was stirred at room temperature for 5 hours and then cooled and sodium borohydride (46 mg, 1.2 mmol) was added. The resulting slurry was stirred at room temperature for a further 10 hours. The reaction mixture was quenched by the addition of water (2 ml) and the volatiles removed in vacuo. The residue was partitioned between ethyl acetate (2×100 ml) and brine (20 ml). The organic phases were combined and dried over magnesium sulphate. The volatiles were again removed under reduced pressure and the resulting oil was subjected to purification on silica gel using a methanol and dichloromethane gradient. This afforded the free base of the title compound as a colourless oil (52 mg, 28%).

δH (CDCl₃): 1.45–2.59 (8H, m), 2.80–2.87 (2H, m), 3.24–3.28 (1H, m), 3.40 (3H, s), 3.86 (2H, s), 3.93 (3H, s), 5.42–5.45 (1H, dd), 6.90 (1H, d), 7.15–7.18 (2H, m), 7.24 (1H, m), 7.35–7.40 (1H, dd), 7.64 (1H, d), 8.03 (1H, d), 8.77 (1H, d).

MS (+ve ion electrospray) m/z 463 (MH+).

This was converted to the dioxalate salt by the method of Example 1.

Example 15

3-Oxo-3,4-dihydro-2H-benzo[1,4]thiazine-6-sulfonic acid {1-[(R)-2-hydroxy-2-(6-methoxy-quinolin-4-yl)-ethyl]-piperidin-4-yl}-amide oxalate

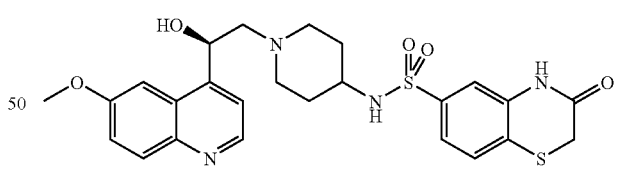

(a) 3-Oxo-3,4-dihydro-2H-benzo[1,4]thiazine-6-sulfonyl chloride

4H-Benzo[1,4]thiazin-3-one (7.0 g) was added cautiously portionwise to chlorosulfonic acid (15 ml) at 0° C. over 20 minutes and the solution was stirred cold for 1 hour and then heated at 45° C. for 2 hours. It was cooled and poured slowly into iced-water. The product was collected, washed well with water and dried in vacuo to give a white solid (7.0 g).

δH (CDCl₃): 3.57 (2H, s), 7.53 (1H, d), 7.58 (1H, d), 7.69 (1H, dd), 8.94 (1H, br s).

(b) Title Compound

The amine (1d) (0.10 g) in tetrahydrofuran (5 ml) and chloroform (5 ml) was treated with diisopropylethylamine (0.3 ml) and then the sulfonyl chloride (15a) (0.092 g) was added portionwise at 0° C. The solution was stirred at 0° C. for 1 hour and evaporated to dryness. Aqueous sodium carbonate was added and the mixture was extracted with chloroform, dried and evaporated. The product was chromatographed on silica gel (methanol/dichloromethane) to afford the free base as a foam (0.12 g).

δH (CDCl$_3$): 1.55–2.60 (8H, m), 2.75 (2H, m), 3.20 (2H, m), 3.50 (2H, s), 3.90 (3H, s), 5.38 (1H, dd), 5.48 (1H, br s), 7.10 (1H, d), 7.25 (2H, m), 7.36 (1H, dd) 7.40 (1H, s), 7.60 (1H, d), 8.05 (1H, d), 8.75 (1H, d), 8.95 (1H, br s)

MS (+ve ion electrospray) m/z 529 (MH+).

This was converted to the oxalate salt in a similar method to that for Example 1.

Example 16

6-({1-[(R)-2-Hydroxy-2-(6-methoxy-[1,5]naphthyridin-4-yl)-ethyl]-piperidin-4-ylamino}-methyl)-4H-benzo[1,4]thiazin-3-one dioxalate

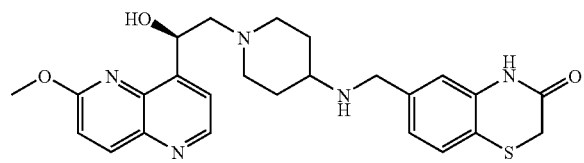

A solution of the amine (2f) (0.15 g) and carboxaldehyde (6c) (0.105 g) in dichloromethane (3 ml) and methanol (3 ml) was treated with 3A molecular sieves and the mixture was stirred at room temperature for 18 hours. The solution was treated with sodium borohydride (56 mg) in portions and after 3 hours the solution was filtered and evaporated to dryness. The product in water and chloroform was acidified with 2M hydrochloric acid, then basified with sodium bicarbonate, extracted with chloroform, dried over sodium sulfate, and evaporated. It was chromatographed on silica gel (methanol/dichloromethane) to afford the free base as a foam (0.13 g).

δH (CDCl$_3$): 1.45–2.10 (5H, m), 2.18 (1H, t), 2.40 (2H, m), 2.55 (1H, m), 2.83 (1H, m), 3.10 (1H, dd), 3.30 (1H, m), 3.42 (2H, m), 3.80 (2H, s), 4.03 (3H, s), 5.72 (1H, dd), 6.82 (1H, s), 7.00 (1H, d), 7.12 (1H, d) 7.25 (1H, d), 7.80 (1H, d), 8.00 (1H, br s), 8.20 (1H, d), 8.78 (1H, d)

MS (+ve ion electrospray) m/z 480 (MH+).

This was converted to the dioxalate salt by the method of Example 1.

Example 17

4-Oxo-2,3,4,5-tetrahydro-benzo[b][1,4]thiazepine-7-sulfonic acid {1-[(R)-2-hydroxy-2-(6-methoxy-[1,5]naphthyridin-4-yl)-ethyl]-piperidin-4-yl}-amide oxalate

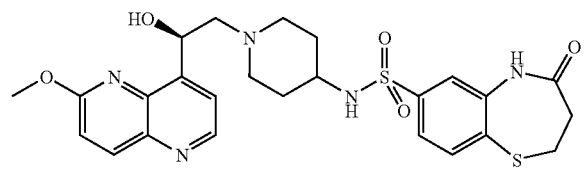

(a) 4-Oxo-2,3,4,5-tetrahydro-benzo[b][1,4]thiazepine-7-sulfonyl chloride

This was prepared from 4-oxo-2,3,4,5-tetrahydro-benzo[b][1,4]thiazepine by the method of Example (15a).

δH (CDCl$_3$): 2.76 (2H, t), 3.58 (2H, t), 7.75 (1H, d), 7.81 (1H, dd), 7.86 (1H, d), 8.23 (1H, br s).

(b) Title Compound

This was prepared from amine (2f) and sulfonyl chloride (a) by the method of Example (15b).

δH (CDCl$_3$): 1.70 (1H, m), 1.90 (1H, m), 2.30 (2H, m), 2.55 (2H, t), 2.70 (2H, m), 2.90 (1H, m), 3.10 (2H, m), 3.30 (2H, m), 3.50 (2H, m), 4.00 (3H, s), 5.75 (1H, dd), 7.10 (1H, d), 7.60–7.75 (4H, m), 8.20 (1H, d), 8.50 (1 h, bs), 8.75 (1H, d).

MS (+ve ion electrospray) m/z 544 (MH+).

This was converted to the oxalate salt by a similar method to that of Example 1

Example 18

(R)-1-(6-Methoxy-quinolin-4-yl)-2-{4-[(6-nitro-benzo[1,3]dioxol-5-ylmethyl)-amino]-piperidin-1-yl}-ethanol dioxalate

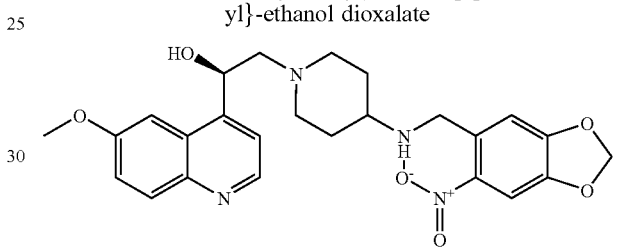

The title compound was prepared in the same manner as Example 1 using 6-nitro-benzo[1,3]dioxole-5-carboxaldehyde as the aldehyde component. The crude reaction mixture was purified by chromatography on silica gel using a methanol and dichloromethane gradient to afford the free base of the title product as a colourless oil (120 mg, 40%).

δH (CDCl$_3$): 1.40–1.60 (2H, m), 1.90–2.00 (2H, m) 2.20–2.60 (4H, m), 2.80–2.85 (2H, m), 3.30 (1H, m), 3.90 (3H, s), 4.00 (2H, s), 5.45 (1H, dd), 6.10 (2H, s), 7.10 (1H, s), 7.18 (1H, d), 7.38 (1H, dd), 7.55 (1H, s), 7.65 (1H, d), 8.05 (1H, d), 8.78 (1H, d).

MS (+ve ion electrospray) m/z 481 (MH+).

The dioxalate salt was prepared by the same method as for Example 1.

Example 19

(R)-2-{4-[(2,3-Dihydro-[1,4]dioxino[2,3-b]pyridin-6-ylmethyl)-amino]-piperidin-1-yl}-1-(6-methoxy-quinolin-4-yl)-ethanol dioxalate

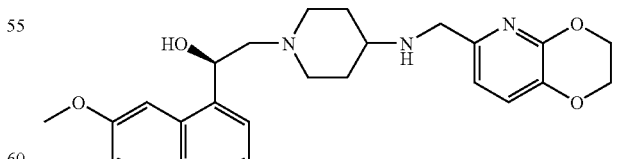

(a) 2-(2-Iodo-6-methyl-pyridin-3-yloxy)-ethanol

2-Iodo-6-methyl-pyridin-3-ol (6.49 g, 27.6 mmol) was stirred in a 1M solution of sodium hydroxide (30 ml). To this was added 1-bromoethan-2-ol (3.91 ml, 55.20 mmol) dropwise at room temperature. The resulting solution was then heated to 100° C. and stirred for 2 hours. The reaction mixture was cooled and then extracted into chloroform (2×100 ml). The organic phases were combined and extracted with a solution of 1M sodium hydroxide (25 ml). The organic phase was then dried over magnesium sulfate and concentrated in vacuo. This provided the desired product which was used without further purification (5.26 g).

(b) 6-Methyl-2,3-dihydro-[1,4]dioxino[2,3-b]pyridine

The pyridine (19a) (6.52 g, 23.37 mmol) was dissolved in N,N'-dimethylformamide (30 ml). The solution was cooled to 0° C. and sodium hydride was added (1.12 g, 28.04 mmol). This was followed by copper powder (0.62 g, 9.82 mmol) and copper sulphate (1.87 g, 11.69 mmol). The resulting slurry was stirred at 100° C. under argon for 12 hours after which time it was quenched with water (2 ml). The volatiles were removed under reduced pressure and the residue was subjected to purification on silica gel employing a methanol-dichloromethane solvent gradient. This provided the desired compound as a brown semi-solid (480 mg, 14%).

(c) 6-Bromomethyl-2,3-dihydro-[1,4]dioxino[2,3-b]pyridine

The pyridine (19b) (192 mg, 1.27 mmol) was dissolved in carbon tetrachloride (10 ml). To the resulting solution was added N-bromosuccinimide (249 mg, 1.399 mmol). The solution was then heated to reflux and irradiated with a 200W desktop lamp. The irradiation was continued for 1 hour after which time the reaction mixture was cooled and the volatiles removed under reduced pressure. The residue was purified on silica gel using an ethyl acetate-hexanes solvent gradient. This provided the desired compound as a white solid (13 mg; 4%).

(d) Title Compound

The amine (1d) (13 mg, 0.04 mmol) was dissolved in N,N'-dimethylformamide (3 ml). To this solution was added potassium carbonate (15 mg, 0.11 mmol) and pyridine (19c) (10 mg, 0.04 mmol). The resulting suspension was stirred at room temperature for 48 hours. The reaction mixture was concentrated under vacuum and the residue was purified on silica gel using a methanol-dichloromethane gradient. This afforded the desired compound as a colourless oil (7 mg; 36%).

δH (CDCl$_3$): 1.55–1.75 (2H, m), 2.00–2.65 (7H, m), 2.85–2.91 (1H, m), 3.25–3.30 (1H, m), 3.85 (2H, s), 3.94 (3H, s), 4.22–4.27 (2H, m), 4.26–4.35 (2H, m), 5.57–5.60 (1H, m), 6.89 (1H, d), 7.20 (1H, d), 7.26 (1H, d), 7.38 (1H, dd), 7.69 (1H, d), 8.03 (1H, d), 8.77 (1H, d).

MS (APCI+) m/z 451 (MH+).

This was converted to the dioxalate salt by the method of Example 1.

Example 20

7-({1-[(R)-2-Hydroxy-2-(6-methoxy-quinolin-4-yl)-ethyl]-piperidin-4-ylamino}-methyl)-1-H-pyrido[2,3-b][1,4]thiazin-2-one dioxalate

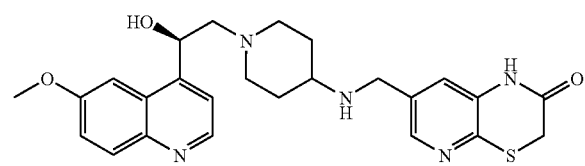

Method A (a) 6-Methoxycarbonylmethylsulfanyl-5-nitro-nicotinic acid methyl ester A solution of 6-chloro-5-nitro-nicotinic acid methyl ester (1.0 g) [prepared as described by A. H. Berrie et al. *J. Chem. Soc.* 2590–2594 (1951)] in dichloromethane (10 ml) containing triethylamine (0.76 ml) was treated with mercaptoacetic acid methyl ester (0.441 ml) and the solution was stirred at room temperature for 1 hour and evaporated to dryness. Sodium bicarbonate solution was added and the mixture was extracted with dichloromethane, dried (anhydrous sodium sulfate) and evaporated to afford a solid (1.0 g).

MS (+ve ion electrospray) m/z 287 (MH+).

(b) 2-Oxo-2,3-dihydro-1H-pyrido[2,3-b][1,4]thiazine-7-carboxylic acid methyl ester The ester (20a) (1.0 g) in acetic acid (50 ml) was treated with iron powder (10 g) and the mixture was stirred and heated at 60° C. for 1 hour, cooled and filtered. The filtrate was evaporated, treated with sodium bicarbonate solution and extracted with warm chloroform. It was dried (anhydrous sodium sulfate) and evaporated to give a white solid (0.85 g).

MS (+ve ion electrospray) m/z 225 (MH+).

(c) 2-Oxo-2,3-dihydro-1H-pyrido[2,3-b][1,4]thiazine-7-carboxylic acid

The ester (20b) (2.8 g) was hydrolysed with aqueous sodium hydroxide in tetrahydrofuran by the method of Example (6a) to afford a solid (2.5 g).

MS (−ve ion electrospray) m/z 209 (M−H−).

(d) 7-Hydroxymethyl-1H-pyrido[2,3-b][1,4]thiazin-2-one

The carboxylic acid (20c) (2.48 g) was reacted with isobutylchloroformate and sodium borohydride by the method of Example (6b) to afford a solid (1.3 g), after recrystallisation from chloroform-methanol (9:1).

MS (+ve ion electrospray) m/z 197 (MH+).

(e) 2-Oxo-2,3-dihydro-1H-pyrido[2,3-b][1,4]thiazine-7-carboxaldehyde

The alcohol (20d) (1.22 g) was oxidised with manganese dioxide by the method of Example (6c) to afford a solid (0.7 g).

MS (−ve ion electrospray) m/z 193 (M−H−).

Method B (d) 7-Hydroxymethyl-1H-pyrido[2,3-b][1,4]thiazin-2-one

The ester (20b) (14 g, 0.0625 mole) in THF (300 mL) was cooled to 0° C. and treated dropwise with Super-hydride (lithium triethylborohydride) (1.0 M solution in THF, 218 mL, 0.218 mole). The resulting mixture was stirred at 0° C. for 1 hr and quenched with saturated aqueous NH$_4$Cl (100 mL). The solvent was removed in vacuo to afford material (8 g, 65%), which was not purified further.

MS (ES) m/z 197 (M+H)+.-

(e) 2-Oxo-2,3-dihydro-1H-pyrido[2,3-b][1,4]thiazine-7-carboxaldehyde

The alcohol (20d-Method B) (8 g, 40 mmole) was dissolved in 1:1 THF/CH$_2$Cl$_2$ (100 mL) and stirred with MnO$_2$ (36 g, 0.4 mole) at 60° C. for 24 hr. The mixture was filtered through celite®, and the filtrate was concentrated in vacuo to afford a solid (3.5 g, 44%).

MS (ES) m/z 195 (M+H)+.

(f) Title Compound

The aldehyde (20e) (0.098 g) was reacted with amine (1d) by the Method of Example (6d) to afford the free base as a foam (0.15 g)

δH (CD$_3$OD): 1.55 (2H, m), 1.96 (2H, br. d), 2.25 (2H, m) 2.45–2.80 (3H, m), 3.15 (2H, t), 3.60 (2H, s), 3.78 (2H, s), 3.95 (3H, s), 5.60 (1H, dd), 7.30 (1H, d), 7.42 (2H, m), 7.70 (1H, d), 7.90 (1H, d) 8.10 (1H, d), 8.68 (1H, d),

MS (+ve ion electrospray) m/z 480 (MH+).

The dioxalate salt was prepared by the same method as for Example 1.

Example 21

6-({1-[(R)-2-Hydroxy-2-(6-methoxy-quinolin-4-yl)-ethyl)-piperidin-4-ylamino}-methyl)-2-(R/S)-methyl-4H-benzo[1,4]thiazin-3-one dioxalate

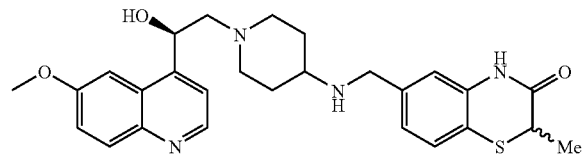

(a) 2-(R/S)-Methyl-3-oxo-3,4-dihydro-2H-benzo[1,4]thiazine-6-carboxylic acid ethyl ester 3-Amino-4-mercapto-benzoic acid ethyl ester zinc salt (2:1) (6.4 g) [prepared from 3,3'-dinitro-4,4'-disulfanediyl-di-benzoic acid diethyl ester (M. Fuson *J. Org. Chem.* 13, 690 (1948)) by reaction with zinc in acetic acid containing HCl in dioxan at room temperature] was reacted with chloroacetyl chloride by the method of Example (8b) to afford a solid (2.0 g) after chromatography on silica gel (chloroform).

MS (+ve ion electrospray) m/z 252 (MH+).

(b) 2-(R/S)-Methyl-3-oxo-3,4-dihydro-2H-benzo[1,4]thiazine-6-carboxylic acid The ester (21 a) (2.3 g) was hydrolysed with aqueous sodium hydroxide in tetrahydrofuran by the method of Example (6a) to afford a solid (1.95 g).

MS (−ve ion electrospray) m/z 222 (M−H−).

(c) 6-Hydroxymethyl-2-(R/S)-methyl-4H-benzo[1,4]thiazin-3-one

The carboxylic acid (21b) (1.95 g) was reacted with isobutylchloroformate and sodium borohydride by the method of Example (6b) to afford a solid (1.19 g).

MS (−ve ion electrospray) m/z 208 (M−H—).

(d) 2-(R/S)-Methyl-3-oxo-3,4-dihydro-2H-benzo[1,4]thiazine-6-carboxaldehyde The alcohol (21c) (1.15 g) was oxidised with manganese dioxide by the method of Example (6c) to afford a solid (0.95 g).

MS (−ve ion electrospray) m/z 206 (M−H−).

(e) Title Compound

The aldehyde (21d) (0.13 g) was reacted with amine (1d; 90% ee) by the Method of Example (6d) to afford the free base as a foam (0.10 g)

δH (CDCl$_3$): 1.45 (3H, d), 1.50 (2H, m), 1.90–2.70 (6H, m), 2.85 (2H, m), 3.30 (1H, m), 3.52 (1H, q), 3.80 (2H, s), 3.90 (3H, s), 5.41 (1H, dd), 6.85 (1H, s), 7.00 (1H, dd), 7.20 (1H, d) 7.25 (2H, m), 7.35 (1H, dd), 7.65 (1H, d), 8.05 (1H, d), 8.15 (1H, brs), 8.78 (1H, d)

MS (+ve ion electrospray) m/z 493 (MH+).

The dioxalate salt was prepared by the same method as for Example 1.

Example 22

7-Fluoro-6-{{1-[(R)-2-hydroxy-2-(6-methoxy-[1,5]naphthyridin-4-yl)ethyl]piperidin-4-ylamino}methyl}-4H-benzo[1,4]thiazin-3-one

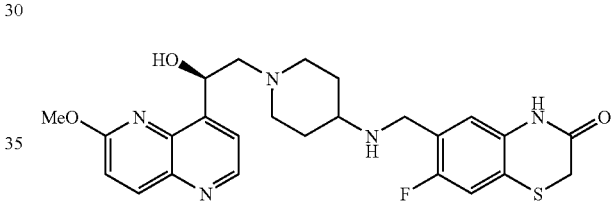

(a) 2,4-Difluoro-benzoic acid, ethyl ester

A solution of 2,4-difluoro-benzoic acid (19.3 g) in dry ethanol (200 ml) was treated with gaseous hydrochloric acid for 0.25 hours, then heated to reflux for 4 hours. Evaporation gave a white solid (22.7 g, 100%).

MS (APCI+) m/z 187 (MH+).

(b) 2,4-Difluoro-5-nitro-benzoic acid, ethyl ester

A solution of (22a) (5.33 g) in a mixture of concentrated nitric/sulphuric acids (4 ml/4 ml) was stirred at 0° C. for 2 hours, then partitioned between dichloromethane and water. The dichloromethane extract was washed with water, brine, dried and evaporated to give a white solid (5.0 g).

MS (APCI+) m/z 232 (MH+).

(c) 2-Fluoro-4-methoxycarbonylmethylsulfanyl-5-nitro-benzoic acid, ethyl ester A solution of (22b) (2.82 g, 12.2 mmol) in dichloromethane (50 ml) was treated with triethylamine (2 ml) then at 0° C. with methyl thioglycolate (1 ml). After 3 hours at 0° C. the mixture was evaporated and chromatographed eluting with an ethyl acetate/hexane gradient affording a yellow solid (2.05 g).

MS (APCI+) m/z 318 (ME+).

(d) 7-Fluoro-3-oxo-3,4-dihydro-2H-benzo[1,4]thiazine-6-carboxylic acid, ethyl ester A solution of (22c) (1.35 g, 4.3 mol) in acetic acid (50 ml) was treated with iron (2.4 g, 42.6 mmol) and heated at 60° C. for 3.5 hours. The mixture was filtered through Kieselguhr and partitioned between ethyl acetate and water. The organic extract was washed with water several times, dried and evaporated affording a white solid (1.02 g).
MS (APCI+) m/z 256 (MH+).

(e) 7-Fluoro-3-oxo-3,4-dihydro-2H-benzo[1,4]thiazine-6-carboxylic acid

A solution of (22d) (1 g, 4.2 mmol) in tetrahydrofuran/water (10 ml/10 ml) was treated with sodium hydroxide (0.34 g, 8.4 mmol) and stirred at room temperature for 7.5 hours. The mixture was acidified with 1M aqueous hydrochloric acid and evaporated to dryness giving a white solid.
MS m/z 226 (M–H).

(f) 7-Fluoro-6-hydroxymethyl-4H-benzo[1,4]thiazin-3-one

A suspension of acid (22e) (~4.2 mmol) in tetrahydrofuran (30 ml) was treated with triethylamine (0.7 ml, 5.03 mmol) then at 0° C. with isobutyl chloroformate (0.6 ml, 4.6 mmol). After 0.5 hour the mixture was filtered into a vigorously-stirred solution of sodium borohydride (0.48 g, 12.6 mmol) in ice/water (~10 ml). After 0.25 hour the mixture was acidified with 1M aqueous hydrochloric acid and extracted with ethyl acetate. Drying and evaporation afforded an oil (0.89 g).
MS (APCI+) m/z 214 (MH+).

(g) 7-Fluoro-3-oxo-3,4-dihydro-2H-benzo[1,4]thiazine-6-carboxaldehyde

A solution of (22f) (0.89 g) in dichloromethane/tetrahydrofuran (200 ml/20 ml) was treated with manganese dioxide (1.3 g, 14.7 mmol) then heated at 40° C. for 16 hours. The mixture was filtered through Kieselguhr and evaporated affording a brown solid (0.8 g) which was purified by chromatography on silica eluting with an ethyl acetate/hexane gradient giving a white solid (0.55 g).
MS (APCI+) m/z 212 (MH+).

(h) Title Compound

To a stirred solution of (R)-2-(4-aminopiperidin-1-yl)-1-(6-methoxy-[1,5]naphthyridin-4-yl)ethanol (2f) (0.30 g, 0.99 mmole) in CH$_2$Cl$_2$ (25 mL) and dry ethanol (10 mL) at RT was added the aldehyde (22 g) (0.20 g, 0.95 mmole) and granular Na$_2$SO$_4$ (approximately 200 mg). After 36 h, the reaction was filtered through a sintered-glass funnel and the filtrate was concentrated. The remaining residue was dissolved in dry ethanol and reacted with NaBH$_4$ (0.04 g, 1.0 mmole). After 12 h at RT, the reaction was concentrated under vacuum and the residue was dissolved in a mixture of H$_2$O (2 mL) and saturated aqueous NaHCO$_3$ (10 mL). The aqueous solution was extracted with EtOAc (2×50 mL) and the combined organic phases were washed with brine then were dried over Na$_2$SO$_4$. Flash chromatography on silica gel (9:1 CHCl$_3$/MeOH containing 5% NH$_4$OH) afforded the title compound (0.34 g, 70%) as light yellow solid:
MS (ES) m/z 498 (M+H)$^+$.

Example 23

(R)-2-{4-[(7-Fluoro-2,3-dihydrobenzo[1,4]dioxin-6-ylmethyl)amino]piperidin-1-yl}-1-(6-methoxy-[1,5]naphthyridin-4-yl)ethanol

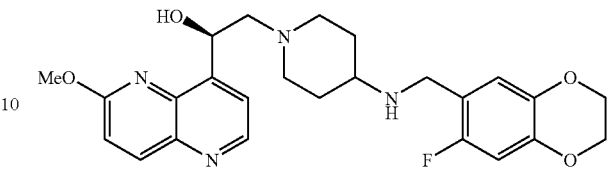

(a) 7-Fluoro-2,3-dihydro-benzo[1,4]dioxin-6-carboxaldehyde

A solution of 6-fluoro-2,3-dihydro-benzo[1,4]dioxine (prepared from 6-amino-2,3-dihydro-benzo[1,4]dioxine according to the procedure of V. Daukas, P. Gaidelis, R. Martinkus, S. Urboniene, Chemija, 1999, 10 (1), 59), (154 mg, 1 mmol) in dichloromethane (0.5 ml) was treated with dichloromethyl methyl ether (0.25 ml) at 0° C. under argon. Titanium tetrachloride (0.45 ml) in dichloromethane (0.5 ml) was added over 0.25 hours. The cooling bath was removed and the mixture was stirred at ambient temperature for 1 hour before being quenched with water and extracted with ether. The ether extract was washed with aqueous sodium bicarbonate and brine. Drying and evaporation afforded a brown oil which was purified by chromatography on silica (ethyl acetate/hexane) affording a clear oil (0.12 g).
MS (APCI+) m/z 183 (MH+).

(b) Title Compound

To a stirred solution of (R)-2-(4-aminopiperidin-1-yl)-1-(6-methoxy-[1,5]naphthyridin-4-yl)ethanol (2f) (0.30 g, 1.0 mmole) in CH$_2$Cl$_2$ (25 mL) and dry ethanol (10 mL) at RT was added aldehyde (23a) (0.18 g, 1.0 mmole) and granular Na$_2$SO$_4$ (approximately 200 mg). After 36 h, the reaction was filtered through a sintered-glass funnel and the filtrate was concentrated. The remaining residue was dissolved in dry ethanol and reacted with NaBH$_4$ (0.04 g, 1.0 mmole). After 12 h at RT, the reaction was concentrated under vacuum and the residue was dissolved in a mixture of H$_2$O (2 mL) and saturated aqueous NaHCO$_3$ (10 mL). The aqueous solution was extracted with EtOAc (2×50 mL) and the combined organic phases were washed with brine then were dried over Na$_2$SO$_4$. Flash chromatography on silica gel (9:1 CHCl$_3$/MeOH containing 5% NH$_4$OH) afforded the title compound (0.34 g, 73%) as a white solid:
MS (ES) m/z 469 (M+H)$^+$.

Example 24

(R)-2-{4-(2,3-Dihydro-[1,4]dioxino[2,3-c]pyridin-7-ylmethyl)amino]piperidin-1-yl}-1-(6-methoxy-[1,5]naphthyridin-4-yl)ethanol

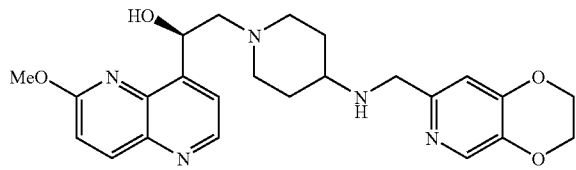

(a) 5-Benzyloxy-2-hydroxymethyl-1H-pyridin-4-one

A mixture of 5-benzyloxy-2-hydroxymethyl-4-pyrone (prepared from Kojic acid by the method of D. Erol, J. Med. Chem., 1994, 29, 893) (9.7 g, 40 mmol), concentrated aqueous (880) ammonia (100 ml), and ethanol (20 ml) was heated to reflux overnight. The mixture was allowed to cool to room temperature then filtered. The resultant solid was washed with ether and dried in vacuo (5.9 g).

MS (APCI+) m/z 232 (MH+).

(b) (2,3-Dihydro-[1,4]dioxino[2,3-c]pyridin-7-yl)-methanol

A solution of (24a) (2 g, 8.7 mmol) in water (220 ml) containing sodium hydroxide (17 mmol) was hydrogenated over 10% palladium on charcoal (1 g) for 4 hours. The mixture was filtered and evaporated to give a white solid. This solid was dissolved in N,N-dimethylformamide (8 ml) then treated with potassium carbonate (2.9 g) and 1,2-dibromoethane (0.6 ml, 7 mmol). The mixture was heated at 85° C. overnight. The cooled mixture was evaporated onto silica and chromatographed eluting with 10–30% methanol in ethyl acetate affording a white solid (250 mg, 21%).

MS (APCI+) m/z 168 (MH+).

(c) 2,3-Dihydro-[1,4]dioxino[2,3-c]pyridine-7-carboxaldehyde

A solution of (24b) (250 mg, 1.5 mmol) in dichloromethane (5 ml) was treated with manganese dioxide (650 mg, 7.5 mmol). After 3 days the mixture was filtered and evaporated affording a white solid (150 mg, 61%).

MS (APCI+) m/z 166 (MH+).

(d) Title Compound

To a stirred solution of (R)-2-(4-aminopiperidin-1-yl)-1-(6-methoxy-[1,5]naphthyridin-4-yl)ethanol (2f) (0.33 g, 1.1 mmole) in CH$_2$Cl$_2$ (25 mL) and dry ethanol (10 mL) at RT was added aldehyde (24c) (0.18 g, 1.1 mmole) and granular Na$_2$SO$_4$ (approximately 200 mg). After 36 h, the reaction was filtered through a sintered-glass funnel and the filtrate was concentrated. The remaining residue was dissolved in dry ethanol and reacted with NaBH$_4$ (0.04 g, 1.0 mmole). After 12 h at RT, the reaction was concentrated under vacuum and the residue was dissolved in a mixture of H$_2$O (2 mL) and saturated aqueous NaHCO$_3$ (10 mL). The aqueous solution was extracted with EtOAc (2×50 mL) and the combined organic phases were washed with brine then dried over Na$_2$SO$_4$. Flash chromatography on silica gel (9:1 CHCl$_3$/MeOH containing 5% NH$_4$OH) afforded the title compound (0.25 g, 55%) as a white solid:

MS (ES) m/z 452 (M+H)$^+$.

Example 25

(R)-1-(6-Methoxy-[1,5]naphthyridin-4-yl)-2-{4-[(5,6,7,8-tetrahydro-[1,8]naphthyridin-2-ylmethyl)amino]piperidin-1-yl}ethanol

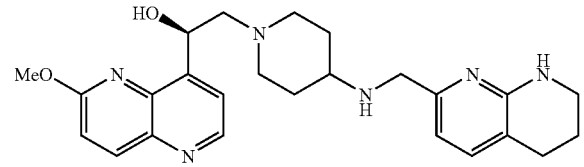

To a stirred solution of (R)-2-(4-aminopiperidin-1-yl)-1-(6-methoxy-[1,5]naphthyridin-4-yl)ethanol (2f) (0.30 g, 1.0 mmole) in CH$_2$Cl$_2$ (25 mL) and dry ethanol (10 mL) at RT was added 5,6,7,8-tetrahydro-[1,8]naphthyridine-2-carboxaldehyde (prepared according to the procedure of WO 98/08840, 0.17 g, 1.0 mmole) and granular Na$_2$SO$_4$ (approximately 200 mg). After 36 h, the reaction was filtered through a sintered-glass funnel and the filtrate was concentrated. The remaining residue was dissolved in dry ethanol and reacted with NaBH$_4$ (0.04 g, 1.0 mmole). After 12 h at RT, the reaction was concentrated under vacuum and the residue was dissolved in a mixture of H$_2$O (2 mL) and saturated aqueous NaHCO$_3$ (10 mL). The aqueous solution was extracted with EtOAc (2×50 mL) and the combined organic phases were washed with brine then were dried over Na$_2$SO$_4$. Flash chromatography on silica gel (9:1 CHCl$_3$/MeOH containing 5% NH$_4$OH) afforded the title compound (0.37 g, 83%) as a white solid:

MS (ES) m/z 449 M+H)$^+$.

$^1$H NMR (400 MHz, CDCl$_3$) δ 8.77 (d, J=4.5 Hz, 1H), 8.21 (d, J=9.0 Hz, 1H), 7.80 (d, J=4.5 Hz, 1H), 7.12 (m, 2H), 6.47 (d, J=7.3 Hz, 11H), 5.74 (m, 1H), 4.77 (br s, 1H), 4.04 (s, 3H), 3.70 (s, 2H), 3.38 (m, 2H), 3.24 (m, 1H), 3.08 (m, 1H), 2.79 (m, 2H), 2.71 (t, J=6.3 Hz, 2H), 2.57 (m, H), 2.40 (m, 2H), 2.17 (m, 1H), 1.91 (br m, 2H).

Example 26

(R)-1-(6-Methoxyquinolin-4-yl)-2-{4-[(5,6,7,8-tetrahydro-[1,8]naphthyridin-2-ylmethyl)amino]piperidin-1-yl}ethanol

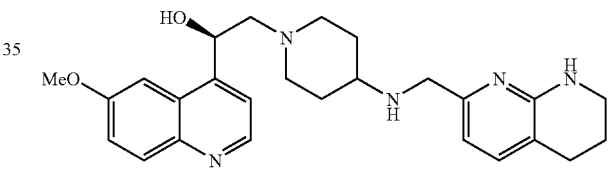

To a stirred solution of the mono hydrochloride salt of (R)-2-(4-aminopiperidin-1-yl)-1-(6-methoxyquinolin-4-yl)ethanol (1d) (0.34 g, 1.0 mmole) in CH$_2$Cl$_2$ (25 mL) and dry ethanol (10 mL) at RT was added 5,6,7,8-tetrahydro[1,8]naphthyridine-2-carboxaldehyde (prepared according to the procedure of WO 98/08840, 0.17 g, 1.0 mmole), triethylamine (0.10 g, 1.0 mmole), and granular Na$_2$SO$_4$ (approximately 200 mg). After 36 h, the reaction was filtered through a sintered-glass funnel and the filtrate was concentrated. The remaining residue was dissolved in dry ethanol and reacted with NaBH$_4$ (0.04 g, 1.0 mmole). After 12 h at RT, the reaction was concentrated under vacuum and the residue was dissolved in a mixture of H$_2$O (2 mL) and saturated aqueous NaHCO$_3$ (10 mL). The aqueous solution was extracted with EtOAc (2×50 mL) and the combined organic phases were washed with brine then were dried over Na$_2$SO$_4$. Flash chromatography on silica gel (9:1 CHCl$_3$/MeOH containing 5% NH$_4$OH) afforded the title compound (0.31 g, 69%) as a white solid:

MS (ES) m/z 448 (M+H)$^+$.

$^1$H NMR (400 MHz, CDCl$_3$) δ 8.77 (d, J=4.5 Hz, 1H), 8.03 (d, J=9.2 Hz, 1H), 7.64 (d, J=4.5 Hz, 1H), 7.35 (d, J=6.6 Hz, 1H), 7.18 (m, 1H), 7.10 (d, J=7.0 Hz, 1H), 6.46 (d, J=7.3 Hz, 1H), 5.42 (m, 1H), 4.77 (m, 1H), 3.93 (s, 3H), 3.70 (s, 2H), 3.38 (m, 2H), 3.20 (m, 1H), 2.83 (m, 2H), 2.71 (t, J=6.3 Hz, 2H), 2.58 (m, 1H), 2.47 (m, 1H), 2.40 (m, 1H), 2.20 (m, 1H), 1.91 (br m, 2H).

Example 27

6-[({(3S,4S)-3-Hydroxy-1-[(R)-2-hydroxy-2-(6-methoxyquinolin-4-yl)-ethyl]piperidin-4-ylamino}methyl)4H-benzo[1,4]thiazin-3-one and 6-[({(3R,4R)-3-Hydroxy-1-[(R)-2-hydroxy-2-(6-methoxyquinolin-4-yl)-ethyl]piperidin-4-ylamino}methyl)-4H-benzo[1,4]thiazin-3-one

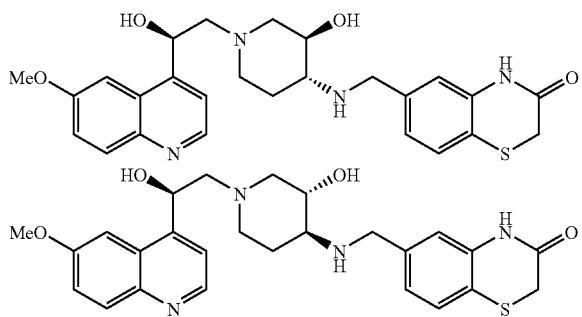

(a) tert-Butyl 3,6-dihydro-2H-pyridine-1-carboxylate 1,2,3,6-tetrahydropyridine (15.0 g, 180 mmole) was added to a 10% aqueous solution of $Na_2CO_3$ (50 mL) and the solution was cooled to 0° C. Di-tert-butyl dicarbonate (39.8 g, 182 mmole) was added in portions over 15 min with vigorous stirring. The solution was stirred at 0° C. for 1 hr and then warmed to room temperature and stirred for an additional 18 hr. The reaction solution was partitioned between $Et_2O$ and saturated NaCl solution. The ether layer was dried over $Na_2SO_4$ and concentrated in vacuo to give an oil (31.80 g, 96%), which needed no further purification.

MS (ES) m/z 184 (M+H)$^+$.

(b) tert-Butyl 7-oxa-3-aza-bicyclo[4.1.0]heptane-3-carboxylate

A solution of (27a) (15.0 g, 81.9 mmole) in $CH_2Cl_2$ (150 mL) was treated with a solution of metachloroperbenzoic acid (18.36 g, 106.4 mmole) in $CH_2Cl_2$ (300 mL) which was added over 30 minutes at 0° C. The solution was allowed to warm to room temperature and stirred for 18 hr. The reaction solution was washed with 5% aqueous $K_2CO_3$ and saturated NaCl solution, then dried over $Na_2SO_4$ and concentrated in vacuo to yield an off-white solid. This was flash chromatographed on silica gel (20% EtOAc/hexanes) to yield a white solid (12.80 g, 78%).

MS (ES) m/z 200 (M+H)$^+$.

(c) tert-Butyl (±)-trans-4-benzylamino-3-hydroxypiperidine-1-carboxylate

The ester (27b) (13.24 g, 66.5 mmole) was combined with benzylamine (14.53 mL, 133 mmole) and stirred while heating at 115° C. The reaction was allowed to stir for 8 hr at 115° C. and then allowed to cool to ambient temperature. EtOAc was added and the organic layer was washed sequentially with $H_2O$ and saturated NaCl solution. The organic layer was dried over $Na_2SO_4$ and concentrated to yield a yellow solid (19.31 g, 95%): LCMS: m/z 307 (M+H)$^+$. This mixture of regioisomers was chromatographed (preparative HPLC) on Lichrosphere silica gel 60A; 12 u, 100 mm ID×250 mm L; 70:30:0.5 hexanes:THF:diethylamine; 500 mL/min; uv detection 254 nm; 4.5 g mixture per injection. The products, tert-butyl (±)-trans-3-benzylamino-4-hydroxy-piperidine-1-carboxylate and tert-butyl (±)-trans-4-benzylamino-3-hydroxy-piperidine-1-carboxylate, as assigned by NMR, were obtained in a 3:1 ratio with retention times of 8.4 min and 6.5 min, respectively.

(d) tert-Butyl (±)-trans-4-amino-3-hydroxypiperidine-1-carboxylate

A solution of the ester (27c) (0.5 g, 1.63 mmole) in EtOH (40 mL) was treated with 10% palladium on carbon (catalytic) and hydrogenated in a Parr bottle for 6 hr at 40 psi. The solution was filtered through a plug of celite®, and the filter pad was washed with EtOH. The filtrate was concentrated to yield a yellow oil (0.35 g, 99%). No further purification was required.

MS (ES) m/z 217 (M+H)$^+$.

(e) tert-Butyl (±)-trans-3-hydroxy-4-[(3-oxo-3,4-dihydro-2H-benzo[1,4]thiazin-6-ylmethyl)amino]piperidine-1-carboxylate A solution of amine (27d) (0.35 g, 1.62 mmole) in $CH_2Cl_2$ (10 mL) was treated with 3-oxo-3,4-dihydro-2H-benzo[1,4]thiazine-6-carboxaldehyde (6c) (0.34 g, 1.78 mmole). The solution was sonicated for 5 min and then allowed to stir at ambient temperature for 5 hr. $Na(OAc)_3BH$ (0.52 g, 2.43 mmole) was added and the solution was stirred at ambient temperature for 2 hr. The reaction was diluted with EtOAc and washed with saturated aqueous $NaHCO_3$ solution, $H_2O$, and saturated aqueous NaCl solution. The organic layer was dried over $Na_2SO_4$ and concentrated to yield an off-white solid. This was flash chromatographed on silica gel (90:10:1 $CHCl_3/MeOH/NH_4OH$) to yield a white solid (0.31 g, 48%).

MS (ES) m/z 394 (M+H)$^+$.

(f) (±)-trans-3-Hydroxy-4-[(3-oxo-3,4-dihydro-2H-benzo[1,4]thiazin-6-ylmethyl)amino]piperidine A solution of (27e) (0.30 g, 0.76 mmole) in $CH_2Cl_2$ (3 mL) was treated with 4.0 N HCl/dioxane (5 mL). The solution was allowed to stir for 30 min and then concentrated. MeOH was added and the solution was again concentrated to remove any excess HCl. The remaining solid was dissolved in MeOH (5 mL) and treated with MP-Carbonate resin (1.00 g, 2.87 mmole). The solution was then filtered and concentrated to yield a white solid, (0.24 g, 100%). No further purification was necessary.

MS (ES) m/z 294 (M+H)$^+$.

(g) Title Compound

A solution of the amine (27f) (0.23 g, 0.784 mmole) in DMF (4 mL) was treated with the oxirane (1b) (0.158 g, 0.784 mmole) and $LiClO_4$ (0.083 g, 0.784 mmole and stirred at 100° C. for 16 hr. EtOAc was added after cooling to room temperature and the solution was washed with water (3×) and saturated aqueous NaCl solution. The organic layer was dried over $Na_2SO_4$ and concentrated to yield an oil. This was flash chromatographed on silica gel (90:10:1 $CHCl_3/MeOH/NH_4OH$) to yield the title compound as a 1:1 diastereomeric mixture (0.217 g, 56%), as a tan solid.

MS (ES) m/z 495 (M+H)$^+$.

49

The individual diastereomers of the 1:1 mixture were separated via HPLC on a Chiralcel OD column, 250×20 mm ID; 75:25:0.1-hexanes:ethanol:diethylamine; 17.5 mL/min; uv detection at 214 & 254 nm; retention times of 11.6 min and 17.9 min.

Example 28

7-{{1-[(R)-2-Hydroxy-2-(6-methoxy-[1,5]naphthyridin-4-yl)ethyl]piperidin-4-ylamino}methyl}-1H-pyrido[2,3-b][1,4]thiazin-2-one

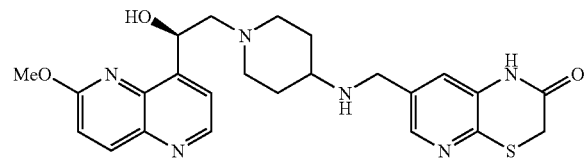

A solution of (R)-2-(4-aminopiperidin-1-yl)-1-(6-methoxy-[1,5]naphthyridin-4-yl)ethanol (2f) (0.1 g, 0.33 mmole) and aldehyde (20e) (65 mg, 0.3 mmole) in CH$_2$Cl$_2$ (5 mL) and MeOH (15 mL) was treated with 3 Å molecular sieves, and the mixture was stirred at room temperature for 18 hr. NaBH$_4$ (18 mg, 0.48 mmole) was added portionwise, and the resulting mixture was stirred for an additional 3 hr, then was filtered. The filtrate was concentrated to dryness in vacuo, and the residue was partitioned between H$_2$O and CHCl$_3$. The mixture was made acidic with 2 M HCl, then was made basic with NaHCO$_3$. Extraction with CHCl$_3$, drying (Na$_2$SO$_4$), and concentration in vacuo left a residue that was purified by flash chromatography on silica gel (MeOH/CH$_2$Cl$_2$). The title compound (0.04 g, 27%) was obtained as a foam.

MS (ES) m/z 481 (M+H)$^+$.

Example 29

7-{{1-[(R)-2-Hydroxy-2-(6-methoxyquinolin-4-yl)ethyl]piperidin-4-ylamino}methyl}-2,3-dihydro-5H-benzo[b][1,4]thiazepine-4-one, diacetate

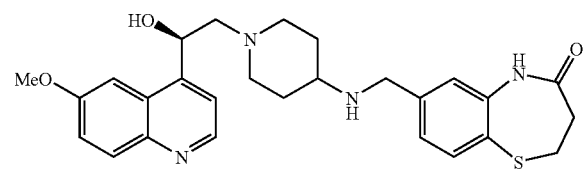

(a) Methyl 3-(4-formyl-2-nitrophenylsulfanyl)propionate

To a solution of 4-chloro-3-nitrobenzaldehyde (2.60 g, 0.014 mole) and methyl 3-mercaptopropionate (1.92 g, 0.016 mole) in DMF (10 mL) was added anhydrous K$_2$CO$_3$ (2.07 g, 0.016 mole). After stirring at ambient temperature for 16 hr, the reaction was quenched with ice water. The precipitated product was collected by suction filtration, washed well with water, and dried in vacuo to give a bright yellow solid (3.65 g, 97%).

MS (ES) m/z 270.1 (M+H)$^+$.

50

(b) 4-Oxo-2,3,4,5-tetrahydrobenzo[b][1,4]thiazepine-7-carboxaldehyde

To a solution of the ester (29a) (3.65 g, 0.014 mole) in glacial AcOH (100 mL) was added iron powder (7.9 g, 0.141 g atom). After heating at 60° C. for 12 hr, the warm mixture was filtered and the filtrate was concentrated under reduced pressure. The residue was partitioned between EtOAc and aqueous NaCl, and the organic layer was dried (MgSO$_4$). Purification by flash column chromatography on silica gel (gradient elution: 4:1, 2:1, 1:1 EtOAc/hexanes) yielded a light yellow solid (0.553 g, 20%).

MS (ES) m/z 208.0 (M+H)$^+$.

(c) Title Compound

A solution of the aldehyde (29b) (0.104 g, 0.50 mmole) and (R)-2-(4-aminopiperidin-1-yl)-1-(6-methoxyquinolin-4-yl)ethanol (1d) (0.162 g, 0.54 mmole) were stirred together in 1:1 MeOH/dichloroethane (1.5 mL) at ambient temperature for 24 hr. The intermediate imine was treated with NaBH$_4$ (0.093 g, 2.46 mmole) and the reaction was stirred for an additional 16 hr. The solvents were removed under reduced pressure and the residue was partitioned between CH$_2$Cl$_2$ and aqueous NaCl, and the organic layer was dried (MgSO$_4$). Purification by flash column chromatography on silica gel (gradient elution: 1:9 to 1:4 MeOH/CH$_2$Cl$_2$ with 1% glacial AcOH) yielded the title compound (37.4 mg, 15%) as an amorphous yellow solid.

MS (ES) m/z 493.2 (M+H)$^+$.

Example 30

6-{{1-[(R)-2-Hydroxy-2-(6-methoxy-[1,5]naphthyridin-4-yl)ethyl]piperidin-4-ylamino}methyl}-4H-pyrido[3,2-b][1,4]oxazin-3-one, dihydrochloride

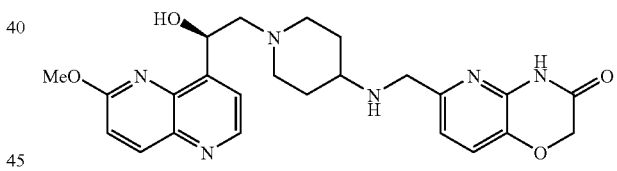

(a) 2-Bromo-5-hydroxy-6-nitropyridine

3-Hydroxy-2-nitropyridine (20 g, 0.143 mole) was dissolved in methanol (400 mL) and a solution of 25% sodium methoxide in methanol (33 mL, 0.13 mole) was added at room temperature. The mixture was stirred for 30 min, then was cooled to 0° C., and bromine (7.2 mL, 0.14 mole) was added slowly. The reaction was then stirred at 0° C. for 30 min, then was quenched with glacial AcOH (2.5 mL). The solvent was removed in vacuo to afford material (30 g, 96%), which was used without further purification.

MS (ES) m/z 219.0 (M+H)$^+$.

(b) Ethyl (6-bromo-2-nitro-pyridin-3-yloxy)acetate

The hydroxypyridine (30a) (30 g, 0.14 mole) was suspended in acetone (200 mL), and potassium carbonate (39 g, 0.28 mole) was added, followed by ethyl bromoacetate (15.7 mL, 0.14 mmole). The reaction was heated at reflux for 10 hr, then was cooled to room temperature and diluted with Et₂O. The precipitate was removed by suction filtration, and the filtrate was concentrated in vacuo to afford material (38 g, 89%), which was used without further purification.

MS (ES) m/z 305.0 (M+H)⁺.

(c) 6-Bromo-4H-pyrido[3,2-b][1,4]oxazin-3-one

The nitropyridine (30b) (38 g, 0.125 mole) was dissolved in glacial AcOH (150 mL), and iron powder (20 g, 0.36 mole) was added. The mixture was mechanically stirred and heated at 90° C. for 5 hr, then was cooled to room temperature and diluted with EtOAc (300 mL). The mixture was filtered through a pad of silica gel and the filtrate was concentrated in vacuo and the residue recrystallized from MeOH (15 g, 52%).

MS (ES) m/z 229.0 (M+H)⁺.

(d) 6-((E)-Styryl)-4H-pyrido[3,2-b][1,4]oxazin-3-one

The bromopyridine (30c) (6.0 g, 26.3 mmole) and trans-2-phenylvinylboronic acid (3.9 g, 26.3 mmole) were dissolved in 1,4-dioxane (150 mL) and the solution was degassed with argon. (Ph₃P)₄Pd (230 mg, 0.2 mmole) was added, followed by a solution of potassium carbonate (6.9 g, 50 mmole) in H₂O (20 mL). The reaction was heated at reflux under argon overnight, then was cooled to room temperature and diluted with EtOAc (200 mL). The solution was washed sequentially with H₂O and brine, dried (Na₂SO₄), and concentrated in vacuo. The solid residue was purified by flash chromatography on silica gel (5–10% EtOAc/CHCl₃) to afford a solid (2.5 g, 38%).

MS (ES) m/z 253.0 (M+H)⁺.

(e) 3-Oxo-3,4-dihydro-2H-pyrido[3,2-b][1,4]oxazine-6-carboxaldehyde

The pyridine (30d) (1.2 g, 4.8 mmole) was dissolved in CH₂Cl₂ (200 mL) and the solution was cooled to −78° C. Ozone was bubbled through the solution with stirring until a pale blue color appeared, then the excess ozone was removed by bubbling oxygen through the solution for 15 min. Dimethylsulfide (1.76 mL, 24 mmole) was added to the solution, and the reaction was stirred at −78° C. for 3 hr, then at room temperature overnight. The solvent was removed in vacuo, and the residue was triturated with Et₂O (50 mL). The collected solid was washed with additional Et₂O and dried to afford a solid (700 mg, 82%).

MS (ES) m/z 179.0 (M+H)⁺.

(f) Title Compound (R)-2-(4-Amino-piperidin-1-yl)-1-(6-methoxy-[1,5]naphthyridin-4-yl)-ethanol (2f) (254 mg, 0.84 mmole), aldehyde (30e), (150 mg, 0.84 mmole), and a catalytic amount of 4 Å molecular sieves were combined in DMF (2 mL), and the mixture was stirred overnight. MeOH (3 mL) and sodium borohydride (48 mg, 1.26 mmole) were added, and the reaction mixture was stirred at room temperature for 2 hr. The solvent was removed in vacuo, and the residue was dissolved in a mixture of 1:2 MeOH/EtOAc (5 mL). A solution of HCl in Et₂O (1.0 M, 1.7 mL, 1.7 mmole) was added, and the precipitated solid was collected, washed with EtOAc, and dried to afford the title compound (75 mg, 17%).

MS (ES) m/z 465.0(M+H)⁺.

¹H NMR (400 MHz, CD₃OD) δ 8.80 (d, J=4.6 Hz, 1H), 8.24 (d, J=9.1 Hz, 1H), 7.94 (d, J=4.6 Hz, 1H), 7.38 (d, J=8.0 Hz, 1H), 7.27 (d, J=9.1 Hz, 1H), 7.13 (d, J=8.0 Hz, 1H), 6.20 (d, J=9.3 Hz, 1H), 4.70 (s, 2H), 4.34 (s, 2H), 4.21 (m, 1H), 4.14 (s, 3H), 3.51–3.81 (m, 3H), 3.16–3.39 (m, 3H), 2.40–2.54 (m, 2H), 2.20–2.45 (m, 2H)

Example 31

6-{{1-[(R)-2-Hydroxy-2-(6-methoxy-[1,5]naphthyridin-4-yl)ethyl]piperidin-4-ylamino}methyl}4H-pyrido[3,2-b][1,4]thiazin-3-one, hydrochloride

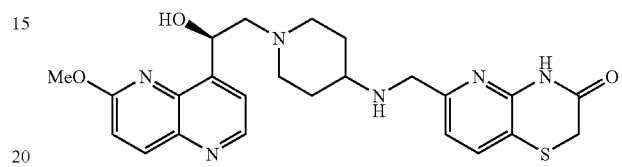

(a) Methyl 3-oxo-3,4-dihydro-2H-pyrido[3,2-b][1,4]thiazine-6-carboxylate

A solution of ethyl 2-mercaptoacetate (1.473 ml) in DMF (48 ml) was ice-cooled and treated with sodium hydride (540 mg of a 60% dispersion in oil). After 1 hour methyl 6-amino-5-bromopyridine-2-carboxylate (3 g) (T. R. Kelly and F. Lang, J. Org. Chem. 61, 1996, 4623–4633) was added and the mixture stirred 16 hours at room temp. The solution was diluted with EtOAc (1 liter), washed with water (3×300 ml), dried and evaporated to about 10 ml. The white solid was filtered off and washed with a little EtOAc to give a solid (0.95 g).

MS (APCI⁻) m/z 223 ([M−H]⁻, 100%)

(b) 3-Oxo-3,4-dihydro-2H-pyrido[3,2-b][1,4]thiazine-6-carboxylic acid

A solution of the ester (31a) (788 mg) in dioxan (120 ml)/water (30 ml) was treated dropwise over 2 hours with 0.5M NaOH solution (8 ml) and stirred overnight. After evaporation to approx. 3 ml, water (5 ml) was added and 2N HCl to pH4. The precipitated solid was filtered off, washed with a small volume of water and dried under vacuum to give a solid (636 mg).

MS (APCI⁻) m/z 209 ([M−H]⁻, 5%), 165([M—COOH]⁻, 100%)

(c) 6-Hydroxymethyl-3-oxo-3,4-dihydro-2H-pyrido[3,2-b][1,4]thiazine

A solution of the carboxylic acid (31 b) (500 mg) in THF (24 ml) with triethylamine (0.396 ml) was cooled to −10° C. and isobutyl chloroformate (0.339 ml) added. After 20 mins. at this temp. the suspension was filtered through kieselguhr into an ice-cooled solution of sodium borohydride (272 mg) in water (8 ml), the mixture stirred 30 mins. and the pH reduced to 7 with dilute HCl. Solvent was evaporated and the residue triturated under water. The solid was filtered and dried under vacuum to give a white solid (346 mg).

MS (APCI⁻) m/z 195 ([M−H]⁻, 50%), 165(100%)

(d) 3-Oxo-3,4-dihydro-2H-pyrido[3,2-b][1,4]thiazine-6-carboxaldehyde

A solution of the alcohol (31 c) (330 mg) in dichloromethane (30 ml)/THF (30 ml) was treated with manganese dioxide (730 mg) and stirred at room temp. Further manganese dioxide was added after 1 hour (730 mg) and 16 hours (300 mg). After a total of 20 hours the mixture was filtered through kieselguhr and the filtrate evaporated. The solid was triturated under EtOAc/hexane 1:1 and filtered off to give a solid (180 mg).

MS (APCI$^-$) m/z 195 ([M–H]$^-$, 95%), 165(100%)

(e) Title Compound

To a stirred solution of (R)-2-(4-aminopiperidin-1-yl)-1-(6-methoxy-[1,5]naphthyridin-4-yl)ethanol (2f) (0.234 g, 0.77 mmole) in CH$_2$Cl$_2$ (3 mL) and dry methanol (3 mL) at RT was added the aldehyde (31d) (0.100 g, 0.52 mmole), and granular Na$_2$SO$_4$ (approximately 200 mg). After 12 h NaBH$_4$ (0.08 g, 2.0 mmole) was added and the mixture was stirred for 4 hours, then poured into saturated aqueous sodium bicarbonate solution (10 mL) and extracted with chloroform (3×10 mL). The combined organic phases were dried over Na$_2$SO$_4$, filtered, and concentrated. The residue was dissolved in methanol (3 mL) and diluted with ethyl acetate (3 mL). While stirring a solution of 1.0 M HCl in ether (0.5 mL) was added dropwise. The product was collected by suction filtration, washed with ethyl acetate then Et$_2$O, and dried under vacuum to afford the monohydrochloride salt of the title compound (0.150 g, 57%) as an off-white solid.

MS (ES) m/z 481 (M+H)$^+$.

Example 32

(R)-2-{4-[(3,4-Dihydro-2H-pyrido[3,2-b[1,4]oxazin-6-ylmethyl)-amino]-piperidin-1-yl}-1-(6-methoxy-[1,5]naphthyridin-4-yl}-ethanol, hydrochloride

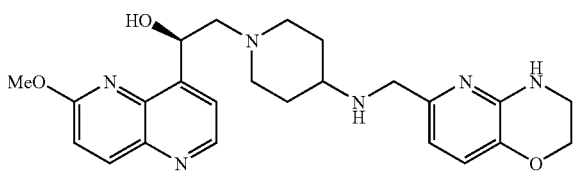

(a) 6-((E)-Styryl)-3,4-dihydro-2H-pyrido[3,2-b][1,4]oxazine 6-((E)-Styryl)-4H-pyrido[3,2-b][1,4]oxazin-3-one (30d) (350 mg, 1.54 mmole), was dissolved in anhydrous THF (10 mL) and the solution was cooled to 0° C. A solution of LiAlH$_4$ in THF (1.0 M, 1.54 mL, 1.54 mmole) was added dropwise at 0° C. The reaction was then warmed to room temperature and stirred for 2 hr. H$_2$O (0.06 mL) was added dropwise and mixture was stirred for 5 min, then 15% sodium hydroxide (0.06 mL) was added followed by H$_2$O (0.18 mL). The mixture was stirred overnight, then was diluted with Et$_2$O and filtered through celite®. The filtrate was concentrated and the residue was purified by flash chromatography on silica gel (5% EtOAc/CHCl$_3$) to afford the product (200 mg, 55%).

MS (ES) m/z 239.0 (M+H)$^+$.

(b) 3,4-Dihydro-2H-pyrido[3,2-b][1,4]oxazine-6-carboxaldehyde

OsO$_4$ (4% solution in water, 0.25 mL), H$_2$O (1 mL), and sodium periodate (539 mg, 2.5 mmole) were added to a solution of the pyridooxazine (32a) (200 mg, 0.84 mmole) in 1,4-dioxane (5 mL). The reaction was stirred at room temperature for 5 hr, then was diluted with H$_2$O (5 mL). The mixture was extracted with chloroform, and the combined organic layers were concentrated in vacuo. The residue was purified by flash chromatography on silica gel (5% EtOAc/CHCl$_3$) to afford the product (65 mg, 47%).

MS (ES) m/z 165.0 (M+H)$^+$.

(c) Title Compound (R)-2-(4-Aminopiperidin-1-yl)-1-(6-methoxy-[1,5]naphthyridin-4-yl)ethanol (2f) (111 mg, 0.37 mmole), aldehyde (32b) (55 mg, 0.33 mmole), and anhydrous Na$_2$SO$_4$ powder (a catalytic amount) were combined in CH$_2$Cl$_2$ (2 mL), and the mixture was stirred overnight. MeOH (3 mL) and NaBH$_4$ (13 mg, 0.33 mmole) were added, and the reaction was stirred at room temperature for 2 hr. The solvent was removed in vacuo, and the residue was partitioned between H$_2$O and CHCl$_3$. The organic layer was washed with brine and dried (Na$_2$SO$_4$). The solvent was removed in vacuo, and the residue was dissolved in a mixture of 1:2 MeOH/EtOAc (3 mL). A solution of HCl in Et$_2$O (1.0 M, 0.33 mL, 0.33 mmole) was added, and the precipitated solid was collected, washed with EtOAc, and dried to afford the title compound (40 mg, 25%).

$^1$H NMR (400 MHz, CD$_3$OD) δ 9.04 (d, J=5.4 Hz, 1H), 8.42 (d, J=9.3 Hz, 1H), 8.33 (d, J=5.3 Hz, 1H), 7.55 (d, J=9.3 Hz, 1H), 7.23 (d, J=7.8 Hz, 1H), 6.89 (d, J=7.9 Hz, 1H), 6.33 (d, J=8.4 Hz, 1H), 4.35 (s, 2H), 4.21 (s, 3H), 4.15 (m, 1H), 3.51–3.85 (m, 6H), 3.30–3.58 (m, 4H), 2.40–2.54 (m, 2H), 2.20–2.40 (m, 2H).

MS (ES) m/z 451.0 (M+H)$^+$.

Example 33

7-Bromo-6-{{1-[(R)-2-hydroxy-2-(6-methoxy-[1,5]naphthyridin-4-yl)ethyl]piperidin-4-ylamino}methyl}4H-pyrido[3,2-b][1,4]thiazin-3-one

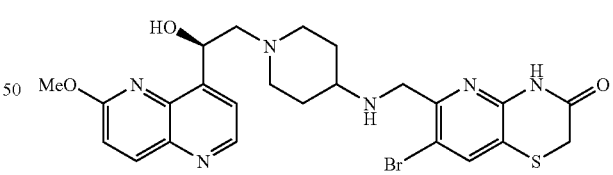

(a) Methyl 6-amino-3,5-dibromopyridine-2-carboxylate

A solution of methyl 6-amino-3-bromopyridine-2-carboxylate (20.62 g) (T. R. Kelly and F. Lang, J. Org. Chem. 61, 1996, 4623–4633) in chloroform (570 ml) was treated dropwise over 2 hours with bromine (4.62 ml) in chloroform (115 ml) and stirred 16 hours. The solution was washed with excess aqueous sodium bicarbonate, dried and evaporated. Crystallisation from EtOAc/hexane gave a solid (13.5 g).

MS (APCI$^+$) m/z 309, 311, 313 (MH$^+$, 70%), 295, 297, 299 (100%)

(b) Methyl 7-bromo-3-oxo-3,4-dihydro-2H-pyrido[3,2-b][1,4]thiazine-6-carboxylate This was prepared from (33 a) (12.75 g), analogously to methyl 3-oxo-3,4-dihydro-2H-pyrido[3,2-b][1,4]thiazine-6-carboxylate (Example 31a). Yield 5.85 g.

MS (APCI$^+$) m/z 303, 305 (MH$^+$, 30%), 271, 273 (100%)

(c) 7-Bromo-3-oxo-3,4-dihydro-2H-pyrido[3,2-b][1,4]thiazine-6-carboxylic acid This was prepared from (33b) analogously to 3-oxo-3,4-dihydro-2H-pyrido[3,2-b][1,4]thiazine-6-carboxylic acid (Example 31b) (73%).

MS (APCI$^-$) m/z 287, 289 ([M−H]$^-$, 3%), 243, 245 ([M—COOH]$^-$, 100%)

(d) 7-Bromo-6-hydroxymethyl-3-oxo-3,4-dihydro-2H-pyrido[3,2-b][1,4]thiazine

This was prepared from (33c) analogously to 6-hydroxymethyl-3-oxo-3,4-dihydro-2H-pyrido[3,2-b][1,4]thiazine (Example 31c) (80%).

MS (APCI$^+$) m/z 275, 277 (M+, 20%), 257, 259 (100%)

(e) 7-Bromo-3-oxo-3,4-dihydro-2H-pyrido[3,2-b][1,4]thiazine-6-carboxaldehyde A mixture of the alcohol (33d) (518 mg), manganese dioxide (870 mg), THF (45 ml) and 1,2-dichloroethane (45 ml) was heated at 60° C. under argon. Further manganese dioxide was added after 4 hours (870 mg) and 20 hours (600 mg). After a total of 30 hours filtration through kieselguhr and evaporation of solvent gave the product (320 mg).

MS (APCI$^-$) m/z 271, 273 ([M−H]$^-$, 40%), 152 (100%)

(f) Title Compound

A solution of (R)-2-(4-aminopiperidin-1-yl)-1-(6-methoxyquinolin-4-yl)ethanol (1d) (55 mg, 0.138 mmole) in CH$_2$Cl$_2$ (2 mL) and EtOH (0.2 mL) was treated with anhydrous Na$_2$SO$_4$ (100 mg) and aldehyde (33e) (50 mg, 0.18 mmole). The resulting solution was stirred at room temperature for 14 hr, then sodium triacetoxy borohydride (57 mg, 0.27 mmole) was added. The resulting slurry was stirred at room temperature for a further 10 hr, then was quenched by the addition of water (2 mL) and the volatiles were removed in vacuo. The residue was partitioned between EtOAc (2×20 mL) and brine (5 mL). The organic phases were combined, dried (MgSO$_4$), and concentrated in vacuo. The resulting oil was purified by flash chromatography on silica gel (gradient: 0–10% MeOH/CH$_2$Cl$_2$) to afford the title compound (35 mg, 35%) as a colorless oil.

$^1$H NMR (400 MHz, CDCl$_3$) δ 8.69 (d, 1H), 8.21 (d, 1H), 7.81 (d, 1H), 7.76 (s, 1H), 7.12 (d, 1H), 5.21–5.30 (dd, 1H), 4.16 (s, 3H), 3.96 (s, 2H), 3.29–3.39 (m, 1H), 3.08–3.15 (dd, 1H), 2.29–2.61 (m, 4H), 1.50–2.5 (m, 8H).

MS (ES) m/z 559, 561 (M+H)$^+$.

Example 34

7-{{1-[(R)-2-Hydroxy-2-(6-methoxy-[1,5]naphthyridin-4-yl)ethyl]piperidin-4-ylamino}methyl}-1H-pyrido[3,4-b][1,4]thiazin-2-one

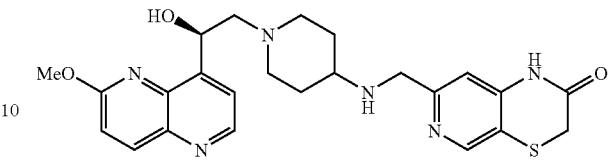

(a) 5-Fluoro-2-picoline N-oxide

Preparation of 5-fluoro-2-picoline was based on E. J. Blanz, F. A. French, J. R. DoAmaral and D. A. French, J. Med. Chem. 1970, 13, 1124–1130. 5-Amino-2-picoline (12.5 g) in ethanol (105 ml) and 50% fluoroboric acid (44.5 ml) was stirred at −5° C. and treated dropwise over 45 mins. with n-butyl nitrite (31.25 ml). The solution was maintained at this temp. for 3 hours, treated with ether (100 ml, precooled to −20° C.) and the solid filtered off, quickly transferred to a flask and covered with hexane (precooled to −20° C.). After allowing to warm to approx. 20° C. and standing for 3 days the hexane was decanted and 2M NaOH solution added until basic (pH10). The mixture was filtered and the filtrate extracted with dichloromethane (10×200 ml). The organic solution was dried, evaporated to 200 ml and treated with m-chloroperbenzoic acid (26.5 g). After stirring 16 hours the solution was washed with excess aqueous sodium bicarbonate and the aqueous re-extracted with dichloromethane (10×200 ml). The organic fraction was dried and evaporated and the residue chromatographed (15% EtOH/EtOAc) to give the product (5.5 g).

MS (APCI$^+$) m/z 128 (MH$^+$, 100%)

(b) 5-Fluoro-4-nitro-2-picoline N-oxide

The picoline N-oxide (34a) (2.12 g) was treated with an ice-cooled mixture of filming nitric acid (7.1 ml) and conc. sulfuric acid (70.1 ml), heated at 35–40° C. for 1 hour and 65–70° C. for 5.5 hours, cooled and ice (45 g) added. 10M NaOH was added to pH10 and the mixture extracted with EtOAc (3×30 ml). The organic fraction was dried and evaporated to give a yellow solid (2.16 g).

MS (APCI$^+$) m/z 173 (MH$^+$, 30%), 127 (100%)

(c) 5-Ethoxycarbonylmethylthio-4-nitro-2-picoline N-oxide

Ethyl 2-mercaptoacetate (1.51 g) in dioxan (15.6 ml) under argon was treated with sodium hydride (550 mg of a 60% dispersion in oil) and stirred 4 hours. The picoline N-oxide (34b) (2.16 g) was added and stirring continued 3 days. Water (50 ml) was added and the mixture extracted with chloroform (3×50 ml). The organic fraction was dried and evaporated to give a yellow solid (3.31 g).

MS (APCI$^+$) m/z 273 (MH$^+$, 80%), 125 (100%)

(d) 2-Acetoxymethyl-5-ethoxycarbonylnethylthio-4-nitropyridine

A solution of the picoline N-oxide (34c) (3.31 g) in acetic anhydride (43 ml) was heated to 80° C. for 6 hours, evaporated, xylene (100 ml) added and evaporated. Chromatography of the residue (eluent EtOAc/hexane 1:1) gave the product (1.03 g).

(e) 7-Acetoxymethyl-2-oxo-2,3-dihydro-1H-pyrido[3,4-b][1,4]thiazine

A solution of the nitropyridine (34d) (1.03 g) in glacial acetic acid (27.5 ml) was treated with iron powder (1.75 g), stirred at 60° C. for 3 hours, filtered through kieselguhr and evaporated to dryness. Saturated aqueous sodium bicarbonate (300 ml) was added and extracted with EtOAc (3×200 ml), the organic fraction was dried and evaporated. The residue was redissolved in acetic acid (30 ml), heated to 100° C. for 24 hours, evaporated and chromatographed (eluent EtOAc/hexane 1:1) to give the product (340 mg).

MS (APCI⁻) m/z 237 ([M–H]⁻, 90%), 195 (100%)

(f) 7-Hydroxymethyl-2-oxo-2,3-dihydro-1H-pyrido[3,4-b][1,4]thiazine

A solution of the ester (34e) (340 mg) in dioxan (9 ml) was treated dropwise over 2 hours with 0.5M NaOH (3.7 ml), stirred 18 hours and evaporated. Water (10 ml) was added and the white solid filtered off, washed with water and dried under vacuum to give a solid (231 mg).

MS (APCI⁻) m/z 195 ([M–H]⁻, 100%)

(g) 2-Oxo-2,3-dihydro-1H-pyrido[3,4-b][1,4]thiazine-7-carbaldehyde

A mixture of the alcohol (34f) (226 mg), manganese dioxide (600 mg), THF (22.5 ml) and 1,2-dichloroethane (22.5 ml) was heated at 65° C. for 18 hours under argon. Filtration through kieselguhr and evaporation of solvent gave an off-white solid (173 mg).

MS (APCI⁻) m/z 193 ([M–H]⁻, 100%).

(h) Title Compound

A solution of (R)-2-(4-aminopiperidin-1-yl)-1-(6-methoxyquinolin-4-yl)ethanol (1d) (78 mg, 0.26 mmole) in CH$_2$Cl$_2$ (3 mL) and EtOH (0.2 mL) was treated with anhydrous Na$_2$SO$_4$ (100 mg) and aldehyde (34 g) (50 mg, 0.26 mmole). The resulting solution was stirred at room temperature for 14 hr and then sodium triacetoxy borohydride (82 mg, 0.39 mmole) was added. The resulting slurry was stirred at room temperature for a further 10 hr, then was quenched by the addition of water (2 mL) and the volatiles were removed in vacuo. The residue was partitioned between EtOAc (2×20 mL) and brine (5 mL). The organic phases were combined, dried (MgSO$_4$), and concentrated in vacuo. The resulting oil was purified by flash chromatography on silica gel (gradient: 0–10% MeOH/CH$_2$Cl$_2$) to afford the title compound (35 mg, 28%) as a colorless oil:

¹H NMR (400 MHz, CDCl$_3$) δ 8.78 (d, 1H), 8.40 (s, 1H), 8.21 (d, 1H), 7.78 (d, 1H), 7.12 (d, 1H), 6.90 (s, 1H), 5.70–5.80 (dd, 1H), 5.21–5.30 (dd, 1H), 4.03 (s, 3H), 3.89 (s, 2H), 3.39–3.49 (m, 2H), 3.04–3.10 (dd, 1H), 2.83–2.90 (d, 1H), 2.18–2.70 (m, 4H), 1.50–2.05 (m, 4H).

MS (ES) m/z 481 (M+H)⁺.

Example 35

(R)-2-{4-[(3,4-Dihydro-2H-pyrido[3,2-b][1,4]thiazin-6-ylmethyl)-amino]-piperidin-1-yl}-1-(6-methoxy-quinolin-4-yl)-ethanol, dihydrochloride

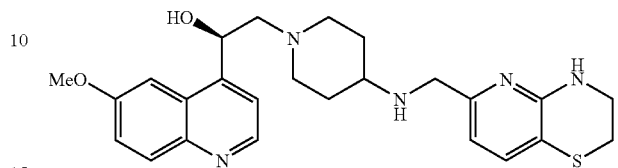

(a) (3,4-Dihydro-2H-pyrido[3,2-b][1,4]thiazine-6-yl)-methanol

A solution of methyl 3-oxo-3,4-dihydro-2H-pyrido[3,2-b][1,4]thiazine-6-carboxylate (31a) (1.0 g) in dry tetrahydrofuran (170 ml) was treated with a 1M solution of lithium aluminium hydride in ether (14 ml) and the mixture was heated under reflux for 18 hours. It was cooled and a slight excess of 2N sodium hydroxide was added followed by chloroform and anhydrous sodium sulphate and the mixture was stirred for 30 minutes and filtered. The solution was evaporated to dryness to give a semi-solid (0.482 g)

MS (APCI⁺) m/z 183 (MH⁺)

(b) 3,4-Dihydro-2H-pyrido[3,2-b][1,4]thiazine-6-carboxaldehyde

The alcohol (35a) (0.482 g) in dry dichloromethane (50 ml) was stirred with manganese dioxide (1.2 g) for 18 hours and the mixture was filtered. The filtrate was evaporated and chomatographed on silica gel, eluting with methanol-dichloromethane (1:50) to afford a yellow solid (0.24 g)

(c) Title Compound (R)-2-(4-Aminopiperidin-1-yl)-1-(6-methoxyquinolin-4-yl)ethanol (1 d) hydrochloride (172 mg, 0.51 mmole), aldehyde (35b) (92 mg, 0.51 mmole), and Et$_3$N (0.071 mL, 0.51 mmole) were combined in CH$_2$Cl$_2$ (2 mL), and the mixture was stirred overnight. MeOH (3 mL) and NaBH$_4$ (30 mg, 0.79 mmole) were added, and the reaction was stirred at room temperature for 2 hr. The solvent was removed in vacuo, and the residue was partitioned between H$_2$O and CHCl$_3$. The organic layer was washed with brine and dried (Na$_2$SO$_4$). The solvent was removed in vacuo, and the residue was dissolved in a mixture of 1:2 MeOH/EtOAc (5 mL). A solution of HCl in Et$_2$O (1.0 M, 1.02 mL, 1.02 mmole) was added, and the precipitated solid was collected, washed with EtOAc, and dried to afford the title compound (146 mg, 53%).

¹H NMR (400 MHz, CD$_3$OD) δ 9.06 (d, J=5.7 Hz, 1H), 8.33 (d, J=5.7 Hz, 1H), 8.22 (d, J=9.9 Hz, 1H), 7.87 (s, 1H), 7.86(d, J=9.9 Hz, 1H), 7.59 (d, J=7.6 Hz, 1H), 6.85 (d, J=7.6 Hz, 1H), 6.43 (d, J=9.0 Hz, 1H), 4.35 (s, 2H), 4.21 (s, 3H), 4.15 (m, 1H), 3.85 (m, 2H), 3.31–3.81 (m, 5H), 3.16(m, 2H), 2.40–2.64 (m, 2H), 2.20–2.45 (m, 2H).

MS (ES) m/z 466.0 (M+H)⁺.

Example 36

7-Fluoro-6-{{1-[(R)-2-hydroxy-2-(6-methoxyquinolin-4-yl)ethyl]piperidin-4-ylamino}methyl}-4H-benzo[1,4]thiazin-3-one, monotrifluoroacetate

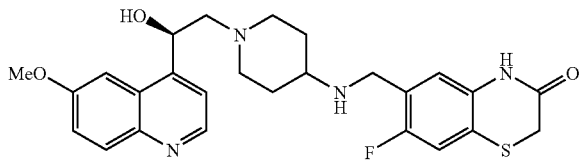

(a) 1-tert-Butoxycarbonyl-4-[(7-fluoro-3-oxo-3,4-dihydro-2H-benzo[1,4]thiazin-6-ylmethyl)amino]piperidine To a stirred solution of aldehyde (22 g) (0.22 g, 1.05 mmole) in CH$_2$Cl$_2$ (20 mL) and dry MeOH (5 mL) at RT under N$_2$ was added 4-amino-1-(tert-butoxycarbonyl)piperidine (0.31 mg, 1.5 mmole). After 36 h, the reaction mixture was concentrated. The remaining residue was dissolved in dry isopropanol (20 mL) and reacted with NaBH$_4$ (0.08 mg, 2.1 mmole). After 12 h at RT, the reaction was concentrated under vacuum and the residue was purified by flash chromatography on silica gel (5% MeOH/CH$_2$Cl$_2$) to afford a yellow solid (0.4 g, 97%).

MS (ES) m/z 396 (M+H)$^+$.

(b) 7-Fluoro-6-(piperidin-4-ylaminomethyl)-4H-benzo[1,4]thiazin-3-one

The carbamate (36a) was treated with 6 N HCl at RT under N$_2$. After 30 h, 1.0 N NaOH was added to the reaction until pH=7, and the solution was concentrated under vacuum. Flash chromatography on silica gel (20% MeOH/CH$_2$Cl$_2$) afforded an off-white solid (0.27 mg, 91%).

MS (ES) m/z 296 (M+H)$^+$.

(c) Title Compound

To a stirred solution of amine (36b) (0.27 g, 0.9 mmole) in dry DMF at RT under N$_2$ was added the oxirane (1b) (0.2 g, 1.0 mmole). The solution was treated with lithium perchlorate (0.1 g, 0.9 mmole) added portionwise at RT. The reaction mixture was stirred and heated at 80° C. for 36 hr, then was cooled to room temperature and concentrated under vacuum. The residue was purified by flash chromatography on silica gel (50:1 CH$_2$Cl$_2$/MeOH containing 2% NH$_4$OH). Further purification by reversed-phase preparative HPLC (gradient elution: 5 to 95% CH$_3$CN/H$_2$O containing 0.1% TFA) gave the title compound (0.05 g, 12%).

MS (ES) m/z 497 (M+H)$^+$

Example 37

6-{{1-[(R)-2-Hydroxy-2-(6-methoxyquinolin-4-yl)ethyl]piperidin-4-ylamino}methyl}-4H-pyrido[3,2-b][1,4]oxazin-3-one, hydrochloride

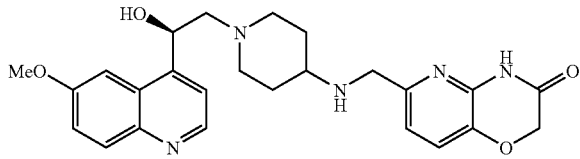

(R)-2-(4-Aminopiperidin-1-yl)-1-(6-methoxyquinolin-4-yl)ethanol (1d) hydrochloride (189 mg, 0.56 mmole), aldehyde (30e) (100 mg, 0.56 mmole), and Et$_3$N (0.078 mL, 0.56 mmole) were combined in DMF (2 mL), and the mixture was stirred overnight. MeOH (3 mL) and NaBH$_4$ (32 mg, 0.84 mmole) were added, and the reaction was stirred at room temperature for 30 min. 6.0 N HCl (0.2 mL) was added, and the reaction was stirred for an additional 5 min. The reaction was quenched with saturated NaHCO$_3$ (2 mL), the solvent was removed in vacuo, and the residue was partitioned between H$_2$O and CHCl$_3$. The organic layer was washed with brine and dried (Na$_2$SO$_4$). The solvent was removed in vacuo, and the residue was dissolved in a mixture of 1:3 MeOH/EtOAc (5 mL). A solution of HCl in Et$_2$O (1.0 M, 0.56 mL, 0.56 mmole) was added, and the precipitated solid was collected, washed with EtOAc, and dried to afford the title compound (100 mg, 36%).

$^1$H NMR (400 MHz, CD$_3$OD) δ 9.05 (d, J=5.7 Hz, 1H), 8.31 (d, J=5.7 Hz, 1H), 8.20 (d, J=9.9 Hz, 1H), 7.87 (s, 1H), 7.85 (d, J=8.0 Hz, 1H), 7.39 (d, J=8.0 Hz, 1H), 7.13 (d, J=8.1 Hz, 1H), 6.44 (d, J=9.2 Hz, 1H), 4.70 (s, 2H), 4.34 (s, 2H), 4.15 (s, 3H), 4.01 (m, 1H), 3.31–3.75 (m, 6H), 2.40–2.54 (m, 2H), 2.20–2.45 (m, 2H).

MS (ES) m/z 464.0 (M+H)$^+$.

Example 38

(R)-2-{4-[(2,3-Dihydro-1H-pyrido[2,3-b][1,4]thiazin-7-ylmethyl)-amino]-piperidin-1-yl}-1-(6-methoxy-quinolin-4-yl)-ethanol, dihydrochloride

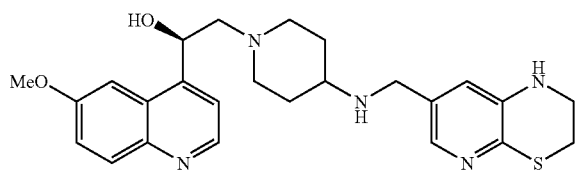

(a) (2,3-Dihydro-1H-pyrido[2,3-b][1,4]thiazin-7-yl)methanol

A solution of methyl ester (20b) (1.0 g) in dry tetrahydrofuran (170 ml) was treated with a 1M solution of lithium aluminium hydride in ether (14 ml) and the mixture was heated under reflux for 18 hours. It was cooled and a slight excess of 2N sodium hydroxide was added followed by chloroform and anhydrous sodium sulphate, and the mixture was stirred for 30 minutes and filtered. The solution was evaporated to dryness to give an oil (0.70 g).

MS (APCI$^+$) m/z 183 (MH$^+$)

(b) 2,3-Dihydro-1H-pyrido[2,3-b][1,4]thiazine-7-carboxaldehyde

The alcohol (38a) (0.70 g) in dry tetrahydrofuran-chloroform (1:1) (50 ml) was stirred with manganese dioxide (1.2 g) for 18 hours and the mixture was filtered. The filtrate was evaporated and chomatographed on silica gel, eluting with chloroform to afford a yellow solid (0.205 g).

MS (APCI$^+$) m/z 181 (MH$^+$)

(c) Title Compound

To a stirred solution of (R)-2-(4-aminopiperidin-1-yl)-1-(6-methoxyquinolin-4-yl) ethanol (1d) hydrochloride salt (0.146 g, 0.43 mmole) in CH₂Cl₂ (3 mL) and dry methanol (2 mL) at RT was added triethylamine (60 uL, 0.52 mmole), aldehyde (38b) (0.065 g, 0.36 mmole), and granular Na₂SO₄ (approximately 200 mg). After 12 h, the reaction was filtered through a sintered-glass funnel and the filtrate was concentrated and azeotroped three times with acetonitrile. The remaining residue was dissolved in dry methanol and reacted with NaBH₄ (0.04 g, 1.0 mmole). After 12 h at RT, the mixture was poured into saturated aqueous sodium bicarbonate solution (10 mL) and extracted with chloroform (3×10 mL). The combined organic phases were dried over Na₂SO₄, filtered, and concentrated. The residue was dissolved in methanol (1 mL) and diluted with ethyl acetate (4 mL). While stirring a solution of 1.0 M HCl in ether (0.8 mL) was added dropwise. The product was collected by suction filtration, washed with ethyl acetate then Et₂O, and dried under vacuum to afford the title compound (0.145 g, 75%) as a tan solid.

MS (ES) m/z 466 (M+H)$^+$.

Example 39

(R)-2-{4-[(3,4-Dihydro-2H-pyrido[3,2-b][1,4]thiazin-6-ylmethyl)-amino]-piperidin-1-yl}-1-(6-methoxy-[1,5]naphthyridin-4-yl)-ethanol, dihydrochloride

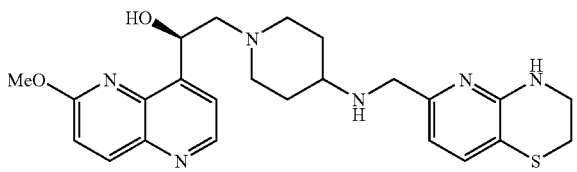

(R)-2-(4-Aminopiperidin-1-yl)-1-(6-methoxy-[1,5]naphthyridin-4-yl)ethanol (2f) (186 mg, 0.61 mmole), aldehyde (35b) (92 mg, 0.51 mmole), and anhydrous Na₂SO₄ powder (a catalytic amount) were combined in CH₂Cl₂ (2 mL), and the mixture was stirred overnight. MeOH (3 mL) and NaBH₄ (30 mg, 0.79 mmole) were added, and the reaction was stirred at room temperature for 2 hr. The solvent was removed in vacuo, and the residue was partitioned between H₂O and CHCl₃. The organic layer was washed with brine and dried (Na₂SO₄). The solvent was removed in vacuo, and the residue was dissolved in a mixture of 1:2 MeOH/EtOAc (5 mL). A solution of HCl in Et₂O (1.0 M, 1.02 mL, 1.02 mmole) was added, and the precipitated solid was collected, washed with EtOAc, and dried to afford the title compound (135 mg, 49%).

$^1$H NMR (400 MHz, CD₃OD) δ 9.10 (d, J=5.6 Hz, 1H), 8.47 (d, J=9.3 Hz, 1H), 8.48 (d, J=5.6 Hz, 1H), 7.68 (d, J=9.6 Hz, 1H), 7.62 (d, J=9.3 Hz, 1H), 6.94 (d, J=7.7 Hz, 1H), 6.36 (d, J=8.3 Hz, 1H), 4.38 (s, 2H), 4.25 (s, 3H), 4.15 (m, 1H), 3.71–3.91 (m, 5H), 3.31–3.52 (m, 3H), 3.30 (s, 1H), 2.40–2.54 (m, 2H), 2.20–2.45 (m, 2H).

MS (ES) m/z 467.0 (M+H)$^+$.

Example 40

(R)-2-{4-(2,3-dihydro-[1,4]dioxino[2,3-b]pyridin-7-ylmethyl)amino]piperidin-1-yl}-1-(6-methoxyquinolin-4-yl)ethanol

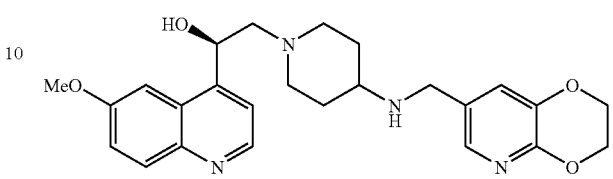

(a) 5-Bromo-pyridine-2,3-diol

This compound was made according to the procedure of Dallacker, F; Fechter, P; Mues, V Journal Z. Naturforsch, 1979, 34b, 1729–1736 from 2-furaldehyde.

MS (APCI+) m/z 190/192 (M+).

(b) 7-Bromo-2,3-dihydro-[1,4]dioxino[2,3-b]pyridine

The diol (40a) (34 g) in DMF (400 ml) and potassium carbonate (51 g) was treated with 1,2-dibromoethane (16 mL) and the mixture was heated at 85° C. overnight and evaporated. The residue was treated with sodium hydroxide, extracted with ethyl acetate and chromatographed on silica gel, eluting with methanol-dichloromethane (1:50) to afford a pale yellow solid (4.92 g; 13%)

MS (APCI+) m/z 216/218 (MH+).

(c) 2,3-Dihydro-[1,4]dioxino[2,3-b]pyridine-7-carboxylic acid butyl ester

Bromide (40b) (1.14 g) was slurried in butanol at room temperature and degassed with a stream of carbon monoxide gas for 10 minutes. 1,8-diazabicyclo[5.4.0]undec-7-ene (0.50 mL, 3.38 mmol), palladium dichloride (30 mg, 0.169 mmol) and 1,3-bis(diphenylphosphino)propane (139 mg, 0.338 mmol) was added. The mixture was heated to 100° C. under an atmosphere of carbon monoxide for 12 hours. The volatiles were then removed under reduced pressure and the residue partitioned between ethyl acetate (2×100 mL) and water (20 mL). The organic phases were combined and dried over magnesium sulfate. The solvent was once again removed in vacuo and the residue subjected to purification on silica gel employing an ethyl acetate and hexane solvent gradient. This provided the desired product as a colourless oil (0.436 g, 54%).

MS (APCI+) m/z 238 (MH+).

(d) (2,3-Dihydro-[1,4]dioxino[2,3-b]pyridin-7-yl)-methanol

Ester (40c) was dissolved in tetrahydrofuran (10 mL). The solution was cooled to 0° C. and a solution of lithium aluminium hydride in tetrahydrofuran (1M, 3.68 mL, 3.68 mmol) was added dropwise. The reaction was stirred at 0° C. for 1 hour and then quenched by the addition of water (2 mL). The volatiles were removed in vacuo and the residue partitioned between ethyl acetate (3×100 mL) and water (20 mL). The organic phases were combined and concentrated to provide the desired compound which was used without further purification (320 mg).

MS (APCI+) mkz 168 (MH+).

(e) 2,3-Dihydro-[1,4]dioxino[2,3-b]pyridine-7-carboxaldehyde

The alcohol (40d) (0.67 g) in dichloromethane (20 mL) was stirred overnight with manganese dioxide (1.5 g), filtered, evaporated and chromatographed on silica gel, eluting with methanol-dichloromethane (1:50) to give a colourless oil (0.49 g, 74%).

MS (APCI+) m/z 166 (MH+).

(f) Title Compound

To a stirred solution of (R)-2-(4-aminopiperidin-1-yl)-1-(6-methoxyquinolin-4-yl) ethanol (1d) mono hydrochloride salt (0.18 g, 0.55 mmole) in CH$_2$Cl$_2$ (25 mL) and dry ethanol (10 mL) at RT was added the aldehyde (40e) (0.09 g, 0.55 mmole), triethylamine (0.08 mL, 0.60 mmole), and granular Na$_2$SO$_4$ (approximately 100 mg). After 36 h, the reaction was filtered through a sintered-glass funnel and the filtrate was concentrated. The remaining residue was dissolved in dry ethanol and reacted with NaBH$_4$ (0.02 g, 0.55 mmole). After 12 h at RT, the reaction was concentrated under vacuum and the residue was dissolved in a mixture of H$_2$O (2 mL) and saturated aqueous NaHCO$_3$ (10 mL). The aqueous solution was extracted with EtOAc (2×50 mL) and the combined organic phases were washed with brine then were dried over Na$_2$SO$_4$. Flash chromatography on silica gel (9:1 CHCl$_3$/MeOH containing 5% NH$_4$OH) afforded the title compound (0.17 g, 69%) as a white solid.

$^1$H NMR (400 MHz, CDCl$_3$) δ 8.75 (d, J=4.5 Hz, 1H), 8.04 (d, J=9.8 Hz, 1H), 7.73 (d, J=2.0 Hz, 1H), 7.63 (d, J=4.5 Hz, 1H), 7.35 (m, 1H), 7.25 (d, J=2.0 Hz, 1H), 7.16 (d, J=2.0 Hz, 1H), 5.42 (m, 1H), 4.41 (m, 2H), 4.23 (m, 2H), 3.92 (s, 3H), 3.74 (s, 2H), 3.25 (m, 1H), 2.83 (m, 2H), 2.57 (m, 2H), 2.37 (app t, J=9.8 Hz, 1H), 2.20 (app t, J=9.8 Hz, 1H), 1.96 (m, 2H), 1.49 (m, 2H).

MS (ES) m/z 451 (M+H)$^+$.

The following Examples 100–108 were prepared from the corresponding carboxaldehyde, which were prepared from commercially available starting materials by standard methods, by analogous methods to Example 1. Example 109 was prepared from Example 18 by hydrogenation over Pd on carbon.

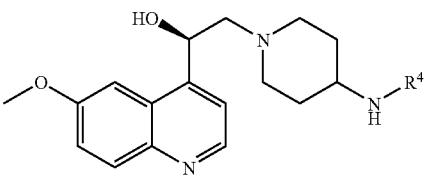

R$^4$ = —U—R$^5$

| Example | salt | U | R$^5$ | |
|---|---|---|---|---|
| 100 | AY | CH$_2$ | 6-benzooxazin-3-one-2,2-Me | 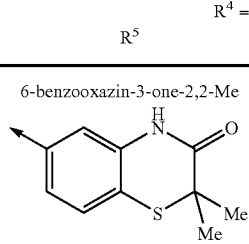 |
| 101 | AY | CH$_2$ | 6-benzooxazin-3-one-4-Me | 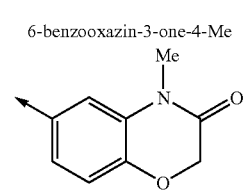 |
| 102 | AY | CH$_2$ | 6-benzothiazol-2-one-3-Me | 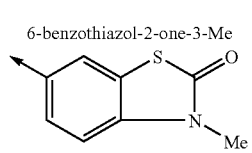 |
| 103 | AY | CH$_2$ | 6-dioxobenzothiazin-3-one | 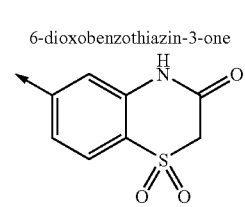 |

| | | | -continued | |
|---|---|---|---|---|
| 104 | AY | CH₂ | 7-benzooxazin-3-one-4-Me | |
| 105 | AY | CH₂ | 7-(3,4-dihydro-1H-quinolin-2-one) | |
| 106 | AY | CH₂ | 6-(7,8-difluoro-4H-benzo[1,4]thiazin-3-one) | |
| 107 | AY | CH₂ | 7-[4-methyl-3,4-dihydro-1H-quinoxalin-2-one] | |
| 108 | AY | CH₂ | 2-[6,7-dihydro-4H-pyrazolo[1,5-a]pyrimidin-5-one] | |
| 109 | AY | CH₂ | 5-[6-amino-benzo[1,3]dioxole] | |

| Example | salt | R¹ | X | U | R⁴ = —U—R⁵<br>R⁵ |
|---|---|---|---|---|---|
| 110 | M | 3-CO₂Et (mixture of isomers) | CH | CH₂ | 6-benzothiazin-3-one |
| 111 | AY | 4-CO₂CH₂CH=CH₂ | N | CH₂ | 6-benzothiazin-3-one |

| 112 | B | 4-CO₂H | | N | CH₂ | 6-benzothiazin-3-one 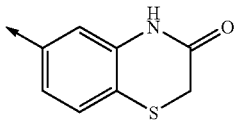 |

Example 110 was prepared from 4-amino-1-[(R)-2-hydroxy-2-(6-methoxy-quinolin-4-yl)-ethyl]-piperidine-3-carboxylic acid ethyl ester (Example 2(e) of WO01/07433) by the method of Example 16. Example 111 was prepared from 4-amino-piperidine-1,4-dicarboxylic acid mono-tert-butyl ester (comercially available) by reaction with aldehyde (6c) and triacetoxyborohydride, allyl bromide/triethylamine/DMF, de-protection with trifluoroacetic acid and finally reaction with oxirane (2e) in acetonitrile and lithium perchlorate. Example 112 was prepared from Example 111 by reaction with Pd(Ph₃P)₄ and Bu₃SnH in THF.

Example 113

6-({1-[(R)-2-Hydroxy-2-(6-methoxy-[1,5]naphthyridin-4-yl)ethyl]piperidin-4-ylamino}methyl)-3,4-dihydro-1H-[1,8]naphthyridin-2-one

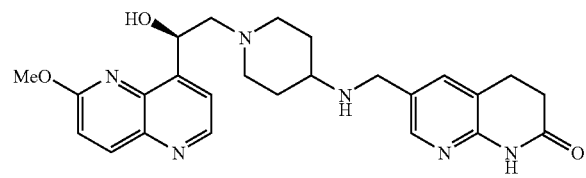

(a) 2-Amino-3-(hydroxymethyl)pyridine

Solid 2-aminonicotinic acid (199 g, 1.44 mole) was added in portions over 4 hr to 1.0 M LiAlH₄ in THF (3 L, 3 mole) with stirring under Argon. An ice-bath was applied to control the temperature below 30° C. After the addition was complete, the reaction was heated at reflux for 16 hr, then was cooled to 0° C. and carefully quenched by sequential addition of H₂O (120 mL), 15% NaOH in H₂O (120 mL), and H₂O (350 mL). The resulting thick suspension was stirred for 1 hr, then was filtered through a pad of celite®. The filter pad was rinsed with THF (1 L), and the filtrate was concentrated to dryness to give the title compound (156 g, 87%) as a pale yellow waxy solid: MS (ES) m/e 125.1 (M+H)⁺; ¹H NMR (400 MHz, DMSO-d₆) δ 7.84 (dd, 1H), 7.37 (m, 1H), 6.53 (dd, 1H), 5.65 (br s, 2H), 5.16(t, 1H), 4.34 (d, J=4.6 Hz, 2H).

(b) 2-Amino-5-bromo-3-(hydroxymethyl)pyridine hydrobromide

To a stirred solution of 2-amino-3-(hydroxymethyl)pyridine (113a) (156 g, 1.257 mole) in HOAc (2.5 L) at ambient temperature was added bromine (64.1 mL, 1.257 mole) dropwise over 1 hr. A suspension began to form during the addition. An exotherm to 36° C. was controlled with an ice bath. After the addition, the reaction mixture was stirred at ambient temperature overnight. The yellow precipitate was filtered, washed with ether and air-dried to give the title compound (289 g, 81%): MS (ES) m/e 203.2 (M+H)⁺; ¹H NMR (400 MHz, DMSO-d₆, free base) δ 7.89 (d, J=2.3 Hz, 1H), 7.52 (s, 1H), 5.92 (br s, 2H), 5.29 (br s, 1H), 4.30 (s, 2H).

(c) 2-Amino-5-bromo-3-(bromomethyl)pyridine hydrobromide

A suspension of 2-amino-5-bromo-3-(hydroxymethyl)pyridine hydrobromide (113b) (289 g, 1.02 mole) in 48% aqueous HBr (2.9 L) was heated at reflux for 12 hrs. Complete solution occurred during heating. The reaction mixture was cooled and a crystalline precipitate formed. This was filtered and washed with ethyl acetate and air dried to give the title compound (305 g, 86%).

(d) Methyl (±)-6-bromo-2-oxo-1,2,3,4-tetrahydro-1H-[1,8]naphthyridine-3-carboxylate To a solution of dimethyl malonate (224 g, 1.7 mole) in DMF (2 L) and THF (2 L) stirred under argon and chilled to 3° C. with an ice-acetone bath was added NaH (60% Nujol dispersion, 69.2 g, 1.7 mole) in portions over 1.5 hr. The anion solution was stirred for 15 min at ca. 5° C., then 2-amino-5-bromo-3-(bromomethyl)pyridine hydrobromide (113c) (200 g, 0.56 mole) was added in portions over 15 min. The reaction mixture was allowed to warm to ambient temperature during overnight stirring and then was heated to 80° C. for 2 hr. The reaction was then cooled and filtered and the precipitate was washed with ethyl acetate. This solid was then vigorously stirred in 2 L water for 15 min and again filtered and air-dried to give the title compound (113 g, 71%): MS (ES) m/e 286 (M+H)⁺.

(e) 6-Bromo-3,4-dihydro-1H-1H-[1,8]naphthyridin-2-one

To a suspension of methyl (±)-6-bromo-2-oxo-1,2,3,4-tetrahydro-1H-[1,8]naphthyridine-3-carboxylate (113d) (170 g, 0.596 mole) in CH₃OH (10 L) was added 1.0 M NaOH (2.5 L). The reaction mixture was stirred and heated at reflux for 5 hrs and then cooled to ambient temperature. The suspension was acidified with 1.0 M HCl (3.0 L) and then was stirred and heated at reflux overnight. The reaction slurry was cooled and filtered and the solid was washed with water and vacuum dried to give the title compound (122 g of the hydrate, 90%) as an off-white solid, HPLC purity, 94%: MS (ES) m/e 228 (M+H)⁺.

(f) 6-Vinyl-3,4-dihydro-1H-[1,8]naphthyridin-2-one

6-Bromo-3,4-dihydro-1H-[1,8]naphthyridin-2-one (113e) (4.6 g, 20.3 mmole) and tributyl(vinyl)tin (7.7 g, 24.4 mmole) were dissolved in DMF (200 mL) and the solution was degassed with nitrogen. (Ph₃P)₄Pd (590 mg, 0.5 mmole) was added to the solution. The reaction was heated to 105° C. under nitrogen overnight, then was cooled to room temperature and filtered through a sintered glass funnel. The filtrate was washed with NH₄OH and extracted with EtOAc (2×150 mL). The combined organic phases were washed with brine, dried over Na₂SO₄ and concentrated in vacuo to afford the title compound (2.1 g, 60%) as an off white solid: MS (ES) m/e 175 (M+H)⁺.

(g) 7-Oxo-5,6,7,8-tetrahydro-[1,8]naphthyridine-3-carboxaldehyde

6-Vinyl-3,4-dihydro-1H-[1,8]naphthyridin-2-one (113f) (0.46 g, 2.6 mmole) was dissolved in CH₂Cl₂ (50 mL) and the solution was cooled to −78° C. Ozone was bubbled through the solution with stirring until a pale blue color appeared, then the excess ozone was removed by bubbling oxygen through the solution for 15 min. Dimethylsulfide (0.30 mL, 4.8 mmole) was added and the reaction was stirred at −78° C. for 3 hr, then was allowed to warm to RT overnight. The solvent was removed in vacuo. Flash chromatography on silica gel (9:1 CHCl₃/MeOH containing 5% NH₄OH) afforded the title compound (0.21 g, 45%) as an off white solid: MS (ES) m/e 177 (M+H)⁺.

(h) Title Compound

To a stirred solution of (R)-2-(4-aminopiperidin-1-yl)-1-(6-methoxy-[1,5]naphthyridin-4-yl)ethanol (2f) (0.34 g, 1.13 mmole) in dichloroethane (10 mL) and dry ethanol (5 mL) at RT was added 7-oxo-5,6,7,8-tetrahydro-[1,8]naphthyridine-3-carboxaldehyde (113 g) (0.20 g, 1.13 mmole) and granular Na₂SO₄ (approximately 100 mg). After 72 h, the reaction was concentrated. The remaining residue was dissolved in dry ethanol and reacted with NaBH₄ (0.043 g, 1.13 mmole). After 12 h at RT, the reaction was concentrated under vacuum and the residue was dissolved in a mixture of H₂O (10 mL) and saturated aqueous NaHCO₃ (50 mL). The aqueous solution was extracted with EtOAc (2×75 mL) and the combined organic phases were washed with brine then were dried over Na₂SO₄. Flash chromatography on silica gel (9:1 CHCl₃/MeOH containing 5% NH₄OH) afforded the title compound (0.11 g, 21%) as a white solid: ¹H NMR (400 MHz, d₆-DMSO) δ 10.43 (br s, 1H), 8.77 (d, J=4.5 Hz, 1H), 8.23 (d, J=9.0 Hz, 1H), 8.01 (s, 1H), 7.75 (d, J=4.5 Hz, 1H), 7.58 (s, 1H), 7.24 (d, J=9.0 Hz, 1H), 5.77 (m, 1H), 5.23 (br s, 1H), 4.02 (s, 3H), 3.63 (s, 2H), 3.38 (m, 2H), 3.11 (m, 1H), 2.83 (m, 2H), 2.65 (m, 1H), 2.47 (m, 2H), 2.32 (m, 1H), 2.17 (m, 1H), 1.79 (m, 2H), 1.27 (m, 2H); MS (ES) m/e 463 M+H)⁺.

The following Examples 150 and 151 were prepared by analogous methods to Example 7, using the carboxaldehydes 5b and 14a.

Example 180 was prepared from 6-trifluoromethoxy-quinolin-4-ylamine (prepared from 4-trifluoromethoxyaniline by addition to methyl propiolate, cyclisation in refluxing Dowtherm, reaction with trifluoromethane sulfonic anhydride and heating with n-propylamine) by the method of Example 7b-d. Example 181 was prepared from aldehyde 14a and [3-(4-amino-quinolin-6-yloxy)-propyl]-carbamic acid benzyl ester (prepared from Example (1a) by cleavage of the methyl ether to the corresponding phenol with concentrated hydrobromic acid, esterification using concentrated hydrochloric acid/methanol, alkylation of the phenol with (3-bromo-propyl)-carbamic acid benzyl ester using potassium carbonate in N,N-dimethylformamide, hydrolysis of the methyl ester to the corresponding acid with aqueous sodium hydroxide, Curtius rearrangement of the acid with diphenylphosphoryl azide in tert-butanol to give [6-(3-benzyloxycarbonylamino-propoxy)-quinolin-4-yl]-carbamic acid tert-butyl ester then standard treatment with trifluoroacetic acid) by the method of Example 7b-d followed by hydrogenation.

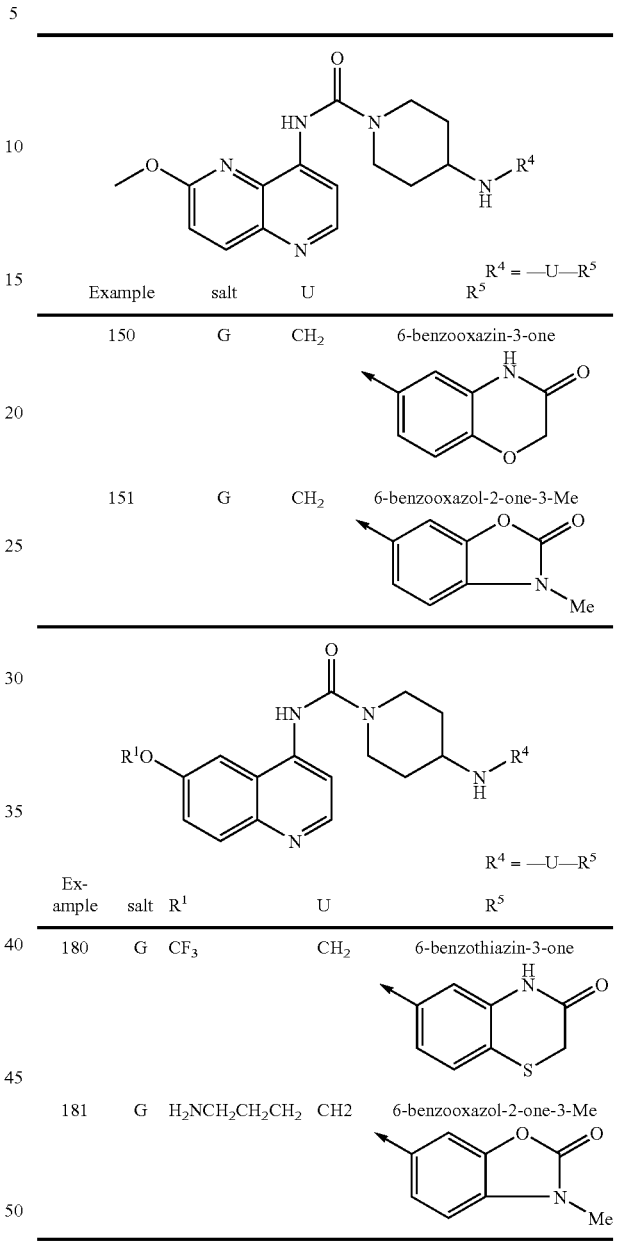

Example 186

3-Oxo-3,4-dihydro-2H-pyrido[3,2-b][1,4]thiazine-6-carboxylic Acid {1-[(R)-2-hydroxy-2-(6-methoxyquinolin-4-yl)ethyl]piperidin-4-yl}amide dihydrochloride

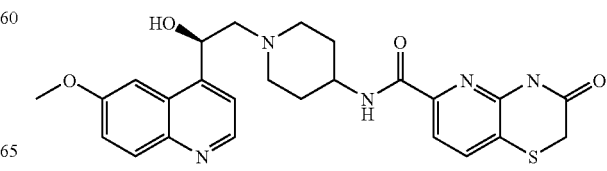

Free base of the title compound was prepared by the method of Example 189 using 4-amino-1-[(R)-2-hydroxy-2-(6-methoxyquiolin-4-yl)ethyl]piperidine (1d) (34%). 1H NMR (CDCL₃) δ 1.45–1.6 (1H, m), 1.6–1.75 (1H, m), 2.01 (2H, broad d), t), 2.52 (1H, t), 2.60 (1H, dd), 2.85–2.95 (2H, m), 3.31 (1H, broad d), 3.56 (2H, s), 3.94 (3H, s), 3.9–4.05 (1H, m), 5.46 (1H, dd), 7.19 (1H, d), 7.3–7.4 (2H, m), 7.7–7.8 (2H, m), 7.82 (1H, d), 8.15 (1H, d), 8.83 (1H, d), 9.57 (1H, broad s)

Free base was converted into dihydrochloride by the method of Example 189.

MS (–ve ion electrospray) m/z 492 ([M–H]⁻, 100%)

Example 187

7-Bromo-3-oxo-3,4-dihydro-2H-pyrido[3,2-b][1,4]thiazine-6-carboxylic acid {1-[(R)-2-hydroxy-2-(6-methoxyquinolin-4-yl)ethyl]piperidin-4-yl}amide dihydrochloride

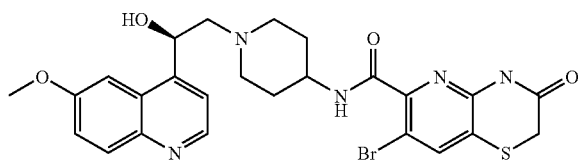

Free base of the title compound was prepared by the method of Example 189 using 4-amino-1-[(R)-2-hydroxy-2-(6-methoxyquinolin-4-yl)ethyl]piperidine (1d) and 7-bromo-3-oxo-3,4-dihydro-2H-pyrido[3,2-b][1,4]thiazine-6-carboxylic acid (33c) (32%). 1H NMR (CDCL₃) δ 1.25–1.5 (1H, m), 1.5–1.8 (1H, m), 1.85–2.05 (2H, m), 2.31 (1H, t), 2.47 (1H, t), 2.59 (1H, dd), 2.86 (2H, broad d), 3.28 (1H, broad d), 3.56 (2H, s), 3.8–4.0 (4H, m), 5.46 (1H, dd), 7.18 (1H, d), 7.29 (1H, d), 7.39 (1H, dd), 7.74 (1H, d), 7.91 (1H, s), 8.16 (1H, d), 8.82 (1H d), MS (–ve ion electrospray) m/z 570 and 572 ([M–H]⁻, 100%)

Free base was converted into dihydrochloride by the method of Example 189.

Example 188

7-Bromo-3-oxo-3,4-dihydro-2H-pyrido[3,2-b][1,4]thiazine-6-carboxylic acid {1-[(R)-2-hydroxy-2-(6-methoxy[1,5]naphthyridin-4-yl)ethyl]piperidin-4-yl}amide dihydrochloride

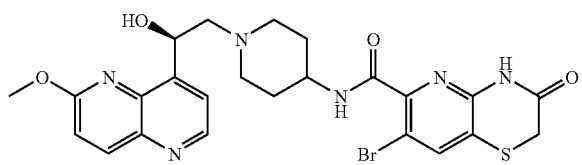

Free base of the title compound was prepared by the method of Example 189 using 4-amino-1-[(R)-2-hydroxy-2-(6-methoxy[1,5]naphthyridin-4-yl)ethyl]piperidine (2f) and 7-bromo-3-oxo-3,4-dihydro-2H-pyrido[3,2-b][1,4]thiazine-6-carboxylic acid (33c) (27%).

1H NMR (CDCl₃) δ 1.4–1.8 (2H, m), 2.0–2.2 (2H, m), 2.32 (1H, dt), 2.4–2.6 (2H, m), 2.87 (1H, broad d), 3.11 (1H, dd), 3.34 (1H, broad d), 3.56 (2H, s), 3.8–4.1 (4H, m), 5.75 (1H, dd), 7.13 (1H, d), 7.27 (1H, d), 7.83 (1H, d), 7.95 (1H, s), 8.26 (1H, d), 8.81 (1H, d).

MS (–ve ion electrospray) m/z 571 and 573 ([M–H]⁻, 100%)

Free base was converted into dihydrochloride by the method of Example 189.

Example 189

3-Oxo-3,4-dihydro-2H-pyrido[3,2-b][1,4]thiazine-6-carboxylic acid {1-[(R)-2-hydroxy-2-(6-methoxy[1,5]naphthyridin-4-yl)ethyl]piperidin-4-yl}amide dihydrochloride

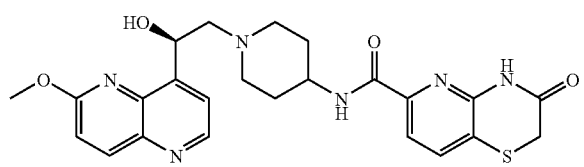

A solution of (R)-1-[2-hydroxy-2-(6-methoxy[1,5]naphthyridin-4-yl)]ethyl-4-aminopiperidine (Example 2f) (100 mg), 3-oxo-3,4-dihydro-2H-pyrido[3,2-b][1,4]thiazine-6-carboxylic acid (31b) (70 mg) and pyridine (0.027 ml) in dichloromethane (2 ml)/DMF (2 ml) was ice-cooled and treated with dicyclohexylcarbodiimide (206 mg). After warming to room temp. over 1 hour the mixture was stirred 18 hours, diluted with chloroform (20 ml), washed with saturated aqueous sodium bicarbonate, dried and evaporated to dryness. Chromatography, eluting with chloroform/methanol/0.88 aqueous ammonia 19:1:0.1, gave free base of the title compound (129 mg).

1H NMR (CDCl₃) δ1.5–1.9 (2H, m), 2.0–2.1 (2H, m), 2.33 (1H, dt), 2.4–2.6 (2H, m), 2.87 (1H, d), 3.11 (1H, dd), 3.34 (1H, d), 3.55 (2H, s), 3.95–4.05 (1H, m), 4.05 (3H, s), 5.75 (1H, dd), 7.13 (1H, d), 7.42 (1H, d), 7.77 (1H, d), 7.84–7.86 (2H, m), 8.26 (1H d), 8.70 (1H, broad s), 8.81 (1H, d).

A chloroform solution of this material was treated with 1M HCl in ether (0.65 ml) and evaporated to dryness to give title compound (115 mg).

MS (–ve ion electrospray) m/z 493 ([M–H]⁻, 100%)

The following Example 190 was prepared from 5-oxo-2,3-dihydro-5H-thiazolo[3,2-a]pyrimidine-6-carboxylic acid by the method of Example 12b. Examples 191 and 192 were prepared by analogous methods from the acids 6a and 2,2-difluorobenzo[1,3]dioxole-5-carboxylic acid. Examples 200–204 were prepared by analogous methods to Example 15, but Example 204 used amine Example 2f.

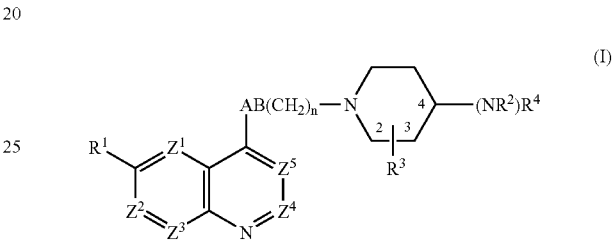

R⁴ = —U—R⁵

| Example | salt | X | U | R⁵ |
|---|---|---|---|---|
| 190 | DZ | CH | CO | 4-thiazolopyrimidin-5-one |
| 191 | G | CH | CO | 6-benzothiazin-3-one |
| 192 | CH | CO | 5-(2,2-Difluoro-benzo[1,3]dioxole) |
| 200 | G | CH | SO₂ | 6-benzodioxine |
| 201 | G | CH | SO₂ | 6-benzooxazin-3-one |
| 202 | G | CH | SO₂ | 6-(7-chloro-benzothiazin-3-one) |
| 203 | G | CH | SO₂ | 7-benzothiazepin-4-one |
| 204 | N | SO₂ | 6-benzothiazin-3-one |

Key to salts
AY dioxalate
G oxalate
DZ mesylate
M trifluoroacetate
B dihydrochloride Biological Activity The MIC (μg/ml) of test compounds against various organisms was determined: *S. aureus* Oxford, *S. aureus* WCUH29, *S. pneumoniae* 1629, *S. pneumoniae* N1387, *S. pneumoniae* ERY 2, *H. influenzae* Q1, *E.faecalis* 1.

Examples 1–4, 6–10, 16, 18, 19, 22–40, 186–189 have an MIC of less than or equal to 0.125 μg/ml; 5, 11–15, 17, 20, 21, 101, 102, 105, 106, 109–110, 191, 192, 203, 204 have an MIC of less than or equal to 2 μg/ml; 100, 103, 104, 107, 111–113, 150, 190, 200–202 have an MIC less than or equal to 32 μg/ml against one or more of the above range of gram positive and gram negative bacteria.

What is claimed is:
1. A compound of formula (I) or a pharmaceutically acceptable salt and/or N-oxide thereof:

(I)

wherein:
one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;

$R^1$ and $R^{1a}$ are independently hydrogen; hydroxy; $(C_{1-6})$alkoxy optionally substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted$(C_{1-6})$ alkyl; halogen; $(C_{1-6})$alkyl; $(C_{1-6})$alkylthio; trifluoromethyl; trifluoromethoxy; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups; or when $Z^5$ is $CR^{1a}$, $R^{1a}$ may instead be cyano, hydroxymethyl or carboxy; provided that when none of $Z^1$, $Z^2$, $Z^3$, $Z^4$ and $Z^5$ is N, then $R^1$ is not hydrogen;

$R^2$ is hydrogen, or $(C_{1-4})$alkyl or $(C_{2-4})$alkenyl optionally substituted with 1 to 3 groups selected from:

amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl;

halogen; ($C_{1-4}$)alkylthio; trifluoromethyl; hydroxy optionally substituted by ($C_{1-4}$)alkyl, ($C_{2-4}$)alkenyl, ($C_{1-4}$)alkoxycarbonyl, ($C_{1-4}$)alkylcarbonyl, ($C_{2-4}$)alkenyloxycarbonyl, ($C_{2-4}$)alkenylcarbonyl; oxo; ($C_{1-4}$) alkylsulphonyl; ($C_{2-4}$)alkenylsulphonyl; or ($C_{1-4}$)aminosulphonyl wherein the amino group is optionally substituted by ($C_{1-4}$)alkyl or ($C_{2-4}$)alkenyl;

$R^3$ is hydrogen; or $R^3$ is in the 2-, 3- or 4-position and is:

carboxy; ($C_{1-6}$)alkoxycarbonyl; ($C_{2-6}$)alkenyloxycarbonyl aminocarbonyl wherein the amino group is optionally substituted by hydroxy, ($C_{1-6}$)alkyl, hydroxy($C_{1-6}$) alkyl, aminocarbonyl($C_{1-6}$)alkyl, ($C_{2-6}$)alkenyl, ($C_{1-6}$) alkylsulphonyl, trifluoromethylsulphonyl, ($C_{2-6}$) alkenylsulphonyl, ($C_{1-6}$)alkoxycarbonyl, ($C_{1-6}$) alkylcarbonyl, ($C_{2-6}$)alkenyloxycarbonyl or ($C_{2-6}$) alkenylcarbonyl and optionally further substituted by ($C_{1-6}$)alkyl, hydroxy($C_{1-6}$)alkyl, aminocarbonyl($C_{1-6}$) alkyl or ($C_{2-6}$)alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; or ($C_{1-4}$)alkyl or ethenyl optionally substituted with any of the substituents listed above for $R^3$ and/or 0 to 2 groups $R^{12}$ independently selected from:

halogen; ($C_{1-6}$)alkylthio; trifluoromethyl; ($C_{1-6}$)alkoxycarbonyl; ($C_{1-6}$)alkylcarbonyl; ($C_{2-6}$)alkenyloxycarbonyl; ($C_{2-6}$)alkenylcarbonyl; hydroxy optionally substituted by ($C_{1-6}$)alkyl, ($C_{2-6}$)alkenyl, ($C_{1-6}$) alkoxycarbonyl, ($C_{1-6}$)alkylcarbonyl, ($C_{2-6}$)alkenyloxycarbonyl, ($C_{2-6}$)alkenylcarbonyl or aminocarbonyl wherein the amino group is optionally substituted by ($C_{1-6}$)alkyl, ($C_{2-6}$)alkenyl, ($C_{1-6}$)alkylcarbonyl or ($C_{2-6}$)alkenylcarbonyl; amino optionally mono- or disubstituted by ($C_{1-6}$)alkoxycarbonyl, ($C_{1-6}$)alkylcarbonyl, ($C_{2-6}$)alkenyloxycarbonyl, ($C_{2-6}$)alkenylcarbonyl, ($C_{1-6}$)alkyl, ($C_{2-6}$)alkenyl, ($C_{1-6}$)alkylsulphonyl, ($C_{2-6}$)alkenylsulphonyl or aminocarbonyl wherein the amino group is optionally substituted by ($C_{1-6}$)alkyl or ($C_{2-6}$)alkenyl; aminocarbonyl wherein the amino group is optionally substituted by ($C_{1-6}$)alkyl, hydroxy($C_{1-6}$)alkyl, aminocarbonyl($C_{1-6}$)alkyl, ($C_{2-6}$)alkenyl, ($C_{1-6}$)alkoxycarbonyl, ($C_{1-6}$)alkylcarbonyl, ($C_{2-6}$)alkenyloxycarbonyl or ($C_{2-6}$)alkenylcarbonyl and optionally further substituted by ($C_{1-6}$)alkyl, hydroxy($C_{1-6}$) alkyl, aminocarbonyl($C_{1-6}$)alkyl or ($C_{2-6}$)alkenyl; oxo; ($C_{1-6}$)alkylsulphonyl; ($C_{2-6}$)alkenylsulphonyl; or ($C_{1-6}$)aminosulphonyl wherein the amino group is optionally substituted by ($C_{1-6}$)alkyl or ($C_{2-6}$)alkenyl; or when $R^3$ is in the 3-position, hydroxy optionally substituted as described above;

in addition when $R^3$ is disubstituted with a hydroxy or amino containing substituent and carboxy containing substituent these may together form a cyclic ester or amide linkage, respectively;

$R^4$ is a group —U—$R^5$ where

U is selected from CO, $SO_2$ and $CH_2$ and $R^5$ is an optionally substituted bicyclic carbocyclic or heterocyclic ring system (A):

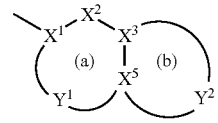

(A)

containing up to four heteroatoms in each ring in which ring (a) is aromatic and ring (b) is non-aromatic;

$X^1$ is C or N;

$X^2$ is N, $NR^{13}$, O, $S(O)_x$, CO or $CR^{14}$;

$X^3$ and $X^5$ are independently N or C;

$Y^1$ is a 0 to 4 atom linker group each atom of which is independently selected from N, $NR^{13}$, O, $S(O)_x$, CO and $CR^{14}$;

$Y^2$ is a 2 to 6 atom linker group, each atom of $Y^2$ being independently selected from N, $NR^{13}$, O, $S(O)_x$, CO, $CR^{14}$ and $CR^{14}R^{15}$;

each of $R^{14}$ and $R^{15}$ is independently selected from: H; ($C_{1-4}$)alkylthio; halo; carboxy($C_{1-4}$)alkyl; halo($C_{1-4}$) alkoxy; halo($C_{1-4}$)alkyl; ($C_{1-4}$)alkyl; ($C_{2-4}$)alkenyl; ($C_{1-4}$)alkoxycarbonyl; formyl; ($C_{1-4}$)alkylcarbonyl; ($C_{2-4}$)alkenyloxycarbonyl ($C_{2-4}$)alkenylcarbonyl; ($C_{1-4}$)alkylcarbonyloxy; ($C_{1-4}$)alkoxycarbonyl($C_{1-4}$) alkyl; hydroxy; hydroxy($C_{1-4}$)alkyl; mercapto($C_{1-4}$) alkyl; ($C_{1-4}$)alkoxy; nitro; cyano; carboxy; amino or aminocarbonyl optionally substituted as for corresponding substituents in $R^3$; ($C_{1-4}$)alkylsulphonyl; ($C_{2-4}$)alkenylsulphonyl; or aminosulphonyl wherein the amino group is optionally mono- or di-substituted by ($C_{1-4}$)alkyl or ($C_{2-4}$)alkenyl; aryl; aryl($C_{1-4}$)alkyl; aryl($C_{1-4}$)alkoxy;

each $R^{13}$ is independently H; trifluoromethyl; ($C_{1-4}$) alkyl optionally substituted by hydroxy, ($C_{1-6}$) alkoxy, ($C_{1-6}$)alkylthio, halo or trifluoromethyl; ($C_{2-4}$)alkenyl; aryl; aryl ($C_{1-4}$)alkyl; arylcarbonyl; heteroarylcarbonyl; ($C_{1-4}$)alkoxycarbonyl; ($C_{1-4}$) alkylcarbonyl; formyl; ($C_{1-6}$)alkylsulphonyl; or aminocarbonyl wherein the amino group is optionally substituted by ($C_{1-4}$)alkoxycarbonyl, ($C_{1-4}$)alkylcarbonyl, ($C_{2-4}$)alkenyloxycarbonyl, ($C_{2-4}$)alkenylcarbonyl, ($C_{1-4}$)alkyl or ($C_{2-4}$)alkenyl and optionally further substituted by ($C_{1-4}$)alkyl or ($C_{2-4}$)alkenyl;

each x is independently 0, 1 or 2 n is 0 and AB is $NR^{11}$ CO, CO—$CR^8R^9$, $CR^6R^7$—CO, $NHR^{11}SO_2$, $CR^6R^7$—$SO_2$ or $CR^6R^7$—$CR^8R^9$;

or n is 1 and AB is $NR^{11}CO$, CO—$CR^8R^9$, $CR^6R^7$—CO, $NR^{11}SO_2$, $CONR^{11}$, $CR^6R^7$—$CR^8R^9$, O—$CR^8R^9$ or $NR^{11}$—$CR^8R^9$;

wherein $CR^6R^7$ is $CH_2$, CHOH, $CH(NH_2)$, C(Me)(OH) or CH(Me) and $CR^8R^9$ is $CH_2$;

$R^{10}$ is selected from ($C_{1-4}$)alkyl; ($C_{2-4}$)alkenyl and aryl any of which may be optionally substituted by a group $R^{12}$ as defined above; carboxy; aminocarbonyl wherein the amino group is optionally substituted by hydroxy, ($C_{1-6}$)alkyl, ($C_{2-6}$)alkenyl, ($C_{1-6}$)alkylsulphonyl, trifluoromethylsulphonyl, ($C_{2-6}$)alkenylsulphonyl, ($C_{1-6}$) alkoxycarbonyl, ($C_{1-6}$)alkylcarbonyl, ($C_{2-6}$)alkenyloxycarbonyl or ($C_{2-6}$)alkenylcarbonyl and optionally further substituted by ($C_{1-6}$)alkyl or ($C_{2-6}$)alkenyl; and $R^{11}$ is hydrogen; trifluoromethyl, ($C_{1-6}$)alkyl; ($C_{2-6}$)alkenyl; ($C_{1-6}$)alkoxycarbonyl; ($C_{1-6}$)alkylcarbonyl; or aminocarbonyl wherein the amino group is optionally substituted by ($C_{1-6}$)alkoxycarbonyl, ($C_{1-6}$)alkylcarbonyl, ($C_{2-6}$)alkenyloxycarbonyl, ($C_{2-6}$)alkenylcarbonyl, (C$_{1-6}$)alkyl or (C$_{2-6}$)alkenyl and optionally further substituted by (C$_{1-6}$)alkyl or (C$_{2-6}$)alkenyl;

or where one of R$^3$ and R$^6$ or R$^7$ contains a carboxy group and the other contains a hydroxy or amino group they may together form a cyclic ester or amide linkage.

2. A compound according to claim 1 wherein Z$^5$ is CH or N, Z$^3$ is CH or CF and Z$^1$, Z$^2$ and Z$^4$ are each CH, or Z$^1$ is N, Z$^3$ is CH or CF and Z$^2$, Z$^4$ and Z$^5$ are each CH.

3. A compound according to claim 1 wherein R$^1$ is methoxy and R$^{1a}$ is H or when Z$^3$ is CR$^{1a}$ it may be C—F.

4. A compound according to claim 1 wherein R$^3$ is hydrogen; optionally substituted hydroxy; (C$_{1-4}$)alkoxycarbonyl; CONH$_2$; 1-hydroxyalkyl; CH$_2$CO$_2$H; CH$_2$CONH$_2$; —CONHCH$_2$CONH$_2$; 1,2-dihydroxyalkyl; CH$_2$CN; 2-oxo-oxazolidin-5-yl or 2-oxo-oxazolidin-5-yl(C$_{1-4}$alkyl).

5. A compound according claim 1 wherein n is 0 and either A is CHOH and B is CH$_2$ or A is NH and B is CO.

6. A compound according to claim 1 wherein —U— is —CH$_2$—.

7. A compound according to claim 1 wherein in the heterocyclic ring (A) Y$^2$ has 3–5 atoms including (a) NR$^{13}$, O or S bonded to X$^5$ and NHCO bonded via N to X$^3$, or (b) O or NH bonded to X$^3$.

8. A compound according to claim 1 wherein R$^5$ is selected from:

2,3-dihydro-benzo[1,4]dioxin-6-yl
benzo[1,3]dioxol-5-yl
2,2-difluoro-benzo[1,3]dioxol-5-yl
4H-benzo[1,4]oxazin-3-one-6-yl
4H-benzo[1,4]thiazin-3-one-6-yl
7-fluoro-4H-benzo[1,4]oxazin-3-one-6-yl
6-chloro-benzo[1,3]dioxol-5-yl
5-fluoro-3-methyl-3H-benzooxazol-2-one-6-yl
(2,3-dihydro-[1,4]dioxino[2,3-c]pyridin-7-yl
3-oxo-3,4-dihydro-2H-pyrido[3,2-b][1,4]thiazin-6-yl
3,4-dihydro-2H-pyrido[3,2-b][1,4]thiazin-6-yl and
7-bromo-3-oxo-3,4-dihydro-2H-pyrido[3,2-b][1,4]thiazin-6-yl.

9. A compound according to claim 1 selected from:

(R)-2-{4-[(2,3-Dihydro-benzo[1,4]dioxin-6-ylmethyl)-amino]-piperidin-1-yl}-1-(6-methoxy-quinolin-4-yl)-ethanol, (R)-2-{4-[(2,3-Dihydro-benxo[1,4]dioxin-6-ylmethyl)-amino]-piperidin-1-yl}-1-(6-methoxy-[1,5]naphthyridin-4-yl)-ethanol, (R)-2-{4-[(Benzo[1,3]dioxol-5-ylmethyl)-amino]-piperidin-1-yl}-1-(6-methoxy-quinolin-4-yl)-ethanol, 6-({1-[(R)-2-Hydroxy-2-(6-methoxy-quinolin-4-yl)-ethyl]-piperidin-4-ylamino}-methyl)-4H-benzo[1,4]oxazin-3-one, 6-({1-[(R)-2-Hydroxy-2-(6-methoxy-quinolin-4-yl)-ethyl]-piperidin-4-ylamino}-methyl)-4H-benzo[1,4]thiazin-3-one, 7-Fluoro-6-({1-[(R)-2-Hydroxy-2-(6-methoxy-quinolin-4-yl)-ethyl]-piperidin-4-ylamino}-methyl)-4H-benzo[1,4]oxazin-3-one, 6-({1-[(R)-2-Hydroxy-2-(6-methoxy-[1,5]naphthyridin-4-yl)-ethyl]-piperidin-4-ylamino}methyl)-4H-benzo[1,4]oxazin-3-one, (R)-2-{4-[(6-Chloro-benzo[1,3]dioxol-5-ylmethyl)-amino]-piperidin-1-yl}-1-(6-methoxy-quinolin-4-yl)-ethanol, 5-Fluoro-6-({1-[(R)-2-hydroxy-2-(6-methoxy-quinolin-4-yl)-ethyl]-piperidin-4-ylamino}-methyl)-3-methyl-3H-benzoxazol-2-one, 2,3-Dihydro-benzo[1,4]dioxine-6-carboxylic acid {1-[(R)-2-hydroxy-2-(6-methoxy-quinolin-4-yl)-ethyl]-piperidin-4-yl}-amide, 6-({1-[(R)-2-Hydroxy-2-(6-methoxy-quinolin-4-yl)-ethyl]-piperidin-4-ylamino}-methyl)-3-methyl-3H-benzoxazole-2-thione, 6-({1-[(R)-2-Hydroxy-2-(6-methoxy-quinolin-4-yl)-ethyl]-piperidin-4-ylamino}-methyl)-3-methyl-3H-benzoxazol-2-one, 3-oxo-3,4-dihydro-2H-benzo[1,4]thiazine-6-sulfonic acid {1-[(R)-2-hydroxy-2-(6-methoxy-quinolin-4-yl)-ethyl]-piperidin-4-yl}-amide, 6-({1-[(R)-2-Hydroxy-2-(6-methoxy-[1,5]naphthyridin-4-yl)-ethyl]-piperidin-4-ylamino}-methyl)-4H-benzo[1,4]thiazin-3-one, 4-oxo-2,3,4,5-tetrahydro-benzo[b][1,4]thiazepine-7-sulfonic acid {1-[(R)-2-hydroxy-2-(6-methoxy-[1,5]naphthyridin-4-yl)-ethyl]-piperidin-4-yl}-amide, (R)-1-(6-Methoxy-quinolin-4-yl)-2-{4-[(6-nitro-benzo[1,3]dioxol-5-ylmethyl)-amino]-piperidin-1-yl}-ethanol, (R)-2-{4-[(2,3-Dihydro-[1,4]dioxino[2,3-b]pyridin-6-ylmethyl)-amino]-piperidin-1-yl}-1-(6-methoxy-quinolin-4-yl)-ethanol, 7-({1-[(R)-2-Hydroxy-2-(6-methoxy-quinolin-4-yl)-ethyl]-piperidin-4-ylamino}-methyl)-1-H-pyrido[2,3-b][1,4]thiazin-2-one, 6-({1-[(R)-2-Hydroxy-2-(6-methoxy-quinolin-4-yl)-ethyl]-piperidin-4-ylamino}-methyl)-2-(R/S)-methyl-4H-benzo[1,4]thiazin-3-one, 7-Fluoro-6-{{1-[(R)-2-hydroxy-2-(6-methoxy-[1,5]naphthyridin-4-yl)ethyl]piperidin-4-ylamino}methyl}-4H-benzo[1,4]thiazin-3-one, (R)-2-{4-[(7-Fluoro-2,3-dihydrobenzo[1,4]dioxin-6-ylmethyl)amino]piperidin-1-yl}-1-(6-methoxy-[1,5]naphthyridin-4-yl)ethanol, (R)-2-{4-(2,3-Dihydro-[1,4]dioxino[2,3-c]pyridin-7-ylmethyl)amino]piperidin-1-yl}-1-(6-methoxy-[1,5]naphthyridin-4-yl)ethanol, (R)-1-(6-Methoxy-[1,5]naphthyridin-4-yl)-2-{4-[(5,6,7,8-tetrahydro-[1,8]naphthyridin-2-ylmethyl)amino]piperidin-1-yl}ethanol, (R)-1-(6-Methoxyquinolin-4-yl)-2-{4-[(5,6,7,8-tetrahydro-[1,8]naphthyridin-2-ylmethyl)amino]piperidin-1-yl}ethanol, 6-[({(3S,4S)-3-Hydroxy-1-[(R)-2-hydroxy-2-(6-methoxyquinolin-4-yl)-ethyl]piperidin-4-ylamino}methyl)-4H-benzo[1,4]thiazin-3-one, 6-[({(3R,4R)-3-Hydroxy-1-[(R)-2-hydroxy-2-(6-methoxyquinolin-4-yl)-ethyl]piperidin-4-ylamino}methyl)-4H-benzo[1,4]thiazin-3-one, 7-{{1-[(R)-2-Hydroxy-2-(6-methoxy-[1,5]naphthyridin-4-yl)ethyl]piperidin-4-ylamino}methyl}-1H-pyrido[2,3-b][1,4]thiazin-2-one, 7-{{1-[(R)-2-Hydroxy-2-(6-methoxy-quinolin-4-yl)-ethyl]-piperidin-4-ylamino}methyl}-2,3-dihydro-5H-benzo[b][1,4]thiazepine-4-one, 6-{{1-[(R)-2-Hydroxy-2-(6-methoxy-[1,5]naphthyridin-4-yl)ethyl]piperidin-4-ylamino}methyl}-4H-pyrido[3,2-b][1,4]oxazin-3-one, 6-{{1-[(R)-2-Hydroxy-2-(6-methoxy-[1,5]naphthyridin-4-yl)ethyl]piperidin-4-ylamino}methyl}-4H-pyrido[3,2-b][1,4]thiazin-3-one, (R)-2-{4-[(3,4-Dihydro-2H-pyrido[3,2-b][1,4]oxazin-6-ylmethyl)-amino]-piperidin-1-yl}-1-(6-methoxy-[1,5]naphthyridin-4-yl)-ethanol, 7-Bromo-6-{{1-[(R)-2-hydroxy-2-(6-methoxy-[1,5]naphthyridin-4-yl)ethyl]piperidin-4-ylamino}methyl}-4H-pyrido[3,2-b][1,4]thiazin-3-one, 7-{{1-[(R)-2-Hydroxy-2-(6-methoxy-[1,5]naphthyridin-4-yl)ethyl]piperidin-4-ylamino}methyl}-1H-pyrido[3,4-b][1,4]thiazin-2-one, (R)-2-{4-[(3,4-Dihydro-2H-pyrido[3,2-b][1,4]thiazin-6-ylmethyl)-amino]-piperidin-1-yl}-1-(6-methoxy-quinolin-4-yl)-ethanol, 7-Fluoro-6-{{1-[(R)-2-hydroxy-2-(6-methoxyquinolin-4-yl)ethyl]piperidin-4-ylamino}methyl}-4H-benzo[1,4]thiazin-3-one, 6-{{1-[(R)-2-Hydroxy-2-(6-methoxyquinolin-4-yl)ethyl]piperidin-4-ylamino}methyl}-4H-pyrido[3,2-b][1,4]oxazin-3-one, (R)-2-{4-[(2,3-Dihydro-1H-pyrido[2,3-b][1,4]thiazin-7-ylmethyl)-amino]-piperidin-1-yl}-1-(6-methoxy-quinolin-4-yl)-ethanol, (R)-2-{4-[(3,4-Dihydro-2H-pyrido[3,2-b](1,4]thiazin-6-ylmethyl)-amino]-piperidin-1-yl}-1-(6-methoxy-[1,5]naphthyridin-4-yl)-ethanol, (R)-2-{4-(2,3-dihydro-[1,4]dioxino[2,3-b]pyridin-7-ylmethyl)amino]piperidin-1-yl}-1-(6-methoxyquinolin-4-yl)ethanol, 3-oxo-3,4-dihydro-2H-pyrido[3,2-b][1,4]thiazine-6-carboxylic acid {1-[(R)-2-hydroxy-2-(6-methoxyquinolin-4-yl)ethyl]piperidin-4-yl}amide, 7-Bromo-3-oxo-3,4-dihydro-2H-pyrido[3,2-b][1,4]thiazine-6-carboxylic acid {1-[(R)-2-hydroxy-2-(6-methoxyquinolin-4-yl)ethyl]piperidin-4-yl}amide, 7-Bromo-3-oxo-3,4-dihydro-2H-pyrido[3,2-b][1,4]thiazine-6-carboxylic acid {1-[(R)-2-hydroxy-2-(6-methoxy[1,5]naphthyridin-4-yl)ethyl]piperidin-4-yl}amide, 3-oxo-3,4-dihydro-2H-pyrido[3,2-b][1,4]thiazine-6-carboxylic acid {1-[(R)-2-hydroxy-2-(6-methoxy(1,5]naphthyridin-4-yl)ethyl]piperidin-4-yl}amide, 6-({1-[(R)-2-Hydroxy-2-(6-methoxy-[1,5]naphthyridin-4-yl)ethyl]piperidin-4-ylamino}methyl)-3,4-dihydro-1H-[1,8]naphthyridin-2-one, the following compounds (a)-(j) of formula (1):

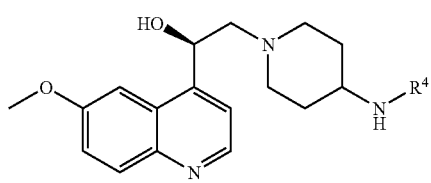

(1)

wherein R⁴=-U-R⁵:

| | U | R⁵ |
|---|---|---|
| (a) | $CH_2$ | 6-benzooxazin-3-one-2,2-Me |
| (b) | $CH_2$ | 6-benzooxazin-3-one-4-Me |
| (c) | $CH_2$ | 6-benzothiazol-2-one-3-Me |
| (d) | $CH_2$ | 6-dioxobenzothiazin-3-one |
| (e) | $CH_2$ | 7-benzooxazin-3-one-4-Me |
| (f) | $CH_2$ | 7-(3,4-dihydro-1H-quinolin-2-one) |
| (g) | $CH_2$ | 6-(7,8-difluoro-4H-benzo[1,4]thiazin-3-one) |
| (h) | $CH_2$ | 7-[4-methyl-3,4-dihydro-1H-quinoxalin-2-one] |
| (i) | $CH_2$ | 2-[6,7-dihydro-4H-pyrazolo[1,5-a]pyrimidin-5-one] |
| (j) | $CH_2$ | 5-[6-amino-benzo[1,3]dioxide] | the following compounds (a)-(c) of formula (2):

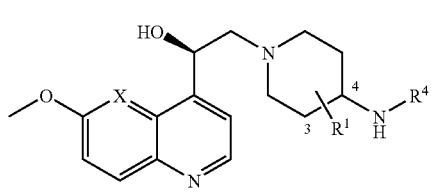

(2)

wherein $R^4$=-U-$R^5$:

| | $R^1$ | X | U | $R^5$ |
|---|---|---|---|---|
| (a) | 3-$CO_2$Et (mixture of isomers) | CH | $CH_2$ | 6-benzothiazin-3-one |
| (b) | 4-$CO_2CH_2CH=CH_2$ | N | $CH_2$ | 6-benzothiazin-3-one |
| (c) | 4-$CO_2$H | N | $CH_2$ | 6-benzothiazin-3-one , | the following compounds (a)-(b) of formula (3):

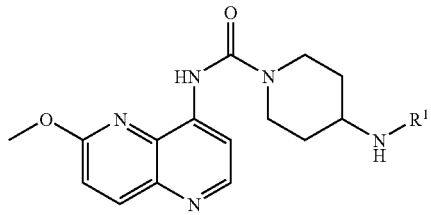

(3)

wherein $R^4$=-U-$R^5$:

| | U | $R^5$ |
|---|---|---|
| (a) | $CH_2$ | 6-benzooxazin-3-one |
| (b) | $CH_2$ | 6-benzooxazol-2-one-3-Me | the following compounds (a)-(b) of formula (4):

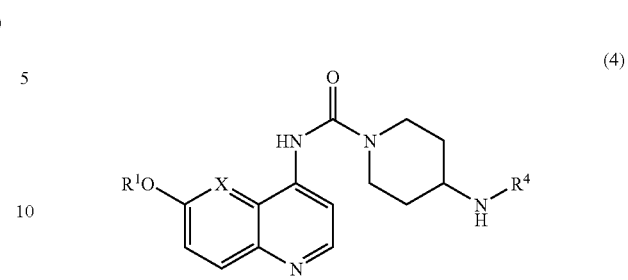

(4)

wherein $R^4$=-U-$R^5$:

| | $R^1$ | U | $R^5$ |
|---|---|---|---|
| (a) | $CF_3$ | $CH_2$ | 6-benzothiazin-3-one |
| (b) | $H_2NCH_2CH_2CH_2$ | $CH_2$ | 6-benzooxazol-2-one-3-Me | and
the following compounds (a)-(h) of formula (5):

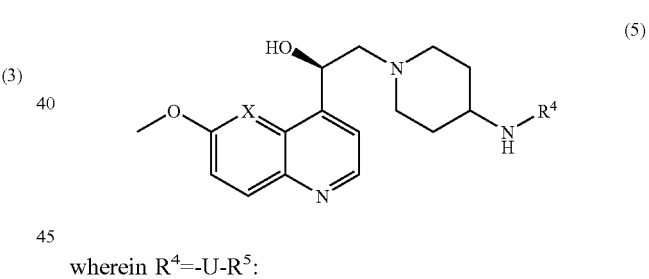

(5)

wherein $R^4$=-U-$R^5$:

| | X | U | $R^5$ |
|---|---|---|---|
| (a) | CH | CO | 4-thiazolopyrimidin-5-one |
| (b) | CH | CO | 6-benzothiazin-3-one |
| (c) | CH | CO | 5-(2,2-Difluoro-benzo[1,3]dioxole) |

-continued

| | X | U | R⁵ | |
|---|---|---|---|---|
| (d) | CH | SO₂ | 6-benzodioxine | 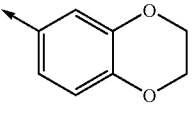 |
| (e) | CH | SO₂ | 6-benzooxazin-3-one | 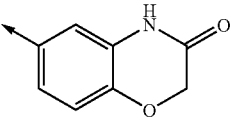 |
| (f) | CH | SO₂ | 6-(7-chlorobenzothiazin-3-one) | 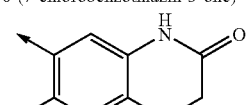 |
| (g) | CH | SO₂ | 7-benzothiazepin-4-one |  |
| (h) | N | SO₂ | 6-benzothiazin-3-one | 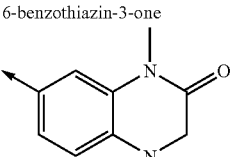 | or a pharmaceutically acceptable salt and/or N-oxide thereof.

10. A method of treatment of bacterial infections in mammals, particularly in man, which method comprises the administration to a mammal in need of such treatment an effective amount of a compound according to claim 1.

11. A pharmaceutical composition comprising a compound according to claim 1, and a pharmaceutically acceptable carrier.

12. A process for preparing a compound of formula (I) according to claim 1, or a pharmaceutically acceptable salt and/or N-oxide thereof, which process comprises reacting a compound of formula (IV) with a compound of formula (V):

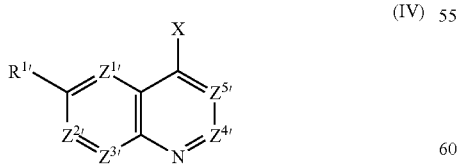

(IV)

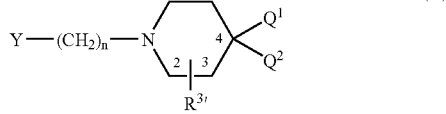

(V)

wherein n is as defined in formula (I); $Z^{1'}$, $Z^{2'}$, $Z^{3'}$, $Z^{4'}$, $Z^{5'}$, $R^{1'}$, and $R^{3'}$ are $Z^1$, $Z^2$, $Z^3$, $Z^4$, $Z^5$, $R^1$, and $R^3$ as defined in formula (I) or groups convertible thereto; $Q^1$ is $NR^{2'}R^{4'}$ or a group convertible thereto wherein $R^{2'}$ and $R^{4'}$ are $R^2$ and $R^4$ as defined in formula (I) or groups convertible thereto and $Q^2$ is H or $R^{3'}$ or $Q^1$ and $Q^2$ together form an optionally protected oxo group;

(i) X is A'-COW, Y is H and n is 0;
(ii) X is $CR^6$=$CR^8R^9$, Y is H and n is 0;
(iii) X is oxirane, Y is H and n is 0;
(iv) X is N=C=O and Y is H and n is 0;
(v) one of X and Y is $CO_2R^Y$ and the other is $CH_2CO_2R^X$;
(vi) X is $CHR^6R^7$ and Y is C(=O)$R^9$;
(vii) X is $CR^7$=$PR^{Z3}$ and Y is C(=O)$R^9$ and n=1;
(viii) X is C(=O)$R^7$ and Y is $CR^9$=$PR^{Z3}$ and n=1;
(ix) Y is COW and X is $NHR^{11'}$ or NR11'COW and n=0 or 1 or when n=1 X is COW and Y is $NHR^{11'}$ or NR11'COW;
(x) X is $NHR^{11'}$ and Y is C(=O)$R^8$ and n=1;
(xi) X is $NHR^{11'}$ and Y is $CR^8R^9$W and n=1;
(xii) X is $NR^{11'}$COCH₂W or $NR^{11'}SO_2CH_2W$ and Y is H and n=0;
(xiii) X is $CR^6R^7SO_2W$ and Y is H and n=0;
(xiv) X is W or OH and Y is CH₂OH and n is 1;
(xv) X is $NHR^{11'}$ and Y is $SO_2W$ or X is $NR^{11'}SO_2W$ and Y is H, and n is 0;
(xvi) X is W and Y is $CONHR^{11'}$;
in which W is a leaving group; $R^X$ and $R^Y$ are $(C_{1-6})$alkyl; $R^Z$ is aryl or $(C_{1-6})$alkyl; A' and $NR^{11'}$ are A and $NR^{11}$ as defined in formula (I), or groups convertible thereto; and oxirane is:

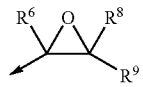

wherein $R^6$, $R^8$ and $R^9$ are as defined in formula (I);
and thereafter optionally or as necessary converting $Q^1$ and $Q^2$ to $NR^{2'}R^{4'}$;
converting A', $Z^{1'}$, $Z^{2'}$, $Z^{3'}$, $Z^{4'}$, $Z^{5'}$, $R^{1'}$, $R^{2'}$, $R^{3'}$, $R^{4'}$ and $NR^{11'}$; to A, $Z^1$, $Z^2$, $Z^3$, $Z^4$, $Z^5$, $R^1$, $R^2$, $R^3$, $R^4$ and $NR^{11}$; converting A-B to other A-B, interconverting $R^1$, $R^2$, $R^3$ and/or $R^4$,
and/or forming a pharmaceutically acceptable salt and/or N-oxide thereof.

13. A process according to claim 12, wherein W is halo or imidazolyl.

* * * * *